United States Patent
Evans et al.

(10) Patent No.: US 10,781,181 B2
(45) Date of Patent: Sep. 22, 2020

(54) N-((HET) ARYLMETHYL)-HETEROARYL-CARBOXAMIDES COMPOUNDS AS PLASMA KALLIKREIN INHIBITORS

(71) Applicant: Kalvista Pharmaceuticals Limited, Porton Down, Wiltshire (GB)

(72) Inventors: David Michael Evans, Salisbury (GB); Rebecca Louise Davie, Salisbury (GB); Hannah Joy Edwards, Salisbury (GB); Simon Teanby Hodgson, Bedfordshire (GB)

(73) Assignee: KALVISTA PHARMACEUTICALS LIMITED, Porton Down, Wiltshire (GB)

( * ) Notice: Subject to any disclaimer, the term of this patent is extended or adjusted under 35 U.S.C. 154(b) by 0 days.

(21) Appl. No.: 15/526,421

(22) PCT Filed: Nov. 26, 2015

(86) PCT No.: PCT/GB2015/053613
§ 371 (c)(1),
(2) Date: May 12, 2017

(87) PCT Pub. No.: WO2016/083818
PCT Pub. Date: Jun. 2, 2016

(65) Prior Publication Data
US 2017/0305863 A1  Oct. 26, 2017

(30) Foreign Application Priority Data

Nov. 27, 2014  (GB) .................................. 1421085.0

(51) Int. Cl.

| | | |
|---|---|---|
| *C07D 401/10* | (2006.01) |
| *C07D 231/14* | (2006.01) |
| *C07D 231/38* | (2006.01) |
| *C07D 401/14* | (2006.01) |
| *C07D 405/14* | (2006.01) |
| *C07D 413/14* | (2006.01) |
| *C07D 401/06* | (2006.01) |
| *C07D 403/06* | (2006.01) |
| *C07D 409/14* | (2006.01) |
| *C07D 413/06* | (2006.01) |
| *C07D 413/10* | (2006.01) |
| *C07D 417/06* | (2006.01) |
| *C07D 417/10* | (2006.01) |
| *C07D 417/14* | (2006.01) |
| *A61K 31/415* | (2006.01) |
| *A61K 31/501* | (2006.01) |
| *A61K 31/416* | (2006.01) |
| *A61K 31/4439* | (2006.01) |
| *A61K 31/4709* | (2006.01) |

(Continued)

(52) U.S. Cl.
CPC .......... *C07D 231/38* (2013.01); *A61K 31/415* (2013.01); *A61K 31/416* (2013.01); *A61K 31/4439* (2013.01); *A61K 31/4709* (2013.01); *A61K 31/501* (2013.01); *A61K 31/506* (2013.01); *C07D 231/14* (2013.01); *C07D 401/06* (2013.01); *C07D 401/10* (2013.01); *C07D 401/14* (2013.01); *C07D 403/06* (2013.01); *C07D 403/10* (2013.01); *C07D 405/14* (2013.01); *C07D 409/14* (2013.01); *C07D 413/06* (2013.01); *C07D 413/10* (2013.01); *C07D 413/14* (2013.01); *C07D 417/06* (2013.01); *C07D 417/10* (2013.01); *C07D 417/14* (2013.01)

(58) Field of Classification Search
CPC ... C07D 401/10; C07D 231/14; C07D 231/38
See application file for complete search history.

(56) References Cited

U.S. PATENT DOCUMENTS

| | | |
|---|---|---|
| 5,187,157 A | 2/1993 | Kettner et al. |
| 7,101,878 B1 | 9/2006 | Anderson et al. |

(Continued)

FOREIGN PATENT DOCUMENTS

| | | |
|---|---|---|
| EA | 201200917 | 12/2012 |
| EP | 1426364 A1 | 6/2004 |

(Continued)

OTHER PUBLICATIONS

Chemical Abstracts Registry No. 955899-78-2, indexed in the Registry file on STN CAS Online on Nov. 25, 2007.*
Chemical Abstracts Registry No. 1575116-26-5, indexed in the Registry file on STN CAS Online Mar. 28, 2014.*
Chemical Abstracts Registry No. 1241137-33-6, indexed in the Registry file on STN CAS Online Sep. 15, 2010.*
Chemical Abstracts Registry No. 1217027-87-6, indexed in the Registry file on STN CAS Online Apr. 5, 2010.*

(Continued)

*Primary Examiner* — Laura L Stockton
(74) *Attorney, Agent, or Firm* — BakerHostetler

(57) ABSTRACT

The present invention provides compounds of formula (I): (I) compositions comprising such compounds; the use of such compounds in therapy (for example in the treatment or prevention of a disease or condition in which plasma kallikrein activity is implicated); and methods of treating patients with such compounds; wherein R5, R6, R7, A, B, U, D, E, W, X, Y and Z are as defined herein.

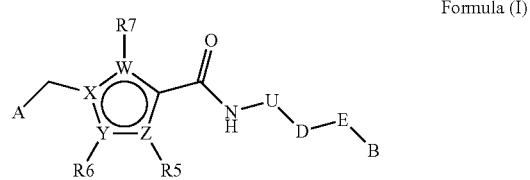

Formula (I)

36 Claims, No Drawings

(51) Int. Cl.
*A61K 31/506* (2006.01)
*C07D 403/10* (2006.01)

(56) References Cited

U.S. PATENT DOCUMENTS

| | | |
|---|---|---|
| 8,207,378 B2 | 6/2012 | Steinmetzer et al. |
| 9,382,219 B2 | 7/2016 | Das et al. |
| 9,512,065 B2 | 12/2016 | Northen et al. |
| 9,533,987 B2 | 1/2017 | Davie et al. |
| 9,670,157 B2 | 6/2017 | Allan et al. |
| 9,738,641 B2 | 8/2017 | Edwards et al. |
| 10,221,161 B2 | 3/2019 | Edwards et al. |
| 2007/0254894 A1 | 11/2007 | Kane et al. |
| 2008/0221091 A1 | 9/2008 | Gege et al. |
| 2009/0163545 A1 | 6/2009 | Goldfarb |
| 2010/0113782 A1 | 5/2010 | Bolin et al. |
| 2011/0152533 A1 | 6/2011 | Sinha et al. |
| 2012/0298326 A1 | 11/2012 | Born |
| 2014/0213611 A1 | 7/2014 | Evans et al. |
| 2014/0378474 A1 | 12/2014 | Flohr et al. |
| 2015/0191421 A1 | 7/2015 | Northen et al. |
| 2015/0315198 A1 | 11/2015 | Li et al. |
| 2017/0305863 A1 | 10/2017 | Evans et al. |
| 2018/0319782 A1 | 11/2018 | Davie et al. |

FOREIGN PATENT DOCUMENTS

| | | |
|---|---|---|
| EP | 1568698 A1 | 8/2005 |
| EP | 2281885 A1 | 2/2011 |
| JP | 2010-520294 A | 6/2010 |
| RU | 2485114 C2 | 6/2013 |
| WO | WO9204371 A1 | 3/1992 |
| WO | WO9429335 A1 | 12/1994 |
| WO | WO9507921 A1 | 3/1995 |
| WO | 03/35076 A1 | 5/2003 |
| WO | WO03037274 A2 | 5/2003 |
| WO | WO03076458 A2 | 9/2003 |
| WO | 03/91226 A1 | 11/2003 |
| WO | 2004/062657 A1 | 7/2004 |
| WO | 2004/069792 A2 | 8/2004 |
| WO | 2005/049578 A1 | 6/2005 |
| WO | 2005/079800 A1 | 9/2005 |
| WO | WO2005123680 A1 | 12/2005 |
| WO | WO2006091459 A2 | 8/2006 |
| WO | 2006/114313 A1 | 11/2006 |
| WO | WO2007011626 A2 | 1/2007 |
| WO | 2007/113289 A1 | 10/2007 |
| WO | WO2008016883 A2 | 2/2008 |
| WO | WO2008049595 A1 | 5/2008 |
| WO | WO2008091692 A2 | 7/2008 |
| WO | 2008/121670 A1 | 10/2008 |
| WO | WO2009012998 A1 | 1/2009 |
| WO | 2009/026407 A1 | 2/2009 |
| WO | 2009/083553 A1 | 7/2009 |
| WO | WO2009097141 A1 | 8/2009 |
| WO | 2009/106980 A2 | 9/2009 |
| WO | 2009/114677 A1 | 9/2009 |
| WO | WO2010142801 A1 | 12/2010 |
| WO | 2011/075684 A1 | 6/2011 |
| WO | 2011/094496 A2 | 8/2011 |
| WO | WO11118672 A1 | 9/2011 |
| WO | 2012/009009 A2 | 1/2012 |
| WO | WO2012004678 A2 | 1/2012 |
| WO | WO2012017020 A1 | 2/2012 |
| WO | 2012/142308 A1 | 10/2012 |
| WO | 2012/174362 A1 | 12/2012 |
| WO | 2013/005045 A1 | 1/2013 |
| WO | WO2013048982 A1 | 4/2013 |
| WO | WO2013049096 A1 | 4/2013 |
| WO | 2013/120104 A2 | 8/2013 |
| WO | WO2013111107 A1 | 8/2013 |
| WO | WO2013111108 A1 | 8/2013 |
| WO | 2013/130603 A1 | 9/2013 |
| WO | 2014/006414 A1 | 1/2014 |
| WO | 2014/108406 A1 | 7/2014 |
| WO | 2014/108685 A1 | 7/2014 |
| WO | WO2014108679 A1 | 7/2014 |
| WO | WO2014145986 A1 | 9/2014 |
| WO | WO2014188211 A1 | 11/2014 |
| WO | WO2015022546 A1 | 2/2015 |
| WO | WO2015022547 A1 | 2/2015 |
| WO | WO2015103317 A1 | 7/2015 |
| WO | WO2015134998 A1 | 9/2015 |
| WO | WO2015171526 A2 | 12/2015 |
| WO | WO2015171527 A1 | 12/2015 |
| WO | WO2016011209 A1 | 1/2016 |
| WO | WO2016029214 A1 | 2/2016 |
| WO | WO2016044662 A1 | 3/2016 |
| WO | 2016/083818 A1 | 6/2016 |
| WO | WO2016083816 A1 | 6/2016 |
| WO | WO2016083820 A1 | 6/2016 |
| WO | WO2016138532 A1 | 9/2016 |
| WO | 2017/001924 | 1/2017 |
| WO | WO2017001926 A2 | 1/2017 |
| WO | WO2017001936 A2 | 1/2017 |
| WO | WO2017072020 A1 | 5/2017 |
| WO | WO2017072021 A1 | 5/2017 |
| WO | 2017/207983 A1 | 12/2017 |
| WO | 2017/207985 A1 | 12/2017 |
| WO | 2017/208005 A1 | 12/2017 |
| WO | 2018/011628 A1 | 1/2018 |
| WO | 2019/106359 A1 | 6/2019 |
| WO | 2019/106375 A1 | 6/2019 |
| WO | 2019/106377 A1 | 6/2019 |

OTHER PUBLICATIONS

Chemical Abstracts Registry No. 1147797-44-1, indexed in the Registry file on STN CAS Online May 20, 2009.*
Chemical Abstracts Registry No. 942731-43-3, indexed in the Registry file on STN CAS Online Jul. 19, 2007.*
Chemical Abstracts Registry No. 1295467-87-6, indexed in the Registry file on STN CAS Online May 16, 2011.*
Chemical Abstracts Registry No. 1389653-06-8, indexed in the Registry file on STN CAS Online Aug. 12, 2012.*
Chemical Abstracts Registry No. 1297526-11-4, indexed in the Registry file on STN CAS Online May 19, 2011.*
Chemical Abstracts Registry No. 1296846-83-7, indexed in the Registry file on STN CAS Online May 18, 2011.*
Enamine website on Jul. 25, 2013 from the Internet Archive Way Back Machine {https://web.archive.org/web/20130725053127/http://www.enamine.net/ index.php?option=com_content&task=view&id=22.*
CAS abstract accession Nos. 2009:769551 and 2009:846114, corresponding to U.S. Publication 2009-0163545A1, 5 pages , 2009.
CAS abstract accession No. 2013:1177162, corresponding to Ye et al. Chemical Science, 2013, 4(9), 4 pages.
CAS abstract accession No. 1990:515202, corresponding to Ried et al. Liebigs Annalen der Chemie, 1990, 8, 2 pages.
CAS abstract accession No. 2013:1592386, corresponding to FR2989085 A1 (Commissariat Energie Atomique), 3 pages, 2013.
CAS Extract for Compound 120842-43-4, dated Apr. 18, 2011, 1 page.
CAS Extract for Compound 1197490-19-9, dated Dec. 16, 2009, 1 page.
CAS Extract for Compound 1028094-50-9, dated Jun. 13, 2008, 1 page.
CAS Extract for Compound 1626023-22-0, dated Sep. 25, 2014, 1 page.
CAS Extract for Compound 1388550-15-9, dated Aug. 9, 2012, 1 page.
CAS Extract for Compound 1386962-55-5, dated Aug. 6, 2012, 1 page.
CAS Structures cited in WO201683818 Written Opinion dated Jun. 2, 2016, 290 pages.
Babu et al., "A Simple, Sensitive and Selective Fluorogenic Assay to Monitor Plasma Kallikrein Inhibitory Activity of BCX4161 in Activated Plasma", Journal of Allergy and Clinical Immunology, Feb. 2014, 133(2 Supp), Abstract AB40, p. 1.

(56) References Cited

OTHER PUBLICATIONS

Bhoola et al., "Bioregulation of Kinins: Kallikreins, Kininogens and Kininases", Pharmacological Rev., Mar. 1992, 44(1), pp. 1-80.
Bhoola et al., "Kallikrein-Kinin Cascade" Encyclopedia of Respiratory Medicine, 2006, pp. 483-493.
Bryant et al., "Human Plasma Kallikrein-Kinin System: Physiological and Biochemical Parameters", Cardiovascular and Haematological Agents in Medicinal Chemistry, Jul. 2009, pp. 234-250.
Campbell, "Towards Understanding the Kallikrein-Kinin System: Insights from the Measurement of Kinin Peptides", Brazilian Journal of Medical and Biological Research, Jun. 2000, 33(6), pp. 665-677.
Chilcote et al., "ASP-634: An Oral Drug Candidate for Diabetic Macular Edema", ARVO Mar. 2012, Presentation 2240, Abstract, p. 1.
Clermont et al., "Plasma Kallikrein Mediates Retinal Vascular Dysfunction and Induces Retinal Thickening in Diabetic Rats", Diabetes, May 2011, 60(5), pp. 1590-1598.
Collis et al., "BCX4161, An Oral Kallikrein Inhibitor: Safety and Pharmacokinetic Results of a Phase 1 Study in Healthy Volunteers", Journal of Allergy and Clinical Immunology, vol. 133, Issue 2, Supplement, Feb. 2014, p. AB39.
Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, pp. 1064-1077.
Evans et al., "Selective Inhibitors of Plasma Kallikrein", Immunopharmacology, May 1996, 32(1-3), pp. 115-116.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), pp. 60-71.
Griesbacher et al., "Involvement of Tissue Kallikrein But Not Plasma Kallikrein in the Development of Symptoms Mediated by Endogenous Kinins in Acute Pancreatitis in Rats", British Journal of Pharmacology, 2002, 137, pp. 692-700.
Johansen et al., "Assay of Kallikrein Inhibitors and Levels of Acetone-Activated Kallikrein in Plasma Specimens from Reactors to Dextran or to Contrast Media", International Journal Tissue Reactions, 1986, 8, pp. 185-192.
Kolte et al., "Biochemical Characterization of a Novel High-Affinity and Specific Kallikrein Inhibitor", British Journal of Pharmacology, Apr. 2011, 162(7), pp. 1639-1649.
Lehmann, "Ecallantide (DX-88), a Plasma Kallikrein Inhibitor for the Treatment of Hereditary Angioedema and the Prevention of Blood Loss in On-Pump Cardiothoracic Surgery", Expert Opinion Biol. Ther., Jul. 2008, 8(8), pp. 1187-1199.
Leinweber et al, "Possible Physiological Roles of Carboxylic Ester Hydrolases", Drug Metabolism Reviews, Jan. 1987, 18(4), pp. 379-439.
Liang et al. "Fast-Dissolving Intraoral Drug Delivery Systems", Expert Opinion in Therapeutic Patents, Jun. 2001, 11(6), pp. 981-986.
Lieberman et al., Pharmaceutical Dosage Forms: Tablets, vol. 1, 1980, pp. 145-157.
Marceau et al., "Bradykinin Receptor Ligands: Therapeutic Perspectives", Nature Reviews Drug Discovery, Oct. 2004, 3, pp. 845-852.
Okada et al., "Development of Potent and Selective Plasmin and Plasma Kallikrein Inhibitors and Studies on the Structure-Activity Relationship", Chem. Pharm. Bull., Sep. 2000, 48, pp. 1964-1972.
Patel, "Combination Therapy for Age-Related Macular Degeneration", Retina, Jun. 2009, 29(6), pp. S45-S48.
Remington: Practice of the Science and Pharmacy; 19th Edition; Mack Publishing Company, 1995, 5 pages, Table of Contents Only.
Shori et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), pp. 1209-1217.
Sturzebecher et al., "Inhibition of Human Mast Cell Tryptase by Benzamidine Derivatives", Biological Chemistry Hoppe-Seyler, Oct. 1992, 373(2), p. 1025.
Sturzebecher et al., "Novel Plasma Kallikrein Inhibitors of the Benzamidine Type", Brazilian J. Med. Biol. Res, Aug. 1994, 27(8), pp. 1929-1934.
Teno et al., "Development of Active Center-Directed Plasmin and Plasma Kallikrein Inhibitors and Studies on the Structure-Inhibitory Activity Relationship", Chemical and Pharmaceutical Bulletin, Jun. 1993, 41(6), pp. 1079-1090.
Wermuth et al., Handbook of Pharmaceutical Salts: Properties, Selection and Use, 2002 vol. 24, No. 3, p. 20.
Wermuth, "The Practice of Medicinal Chemistry", 2003, 2nd Ed., pp. 561-585.
Young et al., "Small Molecule Inhibitors of Plasma Kallikrein", Bioorg. Med. Chem. Letts., Apr. 2006, 16(7), pp. 2034-2036.
International Patent Application No. PCT/GB2015/053613: International Search Report dated Jun. 2, 2016, 5 pages.
International Patent Application No. PCT/GB2015/053613: Written Opinion dated Jun. 2, 2016, 9 pages.
Zhang et al. "Discovery of Highly Potent Small Molecule Kallikrein Inhibitors" Medicinal Chemistry, 2006, 2, pp. 545-553.
Ambinter Sari: "1 H-Pyrazole-4-carboxamides" In: Chemical Catalog, 11; Sep. 2011 (Sep. 11, 2011), Ambinter SARL, XP055601375.
Babu, "Drug Discovery at BioCryst Pharmaceuticals Inc.", Presentation, http://files.shareholder.com/downloads/BCRX/0x0x403076/ 97a18d6e-1621-4fc6--8f5fd0828bddab4f/, Sep. 16, 2010, 18 pages.
Bird et al. Thrombosis and Haemostasis, Effects of plasma kallikrein deficiency on haemostasis and thrombosis in mice: Murine Ortholog of the Fletcher Trait, 2012, 107, 1141-50.
Bjorkqvist et al., "Plasma kallikrein: the bradykinin-producing enzyme", Thrombosis and Haemotasis, 2013, 110, 399-407.
Caddick et al., "Convenient Synthesis of Protected Primary Amines from Nitriles", Tetrahedron Letters, Apr. 29, 2000, 41(18), 3513-3516.
Calderone et al., "1,2,3-Triazol-Carboxanilides and 1,2,3-Triazol-(N-Benzyl)-Carboxamides as BK-Potassium Channel Activators. XII" European Journal of Medicinal Chemistry 43, 2008, pp. 2618-2626.
Cannon, Chapter Nineteen in Burger's Medicinal Chemistry and Drug Discovery, Fifth Edition, vol. I: Principles and Practice, Wiley-Interscience 1995, pp. 783-802.
CAS Extract for Compound 1086603-52-2, dated Dec. 18, 2008, 2 pages.
CAS Extract for Compound 1094996-93-6, dated Jan. 22, 2009, 1 page.
CAS Extract for Compound 1171693-25-6, dated Aug. 2, 2017, 1 page.
CAS extract for Compound 1180236-10-5; Sep. 4, 2009.
CAS extract for Compound 1180808-34-7; Sep. 6, 2009.
CAS extract for Compound 1288265-35-9; May 1, 2011.
CAS extract for Compound 1288488-40-3; May 1, 2011.
CAS extract for Compound 1288531-53-2; May 1, 2011.
CAS extract for Compound 1293757-54-6; May 12, 2011.
CAS extract for Compound 1297493-36-7; May 19, 2011.
CAS Extract for Compound 1386189-59-8, dated Aug. 3, 2012, 1 page.
CAS Structures cited in W0201683818 Written Opinion dated Jun. 2, 2016, 290 pages.
Chemical Abstract Service, CHEMCATS, RN 1424383-07-2, Mar. 15, 2013.
Chilcote et al., "ASP-634: An Oral Drug Candidate for Diabetic Macular Edema", ARVO 2012 Mar. 2012, Fort Lauderdale, Florida, Presentation, vol. 53, 2240, Abstract Only Provided.
Colman, "Plasma and tissue kallikrein in arthritis and inflammatory bowel disease", Immunopharmacology, 1999, 43, 103-108.
Davis III et al., "Biological activities of C1 inhibitor", Molecular Immunology, 2008, 45, 4057-4063.
Feener at al., "Role of plasma kallikrein in diabetes and metabolism", Thrombosis and Haemostasis, Sep. 2013, 110(3), 434-441.
Ikeda et al., "Host Stromal Bradykinin B.sub.2 Receptor Signaling Facilitates Tumor-Associated Angiogenesis and Tumor Growth", Cancer Research, Aug. 2004, 64, 5178-5185.

(56) References Cited

OTHER PUBLICATIONS

International Search Report for PCT/GB2014/051592 completed Jul. 23, 2014.
Jaffa et al., "Plasma Prekallikrein a Risk Marker for Hypertension and Nephropathy in Type 1 Diabetes", Diabetes, May 2003, vol. 52, 1215-1221.
Katsuura et al., "Effects of a Highly Selective Synthetic Inhibitor of Plasma Kallikrein on Disseminated Intravascular Coagulation in Rats" Thrombosis Research, 1996, 82, 361-368.
Kenniston, J Bio Chem, "Inhibition of Plasma Kallikrein by a Highly Specific Active Site Blocking Antibody", vol. 289 (34), 2014, 23596-23608.
Lieberman et al., Pharmaceutical Dosage Forms: Tablets, Second Edition, vol. 1, 1980; (front page and list of contents); 6 pages.
Lieberman et al., Pharmaceutical Dosage Forms: Tablets, Second Edition, vol. 2, XP008099925, 145-157, 1990.
Liu et al., Nat Med., Hyperglycemia Induced Cerebral Hematoma Expansion is Mediated by Plasma Kallikrein, 2011, 17, 206-210.
Lussis et al.; "A single synthetic small molecule that generates force against a load"; Nature Nanotechnology; vol. 6; 2011; p. 553-557.
Lussis et al.; "A single synthetic small molecule that generates force against a load"; Nature Nanotechnology; vol. 6; 2011; p. S1-S25 (Supplemental Information).
Luthin et al., "The Discovery of Novel Small Molecule Non-peptide Gonadotropin Releasing Hormone (GnRH) Receptor Antagonists" Bioorg Med Chem Lett, 12, 2002, pp. 3467-3470.
Pace, et al., "4-Hydroxy-5-pyrrolinone-3-carboxamide HIV-1 integrase inhibitors", Bioorganic & Medicinal Chemistry Letters., Jun. 18, 2008, pp. 3865-3869.
Prassas, "Unleashing the therapeutic potential of human kallikrein—related serine proteases", Nature Reviews Drug Discovery, vol. 14, 183-202, 2015.
PubChem Compound 40150888 May 30, 2009.
PubChem Compound 51143945 May 3, 2011.
PubChem Compound 52011740 May 20, 2011.
PubChem Compound 52011741 May 20, 2001.
PubChem Compound 52011742 May 20, 2011.
PubChem Compound 52011935 May 20, 2011.
PubChem Compound 52011936 May 20, 2011.
PubChem Compound 52011937 May 20, 2011.
PubChem Compound 52011938 May 20, 2011.
PubChem Compound 55389827 Jan. 25, 2012.
PubChem Compound 55408484 Jan. 25, 2012.
PubChem Compound 55408530 Jan. 25, 2012.
PubChem Compound 55408677 Jan. 25, 2012.
PubChem Compound 55408742 Jan. 25, 2012.
PubChem Compound 55408894 Jan. 25, 2012.
PubChem Compound 55438190 Jan. 25, 2012.
PubChem Compound 55494217 Jan. 25, 2012.
PubChem Compound 55650494 Jan. 25, 2012.
PubChem Compound 60376550 Oct. 18, 2012.
PubChem Compound ID 22830339 Dec. 5, 2007.
PubChem Compound ID 24488625 Feb. 29, 2008.
PubChem Compound ID 38284485 May 29, 2009.
PubChem Compound ID 38284487 May 29, 2009.
PubChem Compound ID 46438580 Jul. 23, 2010.
Registry No. 1027627-81-1, Chemical Library—FCG Group, Jun. 12, 2008, 1 page.
Registry No. 1028093-96-0, Chemical Library—FCG Group, Jun. 13, 2008, 1 page.
Registry No. 1028096-34-5, Chemical Library—FCG Group, Jun. 13, 2008, 1 page.
Registry No. 1028361-95-6, Chemical Library—FCG Group, Jun. 16, 2008, 1 page.
Registry No. 1061709-51-0, Chemical Library—FCG Group, Oct. 15, 2008, 1 page.
Registry No. 1062408-24-5, Chemical Library—FCG Group, Oct. 17, 2008, 1 page.
Registry No. 1086603-37-3, Chemical Library—AKos Consulting and Solutions GmbH, CHEMCATS, dated Dec. 18, 2008, 1 page.
Registry No. 1086603-42-0, Chemical Library—AKos Consulting and Solutions GmbH, CHEMCATS, dated Dec. 18, 2008, 1 page.
Registry No. 1086603-52-2, Chemical Library—AKos Consulting and Solutions GmbH, CHEMCATS, dated Dec. 18, 2008, 1 page.
Registry No. 1094996-93-6, Chemical Library—AKos Consulting and Solutions GmbH, CHEMCATS, dated Jan. 22, 2009, 1 page.
Registry No. 1103271-51-7, Chemical Library—FCG Group, Feb. 9, 2009, 1 page.
Registry No. 1170030-40-6, Chemical Library—FCG Group, Jul. 29, 2009, 1 page.
Registry No. 1171669-07-0, Chemical Library—FCG Group, Aug. 2, 2009, 1 page.
Registry No. 1171693-25-6, Chemical Library—Ambinter, CHEMCATS, dated Aug. 2, 2017, 1 page.
Registry No. 1278351-92-0, Chemical Library—FCG Group, Apr. 11, 2011, 1 page.
Registry No. 1280842-43-4, Chemical Library—FCG Group, Apr. 18, 2011, 1 page.
Registry No. 1317328-27-0, Chemical Library—FCG Group, Aug. 14, 2011, 1 page.
Registry No. 1317855-54-1, Chemical Library—FCG Group, Aug. 15, 2011, 1 page.
Registry No. 1318167-86-0, Chemical Library—FCG Group, CHEMCATS, dated Aug. 15, 2011, 1 page.
Registry No. 1318604-27-1, Chemical Library—FCG Group, Aug. 16, 2011, 1 page.
Registry No. 1320653-15-3, Chemical Library—FCG Group, Aug. 21, 2011, 1 page.
Registry No. 1321195-15-6, Chemical Library—FCG Group, Aug. 21, 2011, 1 page.
Registry No. 1321521-84-9, Chemical Library—FCG Group, Aug. 12, 2011, 1 page.
Registry No. 1386189-59-8, Chemical Library—Ukrorgsyntez Ltd., CHEMCATS, dated Aug. 3, 2012, 1 page.
Registry No. 1390613-03-2, Chemical Library—FCG Group, Aug. 13, 2012, 1 page.
Registry No. 1569406-35-4, Chemical Library—FCG Group, Mar. 18, 2014, 1 page.
Registry No. 1570266-44-2, Chemical Library—FCG Group, dated Mar. 19, 2014, 1 page.
Registry No. 1572436-72-6, Chemical Library—FCG Group, dated Mar. 24, 2014, 1 page.
Registry No. 1572946-10-1, Chemical Library—FCG Group, Mar. 25, 2014, 1 page.
Registry No. 1573976-69-8, Chemical Library—FCG Group, dated Mar. 26, 2014, 1 page.
Registry No. 1575116-26-5, Chemical Library—FCG Group, Mar. 28, 2014, 1 page.
Registry No. 1575214-30-0, Chemical Library—FCG Group, dated Mar. 28, 2014, 1 page.
Registry No. 1580327-09-8, Chemical Library—FCG Group, dated Apr. 4, 2014, 1 page.
Registry No. 1625594-62-8, Chemical Library—FCG Group, Sep. 24, 2014, 1 page.
Registry No. 879195-72-9, Chemical Library—FCG Group, Apr. 4, 2006, 1 page.
Registry No. 879300-81-9, Chemical Library—FCG Group, Apr. 5, 2006, 1 page.
Registry No. 955867-36-4, Chemical Library—FCG Group, Nov. 23, 2007, 1 page.
Registry No. 956190-38-8, Chemical Library—FCG Group, Nov. 28, 2007, 1 page.
Registry No. 956290-77-0, Chemical Library—FCG Group, Nov. 29, 2007, 1 page.
Registry No. 956444-80-7, Chemical Library—FCG Group, Dec. 2, 2007, 1 page.
Registry No. 956521-49-6, Chemical Library—FCG Group, Dec. 3, 2007, 1 page.
Registry No. 956529-72-9, Chemical Library—FCG Group, Dec. 3, 2007, 1 page.
Registry No. 956747-39-0, Chemical Library—FCG Group, Dec. 5, 2007, 1 page.

(56) References Cited

OTHER PUBLICATIONS

Registry No. 1015534-45-8, Chemical Library—FCG Group, Apr. 18, 2008, 1 page.
Remington's Pharmaceutical Sciences, Remington: Practice of The Science and Pharmacy; 19th Edition, Mack Publishing Company, 1995; 5 pages , Cover Page and Table of Contents Pages Only.
Revenko et al., Blood Journal, "Selective depletion of plasma prekallikrein or coagulation factor XII inhibits thrombosis in mice without increased risk of bleeding", 2011, 118, 5302-5311.
Revenko et al., Blood, Selective depletion of plasma prekallikrein or coagulation factor XII inhibits thrombosis in mice without increased risk of bleeding, 2011, 118, 5302-5311.
Siebeck et al., "Inhibition of Plasma Kallikrein With Aprotinin in Porcine Endotoxin Shock", The Journal of Trauma, 1993, vol. 34, No. 2, 193-198.
Stahl et al., "Handbook of Pharmaceutical Salts: Properties, Selection and Use", Wiley-VCH, Weinheim, Germany, 2002, 1 page.
STN Registry, "5-Pyrimidinecarboxamide, 1,6-dihydro-N-[1-(6-methyl-1H-benzimidazol-2-yl)ethyl]-2-oxo-2-(1H-1,2,4-triazol-1-ylmethyl)", CAS No. 1422635-37-7, Mar. 8, 2013.
STN Registry, "5-Pyrimidinecarboxamide, N-[1-(1 H-benzimidazol-2-yl)ethyl]-1,6-dihydro-6-oxo-2-(phenoxymethyl)", CAS No. 1434334-41-4, Jun. 5, 2013.
Tanaka et al., Thrombosis Research 2004, "Evaluation of a novel kallikrein inhibitor on hemostatic activation in vitro"; 113, 333-339.
Tanaka et al., Thrombosis Research, Evaluation of a novel kallikrein inhibitor on hemostatic activation in vitro; 2004, 113, 333-339.
Tang et al., "Expression, Crystallization, and Three-Dimensional Structure of the Catalytic Domain of Human Plasma Kallikrein" The Journal of Biological Chemistry vol. 280, No. 49, Dec. 2005, pp. 41077-41089.
Tombran-Tink et al., "Opthamology Research", Visual Dysfunction in Diabetes the Science of Patient Impairment and Health Care, 2012, 4 pages. , Cover Pages and p. 34 Only.
Ulven et al.; "6-Acylamino-2-amino-4-methylquinolines as potent melanin-concentrating hormone 1 receptor antagonists: Structure-activity exploration of eastern and western parts"; Bioorganic & Medicinal Chemistry Letters; vol. 16 Issue 4; Feb. 2006; p. 1070-1075.
Chilcote et al., "ASP-634: An Oral Drug Candidate for Diabetic Macular Edema", ARVO 2012 May 6-9, 2012, Fort Lauderdale, Florida, (Presentation 2240), 1 page.
Durairaj et al., "Prediction of Vitreal Half-Life Based on Drug Physiochemical Properties: Quantitative Structure-Pharmacokinetic Relationships (QSPKR)", Pharmaceutical Research, 2009, 26(5), 1236-1260.
Lieberman et al. Pharmaceutical Dosage Forms: Tablets, Second Edition, vol. 2, 1989, XP008099925; 15 pages (front page and list of contents included), 145-157.
Marra et al, "Solution Formulation Development of a VEGF Inhibitor for Intravitreal Injection", 2011, 12(1), 362-370.
Maurice, "Review: Practical Issues in Intravitreal Drug Delivery", Journal of Ocular Pharmacology and Therapeutics, 2001, 17(4), 393-401.
MedicineNet (2004) Web:<http://www.medterms.com>, Definition of Cancer.
Stahl and Wermuth, "Handbook of Pharmaceutical Salts: Properties, Selection and Use", Wiley-VCH, Weinheim, Germany, 2002.
Zhang et al., "Discovery of Highly Potent Small Molecule Kallikrein Inhibitors", Medicinal Chemistry, 2006, vol. 2, No. 6, 545-553.

* cited by examiner

N-((HET) ARYLMETHYL)-HETEROARYL-CARBOXAMIDES COMPOUNDS AS PLASMA KALLIKREIN INHIBITORS

CROSS-REFERENCE TO RELATED APPLICATIONS

This application is the National Stage of International Patent Application No. PCT/GB2015/053613 filed Nov. 26, 2015, which claims the benefit of Great Britain Patent Application No. 1421085.0, filed Nov. 27, 2014. The disclosures of International Patent Application No. PCT/GB2015/053613 filed Nov. 26, 2015 are incorporated herein by reference in their entireties.

This invention relates to enzyme inhibitors that are inhibitors of plasma kallikrein and to pharmaceutical compositions containing and the uses of, such inhibitors.

BACKGROUND TO THE INVENTION

The heterocyclic derivatives of the present invention are inhibitors of plasma kallikrein and have a number of therapeutic applications, particularly in the treatment of retinal vascular permeability associated with diabetic retinopathy and diabetic macular edema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., Pharmacological Rev., 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . " *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (*Brazilion J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem. Letts.* 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote ond Sukonto Sinho ("ASP-634: An Oral Drug Candidate for Diabetic MacularEdema", ARVO 2012 May 6-May 9, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites. In another report, indole amides are claimed as compounds that might overcome problems associated with drugs possessing poor or inadequate ADME-tox and physicochemical properties although no inhibition against plasma kallikrein is presented or claimed (Griffioen et al, "Indole amide derivatives and related compounds for use in the treatment of neurodegenerative diseases", WO2010, 142801).

BioCryst Pharmaceuticals Inc. have reported the discovery of the orally available plasma kallikrein inhibitor BCX4161 ("BCX4161, An Oral Kallikrein Inhibitor: Safety and Pharmacokinetic Results Of a Phase 1 Study In Healthy Volunteers", Journal of Allergy and Clinical Immunology, Volume 133, Issue 2, Supplement, February 2014, page AB39 and "A Simple, Sensitive and Selective Fluorogenic Assay to Monitor Plasma Kallikrein Inhibitory Activity of BCX4161 in Activated Plasma", Journal of Allergy and Clinical Immunology, Volume 133, Issue 2, Supplement February 2014, page AB40). However, human doses are relatively large, currently being tested in proof of concept studies at doses of 400 mg three times daily.

There are only few reports of plasma kallikrein inhibitors that do not feature guanidine or amidine functionalities. One example is Brandl et al. ("N-((6-amino-pyridin-3-yl) methyl)-heteroaryl-carboxamides as inhibitors of plasma kallikrein" WO2012/017020), which describes compounds that feature an amino-pyridine functionality. Oral efficacy in a rat model is demonstrated at relatively high doses of 30 mg/kg and 100 mg/kg but the pharmacokinetic profile is not reported. Thus it is not yet known whether such compounds will provide sufficient oral availability or efficacy for progression to the clinic. Other examples are Brandl et al. ("Aminopyridine derivatives as plasma kallikrein inhibitors" WO2013/111107) and Flohr et al. ("5-membered heteroarylcarboxamide derivatives as plasma kallikrein inhibitors" WO2013/111108). However, neither of these documents report any in vivo data and therefore it is not yet known whether such compounds will provide sufficient oral availability or efficacy for progression to the clinic. Another example is Allen et al. "Benzylamine derivatives" WO2014/108679.

Therefore there remains a need to develop new plasma kallikrein inhibitors that will have utility to treat a wide range of disorders, in particular to reduce retinal vascular permeability associated with diabetic retinopathy and diabetic macular edema. Preferred compounds will possess a good pharmacokinetic profile and in particular will be suitable as drugs for oral delivery.

SUMMARY OF THE INVENTION

The present invention relates to a series of heterocyclic derivatives that are inhibitors of plasma kallikrein. These compounds demonstrate good selectivity for plasma kallikrein and are potentially useful in the treatment of impaired visual acuity, diabetic retinopathy, macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery. The invention further relates to pharmaceutical compositions of the inhibitors, to the use of the compositions as therapeutic agents, and to methods of treatment using these compositions.

In a first aspect, the present invention provides compounds of formula I

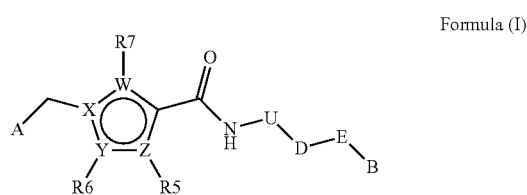

Formula (I)

wherein

B is $(CH_2)_n$phenyl, wherein n is 0 or 1 and phenyl is substituted with 1 to 3 substituents selected from alkyl, alkoxy, OH, halo, CN, COOR8, CONR8R9, $OCF_3$, $CF_3$ and NR8R9;

or B is 5 or 6 membered heterocyclic ring containing one or two heteroatoms selected from N, O and S; said heterocyclic ring may be aromatic or non-aromatic and is substituted with 1 to 3 substituents selected from alkyl, alkoxy, OH, oxo, halo, CN, COOR8, CONR8R9, $OCF_3$, $CF_3$ and NR8R9;

D is selected from $CH_2$, $CHalkyl^b$, $C(alkyl^b)_2$ and CO; and either:

U is selected from $CH_2$, $CHalkyl^b$ and $C(alkyl^b)_2$; and

E is selected from NH, $Nalkyl^b$, $CH_2$ and 0;

or

U is CH; and

E is N;

wherein U, D and E together form part of an azacarbocycle;

W, X, Y and Z are independently selected from C, N, O and S, such that the ring containing W, X, Y and Z is a five membered aromatic heterocycle;

R5, R6 and R7 are independently absent or independently selected from H, alkyl, alkoxy, halo, OH, aryl, heteroaryl, —NR8R9, CN, COOR8, CONR8R9, —NR8COR9, $CF_3$, and R16;

A is selected from aryl and heteroaryl;

R8 and R9 are independently selected from H and alkyl;

R16 is a carbon-containing 3-, 4-, 5- or 6-membered monocyclic ring system which may be aromatic, saturated or unsaturated non-aromatic and which may optionally contain 1, 2, 3 or 4 heteroatoms selected from N, O and S, wherein the ring system R16 is in turn optionally substituted with substituents selected from alkyl and oxo;

alkyl is a linear saturated hydrocarbon having up to 10 carbon atoms ($C_1$-$C_{10}$) or a branched saturated hydrocarbon of between 3 and 10 carbon atoms ($C_3$-$C_{10}$); alkyl may optionally be substituted with 1 or 2 substituents independently selected from ($C_1$-$C_6$)alkoxy, OH, CN, $CF_3$, COOR10, CONR10R11, fluoro and NR10R11;

$alkyl^b$ is a linear saturated hydrocarbon having up to 6 carbon atoms ($C_1$-$C_6$) or a branched saturated hydrocarbon of between 3 and 6 carbon atoms ($C_3$-$C_6$); $alkyl^b$ may optionally be substituted with 1 or 2 substituents independently selected from (C$_1$-C$_6$)alkoxy, OH, CN, CF$_3$ and fluoro;
alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy may optionally be substituted with 1 or 2 substituents independently selected from OH, CN, CF$_3$, COOR10, CONR10R11, fluoro and NR10R11;
azacarbocycle is a 5- or 6-membered mono-cyclic carbon-containing ring, which comprises one or two nitrogen atoms in the ring, and which may optionally be substituted by oxo;
aryl is phenyl, biphenyl or naphthyl; aryl may be optionally substituted with 1, 2 or 3 substituents independently selected from alkyl, alkoxy, methylenedioxy, ethylenedioxy, OH, OCF$_3$, halo, CN, heteroaryl, —(CH$_2$)$_{0-3}$—O-heteroaryl, aryl$^b$, —O-aryl$^b$, —(CH$_2$)$_{1-3}$-aryl$^b$, —(CH$_2$)$_{1-3}$-heteroaryl, —COOR10, —CONR10R11, —(CH$_2$)$_{0-3}$—NR10R11 and CF$_3$;
aryl$^b$ is phenyl, biphenyl or naphthyl, which may be optionally substituted with 1, 2 or 3 substituents independently selected from alkyl, alkoxy, OH, halo, CN, —COOR10, —CONR10R11, CF$_3$ and NR10R11;
heteroaryl is a 5, 6, 9 or 10 membered mono- or bi-cyclic aromatic ring, containing, where possible, 1, 2 or 3 ring members independently selected from N, NR8, S and O; heteroaryl may be optionally substituted with 1, 2 or 3 substituents independently selected from alkyl, alkoxy, OH, OCF$_3$, halo, CN, aryl, —(CH$_2$)$_{1-3}$-aryl, heteroaryl$^b$, —COOR10, —CONR10R11, CF$_3$ and —(CH$_2$)$_{0-3}$—NR10R11;
heteroaryl$^b$ is a 5, 6, 9 or 10 membered mono- or bi-cyclic aromatic ring, containing, where possible, 1, 2 or 3 ring members independently selected from N, NR8, S and O; wherein heteroaryl$^b$ may be optionally substituted with 1, 2 or 3 substituents independently selected from alkyl, alkoxy, OH, halo, CN, aryl, —(CH$_2$)$_{1-3}$-aryl, —COOR10, —CONR10R11, CF$_3$ and NR10R11;
R10 and R11 are independently selected from H, alkyl$^b$, CONR14R15, COR17, aryl$^b$ and heteroaryl$^b$; or R10 and R11 together with the nitrogen atom to which they are attached form a carbon-containing 4-, 5-, 6- or 7-membered heterocyclic ring, optionally containing an additional heteroatom selected from N, S and O, which may be saturated or unsaturated with 1 or 2 double bonds and which may be optionally mono- or di-substituted with substituents selected from oxo, alkyl$^b$, alkoxy, OH, halo and CF$_3$;
R14, R15 and R17 are independently selected from H or alkyl$^b$;
and tautomers, isomers, stereoisomers (including enantiomers, diastereoisomers and racemic and scalemic mixtures thereof), pharmaceutically acceptable salts and solvates thereof, with the proviso that the compound of formula (I) is not

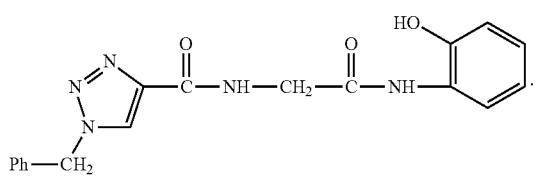

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

In a further aspect, also provided are compounds of formula (I), wherein:
B is selected from phenyl and pyridyl, each substituted with 1 to 3 substituents selected from alkyl, alkoxy, OH, halo, CN, COOR8, CONR8R9, OCF$_3$, CF$_3$ and NR8R9;
U is CH$_2$;
D is selected from CH$_2$ and CO;
E is selected from NH, CH$_2$ and O;
W is C and X, Y and Z are independently selected from C and N, such that the ring containing W, X, Y and Z is a five membered aromatic heterocycle;
R5 and R6 are independently absent or independently selected from H, alkyl, R16, NR8R9 and CF$_3$; wherein at least one of R5 and R6 is present and is not H;
R7 is selected from H, alkyl, R16, NR8R9 and CF$_3$;
A is selected from

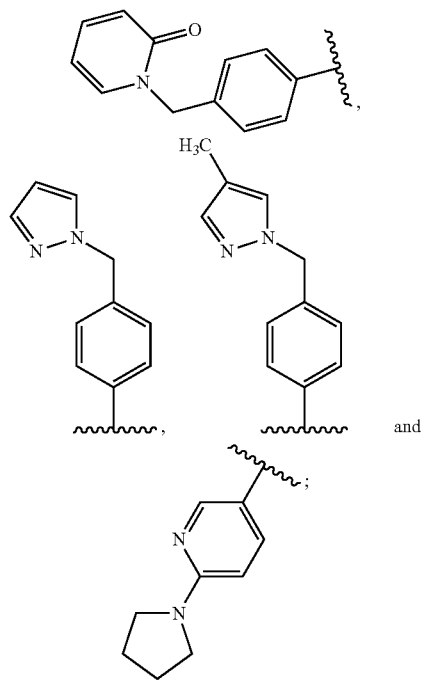

alkyl, alkoxy, R8 and R9 are as defined above;
R16 is cycloalkyl;
cycloalkyl is a monocyclic saturated hydrocarbon of between 3 and 5 carbon atoms;
and tautomers, isomers, stereoisomers (including enantiomers, diastereoisomers and racemic and scalemic mixtures thereof), pharmaceutically acceptable salts and solvates thereof.

In a further aspect, also provided are compounds of formula (I), wherein:
B is selected from phenyl and pyridyl, each substituted with 1 to 3 substituents selected from alkyl$^b$, alkoxy, OH, halo, CN, COOR8, CONR8R9, OCF$_3$, and CF$_3$;
U is CH$_2$;

D is selected from CH$_2$ and CHalkyl$^b$;
E is selected from NH, CH$_2$ and O;
W is C and X, Y and Z are independently selected from C and N, such that the ring containing W, X, Y and Z is a five membered aromatic heterocycle;
R5 and R6 are independently absent or independently selected from H, alkyl, R16, NR8R9 and CF$_3$; wherein at least one of R5 and R6 is present and is not H;
R7 is selected from H, alkyl, R16, NR8R9 and CF$_3$;
A is selected from

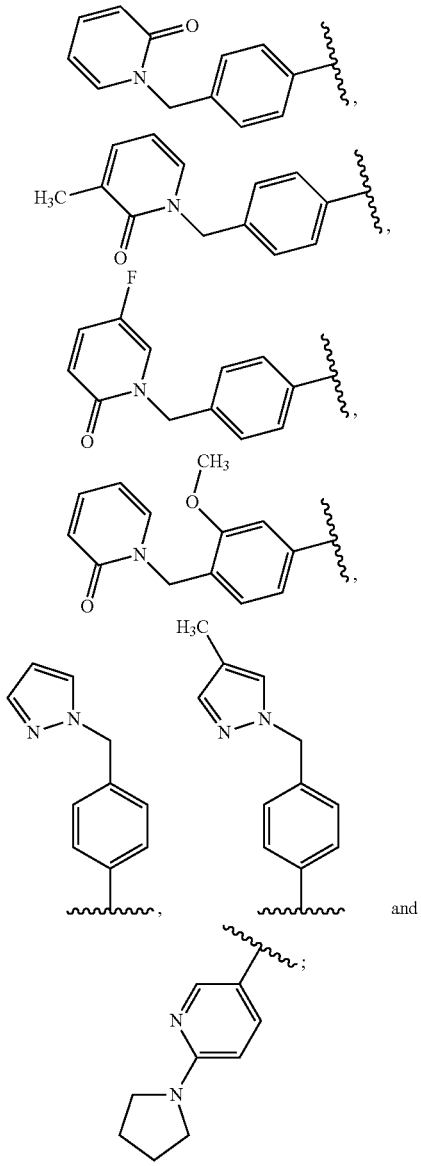

wherein,
alkyl, alkyl$^b$, alkoxy, R8 and R9 are as defined above;
R16 is cycloalkyl;
cycloalkyl is a monocyclic saturated hydrocarbon of between 3 and 5 carbon atoms;
and tautomers, isomers, stereoisomers (including enantiomers, diastereoisomers and racemic and scalemic mixtures thereof), pharmaceutically acceptable salts and solvates thereof.

The aspects of the invention described above may also comprise the following features:

B is (CH$_2$)$_n$phenyl, wherein n is 0 or 1 and phenyl is substituted with 1 to 3 substituents selected from alkyl, alkoxy, OH, halo, CN, COOR8, CONR8R9, OCF$_3$, CF$_3$ and NR8R9; or B is 5 or 6 membered heterocyclic ring containing one or two heteroatoms selected from N, O and S; said heterocyclic ring may be aromatic or non-aromatic and is substituted with 1 to 3 substituents selected from alkyl, alkoxy, OH, oxo, halo, CN, COOR8, CONR8R9, OCF$_3$, CF$_3$ and NR8R9; wherein alkyl, alkoxy, R8 and R9 are as defined above.

B is (CH$_2$)$_n$phenyl, wherein n is 0 or 1 and phenyl is substituted with 1 to 3 substituents selected from alkyl, alkoxy, halo, CN, COOR8, CONR8R9, OCF$_3$, CF$_3$ and NR8R9; or B is 5 or 6 membered heterocyclic ring containing one or two heteroatoms selected from N, O and S; said heterocyclic ring may be aromatic or non-aromatic and is substituted with 1 to 3 substituents selected from alkyl, alkoxy, OH, oxo, halo, CN, COOR8, CONR8R9, OCF$_3$, CF$_3$ and NR8R9; wherein alkyl, alkoxy, R8 and R9 are as defined above.

B is (CH$_2$)$_n$phenyl, wherein n is 0 or 1 and phenyl is substituted with 1 to 3 substituents selected from alkyl$^b$, alkoxy, OH, halo, CN, COOR8, CONR8R9, OCF$_3$ and CF$_3$; or B is 5 or 6 membered heterocyclic ring containing one or two heteroatoms selected from N, O and S; said heterocyclic ring may be aromatic or non-aromatic and is substituted with 1 to 3 substituents selected from alkyl$^b$, alkoxy, OH, oxo, halo, CN, COOR8, CONR8R9, OCF$_3$ and CF$_3$; wherein alkyl$^b$, alkoxy, R8 and R9 are as defined above.

B is phenyl substituted with 1 to 3 substituents selected from alkyl, alkoxy, OH, halo, CN, COOR8, CONR8R9, OCF$_3$, CF$_3$ and NR8R9; or B is 5 or 6 membered heterocyclic ring containing one or two heteroatoms selected from N, O and S; said heterocyclic ring may be aromatic or non-aromatic and is substituted with 1 to 3 substituents selected from alkyl, alkoxy, OH, oxo, halo, CN, COOR8, CONR8R9, OCF$_3$, CF$_3$ and NR8R9; wherein alkyl, alkoxy, R8 and R9 are as defined above.

B is selected from phenyl, pyridyl, pyrimidone, pyrimidine, thiazolyl, isothiazolyl, pyrazolyl, imidazolyl, isoxazolyl, oxazolyl, pyrrolyl, thiophenyl and furanyl, each substituted, when possible, with 1 to 3 substituents selected from alkyl, alkoxy, OH, oxo, halo, CN, COOR8, CONR8R9, OCF$_3$, CF$_3$ and NR8R9; wherein alkyl, alkoxy, R8 and R9 are as defined above.

B is selected from phenyl, pyridyl, pyrimidone, pyrimidine, thiazolyl, isothiazolyl, pyrazolyl, imidazolyl, isoxazolyl, oxazolyl, pyrrolyl, thiophenyl and furanyl, each substituted with a Cl substituent and, optionally, when possible, with 1 or 2 additional substituents selected from alkyl, alkoxy, OH, oxo, halo, CN, COOR8, CONR8R9, OCF$_3$, CF$_3$ and NR8R9; wherein alkyl, alkoxy, R8 and R9 are as defined above.

B is selected from phenyl, pyridyl, pyrimidone, thiazolyl, pyrazolyl, isoxazolyl, thiophenyl and furanyl, each substituted, when possible, with 1 to 3 substituents selected from alkyl, alkoxy, OH, oxo, halo, CN, COOR8, CONR8R9, OCF$_3$, CF$_3$ and NR8R9; wherein alkyl, alkoxy, R8 and R9 are as defined above.

B is selected from phenyl and pyridyl, each substituted with 1 to 3 substituents selected from alkyl, alkoxy, OH, halo, CN, COOR8, CONR8R9, OCF$_3$, CF$_3$ and NR8R9; wherein alkyl, alkoxy, R8 and R9 are as defined above.

B is selected from phenyl and pyridyl, each substituted with 1 to 3 substituents selected from alkyl, alkoxy and halo; wherein alkyl and alkoxy are as defined above.

B is selected from phenyl and pyridyl, each substituted with 1 to 3 substituents selected from alkyl$^b$, alkoxy and halo; wherein alkyl$^b$ and alkoxy are as defined above.

B is selected from phenyl and pyridyl, each substituted with 1 to 3 substituents selected from methyl, ethyl, methoxy, ethoxy, Cl and F.

B is selected from phenyl substituted with 1 to 3 substituents selected from methyl, ethyl, methoxy, ethoxy, Cl and F.

B is selected from phenyl substituted with Cl, wherein said phenyl is optionally substituted with 1 or 2 additional substituents selected from methyl, ethyl, methoxy, ethoxy, Cl and F.

B is

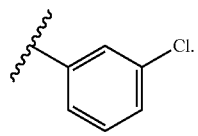 [SMILES: *c1cccc(Cl)c1]

D is selected from CH$_2$, CHalkyl$^b$, C(alkyl$^b$)$_2$ and CO; wherein alkyl$^b$ is as defined above.

D is selected from CH$_2$ and CHalkyl$^b$; wherein alkyl$^b$ is as defined above.

U is selected from CH$_2$, CHalkyl$^b$ and C(alkyl$^b$)$_2$; wherein alkyl$^b$ is as defined above.

U is CH$_2$.

E is selected from NH, Nalkyl$^b$, CH$_2$ and 0; wherein alkyl$^b$ is as defined above.

E is selected from NH, CH$_2$ and O.

U is CH, E is N and U, D and E together form part of an azacarbocycle; wherein azacarbocycle is as defined above.

D is selected from CH$_2$ and CO; E is selected from NH, CH$_2$ and O.

D is selected from CH$_2$ and CO and E is selected from NH, CH$_2$, S and O.

D is CH$_2$ or CHalkyl$^b$, and E is O; wherein alkyl$^b$ is as defined above.

D is CH$_2$ or CHMe, and E is O.

D is CO and E is NH.

D is CH$_2$ and E is CH$_2$.

D is CH$_2$ and E is O.

W, X, Y and Z are independently selected from C, N, O and S, such that the ring containing W, X, Y and Z is a five membered aromatic heterocycle.

W, X, Y and Z are independently selected from C and N, such that the ring containing W, X, Y and Z is a five membered aromatic heterocycle.

W is C and X, Y and Z are independently selected from C and N, such that the ring containing W, X, Y and Z is a five membered aromatic heterocycle.

W, X, Y and Z are independently selected from C and N, such that the ring containing W, X, Y and Z is selected from pyrrole, pyrazole, imidazole, 1,2,3-triazole and 1,2,4-triazole.

W, X, Y and Z are independently selected from C and N, such that the ring containing W, X, Y and Z is selected from pyrazole and imidazole.

W is C.

X is N.

W is C, X is N and Y and Z are selected from C and N.

W is C, X is N, Y is N and Z is C.

W is C, X is N, Y is C and Z is N.

R5, R6 and R7 are independently absent or independently selected from H, alkyl, alkoxy, halo, OH, aryl, heteroaryl, —NR8R9, CN, COOR8, CONR8R9, —NR8COR9, CF$_3$, and R16; wherein R8, R9 and R16 are as defined above.

R7 is H and R5 and R6 are independently absent or independently selected from H, alkyl, alkoxy, halo, OH, aryl, heteroaryl, —NR8R9, CN, COOR8, CONR8R9, —NR8COR9, CF$_3$, and R16; wherein R8, R9 and R16 are as defined above.

At least one of R5, R6 and R7 is present and is independently selected from alkyl, alkoxy, halo, OH, aryl, heteroaryl, —NR8R9, CN, COOR8, CONR8R9, —NR8COR9, CF$_3$, and R16; wherein R8, R9 and R16 are as defined above.

R5, R6 and R7 are independently absent or independently selected from H, alkyl, R16, alkoxy, —NR8R9 and CF$_3$; wherein R16 is cycloalkyl wherein cycloalkyl is a monocyclic saturated hydrocarbon of between 3 and 7 carbon atoms.

R5, R6 and R7 are independently absent or independently selected from H, alkyl, R16, NR8R9 and CF$_3$; wherein R8 and R9 are H; R16 is cycloalkyl wherein cycloalkyl is a monocyclic saturated hydrocarbon of between 3 and 7 carbon atoms; and, optionally, wherein at least one of R5 and R6 is present and is not H.

R5 and R6 are independently absent or independently selected from H, alkyl, R16, alkoxy, CN, NR8R9 and CF$_3$; wherein R16 is cycloalkyl and cycloalkyl is a monocyclic saturated hydrocarbon of between 3 and 6 carbon atoms.

R7 is selected from H, alkyl, alkoxy, NH$_2$ and CF$_3$; wherein alkyl and alkoxy are as defined above.

R7 is H and R5 and R6 are independently absent or independently selected from H, alkyl, R16, NR8R9, CN and CF$_3$; wherein R8 and R9 are H; and R16 is cycloalkyl wherein cycloalkyl is a monocyclic saturated hydrocarbon of between 3 and 5 carbon atoms.

R7 is H and R5 and R6 are independently absent or independently selected from H, methyl, CH$_2$OCH$_3$, R16, NH$_2$ and CF$_3$; wherein R16 is cyclopropyl; and wherein at least one of R5 and R6 is present and is not H.

R7 is H, R6 is absent and R5 is selected from methyl, CH$_2$OCH$_3$, R16, NH$_2$ and CF$_3$; wherein R16 is cyclopropyl.

R7 is H, R6 is absent and R5 is CH$_2$OCH$_3$.

R7 is H, R6 is absent and R5 is NH$_2$.

R16 is a carbon-containing 3-, 4-, 5- or 6-membered monocyclic ring system which may be aromatic, saturated or unsaturated non-aromatic and which may optionally contain 1, 2, 3 or 4 heteroatoms selected from N, O and S, wherein the ring system R16 is in turn optionally substituted with substituents selected from alkyl and oxo.

R16 is a carbon-containing 3-, 4-, 5- or 6-membered monocyclic ring system which may be aromatic, saturated or unsaturated non-aromatic and which may optionally contain 1 or 2 heteroatoms selected from N, O and S, wherein the ring system R16 is in turn optionally substituted with substituents selected from methyl, ethyl and oxo.

R16 is cycloalkyl, wherein cycloalkyl is a monocyclic saturated hydrocarbon of between 3 and 7 carbon atoms.

R16 is selected from oxazole, thiophene, cyclopropyl, cyclobutyl, pyrrolidinyl and morpholinyl, each optionally substituted with substituents selected from methyl and oxo.

R16 is selected from cyclopropyl, cyclobutyl and cyclopentyl.

R16 is cyclopropyl.

W is C, X is N, Y and Z are selected from C and N, R7 is H and R5 and R6 are independently absent or independently selected from H, alkyl, R16, NR8R9 and $CF_3$; wherein R8 and R9 are H and R16 is cycloalkyl, wherein and cycloalkyl is a monocyclic saturated hydrocarbon of between 3 and 7 carbon atoms.

W is C, X is N, Y is C, Z is N, R7 is H, R5 is absent and R6 is selected from methyl, $CH_2OCH_3$, R16, $NH_2$ and $CF_3$; wherein R16 is cyclopropyl.

W is C, X is N, Y is N, Z is C, R7 is H, R6 is absent and R5 is selected from methyl, $CH_2OCH_3$, R16, $NH_2$ and $CF_3$; wherein R16 is cyclopropyl.

A is selected from aryl and heteroaryl, each optionally substituted as described above.

A is selected from aryl and heteroaryl, each substituted as described above.

A is selected from phenyl, pyridyl, pyrimidonyl, thiazolyl, isothiazolyl, pyrazolyl, isoxazolyl, oxazolyl, thiophenyl, furanyl, each substituted with 1, 2 or 3 substituents independently selected from alkyl, alkoxy, halo, CN, $aryl^b$, $—(CH_2)_{1-3}-aryl^b$, $—(CH_2)_{1-3}$-heteroaryl, $—(CH_2)_{0-3}—NR10R11$ and $CF_3$; wherein alkyl, alkoxy, heteroaryl, $aryl^b$, R10 and R11 are as defined above.

A is selected from phenyl, pyrimidonyl and pyridyl each substituted with 1, 2 or 3 substituents independently selected from alkyl, alkoxy, halo, CN, $aryl^b$, $—(CH_2)_{1-3}-aryl^b$, $—(CH_2)_{1-3}$-heteroaryl, $CF_3$ and $—(CH_2)_{0-3}—NR10R11$; wherein alkyl, alkoxy, heteroaryl, $aryl^b$, R10 and R11 are as defined above.

A is selected from phenyl and pyridyl each substituted with 1, 2 or 3 substituents independently selected from alkyl, alkoxy, halo, CN, $aryl^b$, $—(CH_2)_{1-3}-aryl^b$, $—(CH_2)_{1-3}$-heteroaryl, $CF_3$ and $—(CH_2)_{0-3}—NR10R11$; wherein alkyl, alkoxy, heteroaryl, $aryl^b$, R10 and R11 are as defined above.

A is pyridyl, substituted with 1, 2 or 3 substituents independently selected from alkyl, alkoxy, halo, CN, $aryl^b$, $heteroaryl^b$, $CF_3$ and $—NR10R11$; wherein alkyl, alkoxy, $aryl^b$, R10 and R11 are as defined above.

A is pyridyl substituted with $heteroaryl^b$ or $—NR10R11$ and, optionally, 1 or 2 additional substituents independently selected from alkyl, halo and $CF_3$; wherein alkyl, $heteroaryl^b$, R10 and R11 are as defined above.

A is pyrimidonyl substituted with $heteroaryl^b$ or $—NR10R11$ and, optionally, 1 or 2 additional substituents independently selected from alkyl, halo and $CF_3$; wherein alkyl, $heteroaryl^b$, R10 and R11 are as defined above.

A is phenyl substituted with 1, 2 or 3 substituents independently selected from alkyl, alkoxy, halo, $—(CH_2)_{1-3}-aryl^b$, $—(CH_2)_{1-3}$-heteroaryl, $CF_3$ and $—(CH_2)_{1-3}—NR10R11$; wherein alkyl, alkoxy, heteroaryl, $aryl^b$, R10 and R11 are as defined above.

A is phenyl substituted with 1, 2 or 3 substituents independently selected from alkyl, halo, $—(CH_2)_{1-3}$-heteroaryl, $CF_3$ and $—(CH_2)_{1-3}—NR10R11$; wherein alkyl, heteroaryl, R10 and R11 are as defined above.

A is phenyl substituted with $—(CH_2)_{1-3}$-heteroaryl or $—(CH_2)_{1-3}—NR10R11$ and, optionally, 1 or 2 additional substituents independently selected from alkyl, alkoxy, halo and $CF_3$; wherein alkyl, heteroaryl, R10 and R11 are as defined above.

A is phenyl substituted with $—(CH_2)_{1-3}$-heteroaryl or $—(CH_2)_{1-3}—NR10R11$ and, optionally, 1 or 2 additional substituents independently selected from alkyl, halo and $CF_3$; wherein alkyl, heteroaryl, R10 and R11 are as defined above.

A is phenyl substituted with $—(CH_2)_{1-3}—NR10R11$ and, optionally, 1 or 2 additional substituents independently selected from alkyl, alkoxy, halo and $CF_3$; wherein alkyl, alkoxy, heteroaryl, R10 and R11 are as defined above.

A is selected from:

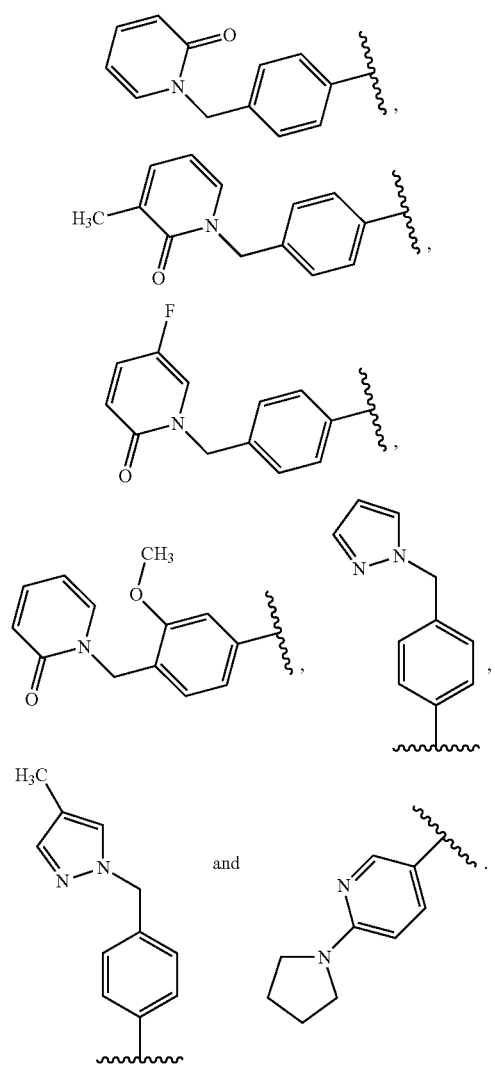

A is selected from:

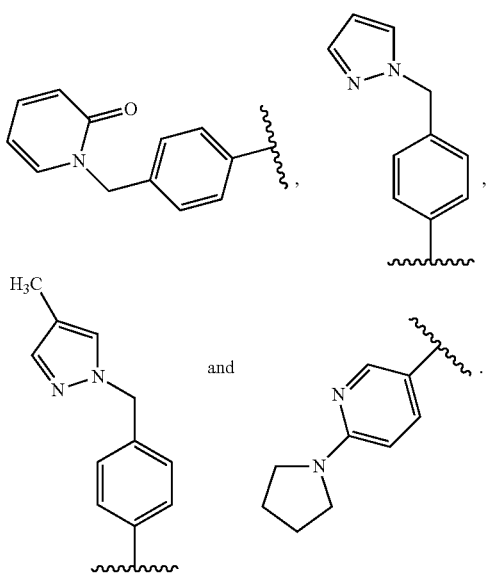

A is selected from:

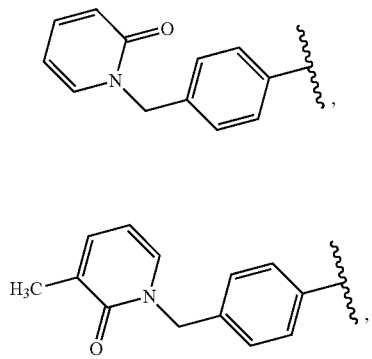

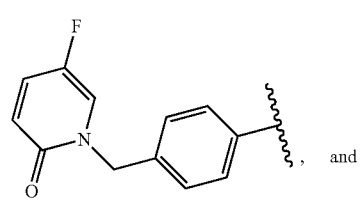

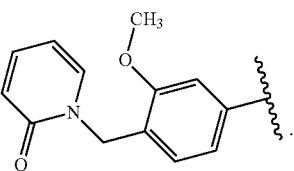

A is selected from:

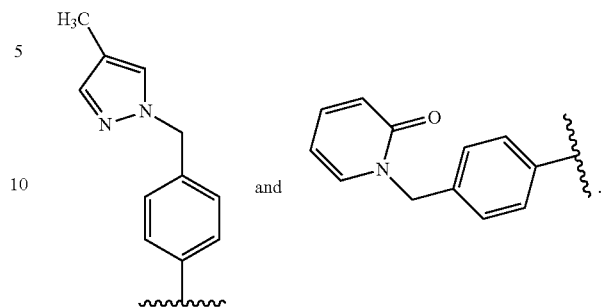

R8 and R9 are independently selected from H and alkyl.
R8 and R9 are independently selected from H and methyl, ethyl, n-propyl and isopropyl.
R8 and R9 are independently selected from H and methyl.
NR10R11 is

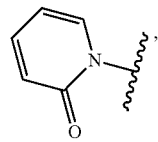

optionally mono-substituted with a substituent selected from oxo, alkyl, alkoxy, OH, halo and $CF_3$.

R10 and R11 are independently selected from H, $alkyl^b$, $aryl^b$ and $heteroaryl^b$; or R10 and R11 together with the nitrogen atom to which they are attached form a carbon-containing 4-, 5-, 6- or 7-membered heterocylic ring, optionally containing an additional heteroatom selected from N, S and O, which may be saturated or unsaturated with 1 or 2 double bonds and which may be optionally mono- or di-substituted with substituents selected from oxo, $alkyl^b$, alkoxy, OH, halo and $CF_3$; wherein $alkyl^b$, alkoxy, $aryl^b$ and $heteroaryl^b$ are as defined above.

R10 and R11 are independently selected from H and alkyl or R10 and R11 together with the nitrogen atom to which they are attached form a carbon-containing 4-, 5-, 6- or 7-membered heterocylic ring which may be saturated or unsaturated with 1 or 2 double bonds and which may be optionally mono- or di-substituted with substituents selected from oxo, $alkyl^b$, alkoxy, OH, F and $CF_3$; wherein $alkyl^b$ and alkoxy are as defined above.

R10 and R11 are independently selected from H and alkyl or R10 and R11 together with the nitrogen atom to which they are attached form a carbon-containing 5- or 6-membered heterocylic ring which may be saturated or unsaturated with 1 or 2 double bonds and which may be optionally mono- or di-substituted with substituents selected from oxo, $alkyl^b$, alkoxy, OH, F and $CF_3$; wherein $alkyl^b$ and alkoxy are as defined above.

R10 and R11 are independently selected from H and $alkyl^b$ or R10 and R11 together with the nitrogen atom to which they are attached form a 5- or 6-membered carbon containing heterocylic ring which may be saturated or unsaturated with 1 or 2 double bonds, and optionally may be substituted with oxo, F, methyl or methoxy; wherein $alkyl^b$ is as defined above.

R10 and R11 together with the nitrogen atom to which they are attached form a 6-membered carbon containing heterocylic ring which may be saturated or unsaturated with 1 or 2 double bonds, and optionally may be oxo substituted.

R10 and R11 together with the nitrogen atom to which they are attached form a carbon-containing 5- or 6-membered saturated heterocyclic ring.

R10 and R11 are independently selected from H and $C_{1-6}$alkyl; wherein $C_{1-6}$alkyl is as defined above.

R14 and R15 are independently selected from H and alkyl[b].

R14 and R15 are independently selected from H and methyl, ethyl, n-propyl and isopropyl.

R14 and R15 are independently selected from H and methyl.

R14 and R15 are methyl.

R17 is selected from H and alkyl[b].

R17 is selected from H and methyl, ethyl, n-propyl and isopropyl.

R17 is selected from methyl, ethyl, n-propyl and isopropyl.

R17 is isopropyl.

The present invention also encompasses, but is not limited to, the compounds listed below:

3-amino-1-[4-(2-oxo-2H-pyridin-1-ylmethyl)-benzyl]-1H-pyrazole-4-carboxylic acid [2-(3-chloro-phenoxy)-ethyl]-amide;

3-amino-1-[4-(2-oxo-2H-pyridin-1-ylmethyl)-benzyl]-1H-pyrazole-4-carboxylic acid [(3-chloro-phenylcarbamoyl)-methyl]-amide];

2-{[3-amino-1-({4-[(2-oxopyridin-1-yl)methyl]phenyl}methyl)pyrazol-4-yl]formamido}-N-(2-chlorophenyl)acetamide;

2-{[3-amino-1-({4-[(2-oxopyridin-1-yl)methyl]phenyl}methyl)pyrazol-4-yl]formamido}-N-(4-chlorophenyl)acetamide;

N-[2-(3-chlorophenoxy)ethyl]-3-cyclopropyl-1-({4-[(2-oxopyridin-1-yl)methyl]phenyl}methyl)pyrazole-4-carboxamide;

N-[2-(2-chlorophenoxy)ethyl]-3-(methoxymethyl)-1-({4-[(2-oxopyridin-1-yl)methyl]phenyl}methyl)pyrazole-4-carboxamide;

N-[2-(3-chlorophenoxy)ethyl]-1-({4-[(2-oxopyridin-1-yl)methyl]phenyl}methyl)-3-(trifluoromethyl)pyrazole-4-carboxamide;

N-[2-(3-chlorophenoxy)ethyl]-3-(methoxymethyl)-1-({4-[(2-oxopyridin-1-yl)methyl]phenyl}methyl)pyrazole-4-carboxamide;

N-[2-(5-chloro-2-fluorophenoxy)ethyl]-3-(methoxymethyl)-1-({4-[(2-oxopyridin-1-yl)methyl]phenyl}methyl)pyrazole-4-carboxamide;

N-[2-(3-chloro-5-fluorophenoxy)ethyl]-3-(methoxymethyl)-1-({4-[(2-oxopyridin-1-yl)methyl]phenyl}methyl)pyrazole-4-carboxamide;

N-[2-(3-chloro-5-methoxyphenoxy)ethyl-3-(methoxymethyl)-1-({4-(2-oxopyridin-1-yl)methyl]phenyl}methyl)pyrazole-4-carboxamide;

N-[2-(3-chloro-4-fluorophenoxy)ethyl]-3-(methoxymethyl)-1-({4-[(2-oxopyridin-1-yl)methyl]phenyl}methyl)pyrazole-4-carboxamide;

3-amino-N-[2-(5-chloro-2-methylphenoxy)ethyl]-1-({4-[(2-oxopyridin-1-yl)methyl]phenyl}methyl)pyrazole-4-carboxamide;

3-amino-N-[2-(3-chloro-4-methylphenoxy)ethyl]-1-({4-[(2-oxopyridin-1-yl)methyl]phenyl}methyl)pyrazole-4-carboxamide;

3-amino-N-[2-(2,3-dichlorophenoxy)ethyl]-1-({4-[(2-oxopyridin-1-yl)methyl]phenyl}methyl)pyrazole-4-carboxamide;

3-amino-N-[2-(3,4-dichlorophenoxy)ethyl]-1-({4-[(2-oxopyridin-1-yl)methyl]phenyl}methyl)pyrazole-4-carboxamide;

3-amino-N-[2-(3,5-dichlorophenoxy)ethyl]-1-({4-[(2-oxopyridin-1-yl)methyl]phenyl}methyl)pyrazole-4-carboxamide;

3-amino-N-[2-(5-chloro-2-cyanophenoxy)ethyl]-1-({4-[(2-oxopyridin-1-yl)methyl]phenyl}methyl)pyrazole-4-carboxamide;

3-amino-N-[2-(3-chloro-5-methylphenoxy)ethyl]-1-({4-[(2-oxopyridin-1-yl)methyl]phenyl}methyl)pyrazole-4-carboxamide;

3-amino-N-[2-(2,5-dichlorophenoxy)ethyl]-1-({4-[(2-oxopyridin-1-yl)methyl]phenyl}methyl)pyrazole-4-carboxamide;

N-[2-(3-chlorophenoxy)ethyl]-3-(dimethylamino)-1-({4-[(2-oxopyridin-1-yl)methyl]phenyl}methyl)pyrazole-4-carboxamide;

N-[2-(3-chlorophenoxy)ethyl]-1-({4-[(2-oxopyridin-1-yl)methyl]phenyl}methyl)pyrazole-4-carboxamide;

N-[2-(3-chlorophenoxy)ethyl]-3-(methylamino)-1-({4-[(2-oxopyridin-1-yl)methyl]phenyl}methyl)pyrazole-4-carboxamide;

N-[2-(3-chlorophenoxy)ethyl]-3-cyano-1-({4-[(2-oxopyridin-1-yl)methyl]phenyl}methyl)pyrazole-4-carboxamide;

N-[2-(3-chlorophenoxy)ethyl]-3-methyl-1-({4-[(2-oxopyridin-1-yl)methyl]phenyl}methyl)pyrazole-4-carboxamide;

2-{[3-amino-1-({4-[(2-oxopyridin-1-yl)methyl]phenyl}methyl)pyrazol-4-yl]formamido}-N-(3-chlorophenyl)-N-methylacetamide;

3-amino-N-{2-[(3-chlorophenyl)(methyl)amino]ethyl}-1-({4-[(2-oxopyridin-1-yl)methyl]phenyl}methyl)pyrazole-4-carboxamide;

3-amino-N-[3-(3-chlorophenyl)propyl]-1-({4-[(2-oxopyridin-1-yl)methyl]phenyl}methyl)pyrazole-4-carboxamide;

N-{2-[(5-chloropyridin-3-yl)oxy]ethyl}-2-methyl-1-({4-[(2-oxopyridin-1-yl)methyl]phenyl}methyl)imidazole-4-carboxamide;

N-[2-(3-chlorophenoxy)ethyl]-2-methyl-1-({4-[(2-oxopyridin-1-yl)methyl]phenyl}methyl)imidazole-4-carboxamide;

5-amino-N-[2-(3-chlorophenoxy)ethyl]-1-({4-[(2-oxopyridin-1-yl)methyl]phenyl}methyl)pyrazole-4-carboxamide;

5-amino-N-[2-(3-chlorophenoxy)ethyl]-1-(1H-indazol-5-ylmethyl)pyrazole-4-carboxamide;

5-amino-N-[2-(3-chlorophenoxy)ethyl]-1-({4-[(pyrrolidin-1-yl)carbonyl]phenyl}methyl)pyrazole-4-carboxamide;

3-amino-N-{2-[(S-chloropyridin-3-yl)oxy]ethyl}-1-({4-[(2-oxopyridin-1-yl)methyl]phenyl}methyl)pyrazole-4-carboxamide;

N-[3-(5-chloro-2-oxopyrimidin-1-yl)propyl]-3-(methoxymethyl)-1-({4-[(2-oxopyridin-1-yl)methyl]phenyl}methyl)pyrazole-4-carboxamide;

N-[3-(5-chloro-1,3-thiazol-2-yl)propyl]-3-(methoxymethyl)-1-({4-[(2-oxopyridin-1-yl)methyl]phenyl}methyl)pyrazole-4-carboxamide;

3-amino-N-[3-(4-chloropyrazol-1-yl)propyl]-1-({4-[(2-oxopyridin-1-yl)methyl]phenyl}methyl)pyrazole-4-carboxamide;

3-amino-N-{2-[(4-chloro-1H-pyrazol-3-yl)oxy]ethyl}-1-({4-[(2-oxopyridin-1-yl)methyl]phenyl}methyl)pyrazole-4-carboxamide;

N-{2-[(5-chloro-1,3-thiazol-2-yl)oxy]ethyl}-3-(methoxymethyl)-1-({4-[(2-oxopyridin-1-yl)methyl]phenyl}methyl)pyrazole-4-carboxamide;

N-[3-(5-chloro-1,2-oxazol-3-yl)propyl]-3-(methoxymethyl)-1-({4-[(2-oxopyridin-1-yl)methyl]phenyl}methyl)pyrazole-4-carboxamide;

N-{2-[(4-chlorothiophen-2-yl)sulfanyl]ethyl}-3-(methoxymethyl)-1-({4-[(2-oxopyridin-1-yl)methyl]phenyl}methyl)pyrazole-4-carboxamide;

N-{2-[(4-chlorofuran-2-yl)sulfanyl]ethyl}-3-(methoxymethyl)-1-({4-[(2-oxopyridin-1-yl)methyl]phenyl}methyl)pyrazole-4-carboxamide;

N-{2-[(5-chloropyridazin-3-yl)oxy]ethyl}-3-(methoxymethyl)-1-({4-[(2-oxopyridin-1-yl)methyl]phenyl}methyl)pyrazole-4-carboxamide;

3-amino-N-{2-[(4-chloropyridin-2-yl)amino]ethyl}-1-({4-[(2-oxopyridin-1-yl)methyl]phenyl}methyl)pyrazole-4-carboxamide;

N-[2-(3-chlorophenoxy)ethyl]-3-(methoxymethyl)-1-({4-[(4-methyl pyrazol-1-yl)methyl]phenyl}methyl)pyrazole-4-carboxamide;

N-[2-(3-chlorophenoxy)ethyl]-2,5-dimethyl-1-[(2-phenyl-1,3-thiazol-4-yl)methyl]pyrrole-3-carboxamide;

3-amino-N-[2-(3-chlorophenoxy)ethyl]-1-{[6-(pyrrolidin-1-yl)pyridin-3-yl]methyl}pyrazole-4-carboxamide;

3-amino-N-[2-(3-chlorophenoxy)ethyl]-1-{[2-(pyrrolidin-1-yl)pyridin-4-yl]methyl}pyrazole-4-carboxamide;

3-amino-N-[2-(3-chlorophenoxy)ethyl]-1-({4-[(pyrrolidin-1-yl)carbonyl]phenyl}methyl)pyrazole-4-carboxamide;

3-amino-N-[2-(3-chlorophenoxy)ethyl]-1-{[4-(2-oxopyridin-1-yl)phenyl]methyl}pyrazole-4-carboxamide;

3-amino-N-[2-(3-chlorophenoxy)ethyl]-1-{[6-(pyrrolidin-1-yl)pyridin-2-yl]methyl}pyrazole-4-carboxamide;

3-amino-N-[2-(3-chlorophenoxy)ethyl]-1-[(2-methylquinolin-6-yl)methyl]pyrazole-4-carboxamide;

3-amino-1-[(4-bromophenyl)methyl]-N-[2-(3-chlorophenoxy)ethyl]pyrazole-4-carboxamide;

3-amino-1-[(3-bromophenyl)methyl]-N-[2-(3-chlorophenoxy)ethyl]pyrazole-4-carboxamide;

3-amino-N-[2-(3-chlorophenoxy)ethyl]-1-{[3-(1,3-thiazol-5-yl)phenyl]methyl}pyrazole-4-carboxamide;

methyl 4-[(3-amino-4-{[2-(3-chlorophenoxy)ethyl]carbamoyl}pyrazol-1-yl)methyl]benzoate;

3-amino-N-[2-(3-chlorophenoxy)ethyl]-1-([4-(dimethylcarbamoyl)phenyl]methyl)pyrazole-4-carboxamide;

3-amino-N-[2-(3-chlorophenoxy)ethyl]-1-({4-[(piperidin-1-yl)carbonyl]phenyl}methyl)pyrazole-4-carboxamide;

3-amino-N-[2-(3-chlorophenoxy)ethyl]-1-{[4-(methylcarbamoyl)phenyl]methyl}pyrazole-4-carboxamide;

ethyl 3-[(3-amino-4-{[2-(3-chlorophenoxy)ethyl]carbamoyl}pyrazol-1-yl)methyl]benzoate;

3-[(3-amino-4-{[2-(3-chlorophenoxy)ethyl]carbamoyl}pyrazol-1-yl)methyl]benzoic acid;

3-amino-N-[2-(3-chlorophenoxy)ethyl]-1-{[3-(methylcarbamoyl)phenyl]methyl}pyrazole-4-carboxamide;

3-amino-N-[2-(3-chlorophenoxy)ethyl]-1-{[3-(dimethylcarbamoyl)phenyl]methyl}pyrazole-4-carboxamide;

3-amino-N-[2-(3-chlorophenoxy)ethyl]-1-{[2-(pyrazol-1-yl)pyridin-4-yl]methyl}pyrazole-4-carboxamide;

((4-[(3-amino-4-{[2-(3-chlorophenoxy)ethyl]carbamoyl}pyrazol-1-yl)methyl]pyridin-2-yl}(methyl)amino)acetic acid 3-amino-N-[2-(3-chlorophenoxy)ethyl]-1-[(2-{[(methylcarbamoyl)methyl]amino}pyridin-4-yl)methyl]pyrazole-4-carboxamide;

4-[(3-amino-4-{[2-(3-chlorophenoxy)ethyl]carbamoyl}pyrazol-1-yl)methyl]benzoic acid;

3-amino-N-[2-(3-chlorophenoxy)ethyl]-1-({3-[(pyrrolidin-1-yl)carbonyl]phenyl}methyl)pyrazole-4-carboxamide;

3-amino-N-[2-(3-chlorophenoxy)ethyl]-1-[(4-phenoxyphenyl)methyl]pyrazole-4-carboxamide;

3-amino-N-[2-(3-chlorophenoxy)ethyl]-1-[(6-phenylpyridin-2-yl)methyl]pyrazole-4-carboxamide;

3-amino-N-[2-(3-chlorophenoxy)ethyl]-1-[(2-methoxypyridin-4-yl)methyl]pyrazole-4-carboxamide;

3-amino-N-[2-(3-chlorophenoxy)ethyl]-1-[(2-{methyl[(methylcarbamoyl)methyl]amino}pyridin-4-yl)methyl]pyrazole-4-carboxamide;

3-amino-N-[2-(3-chlorophenoxy)ethyl]-1-({4-[(pyrimidin-2-yloxy)methyl]phenyl}methyl)pyrazole-4-carboxamide;

3-amino-N-[2-(3-chlorophenoxy)ethyl]-1-({4-[(3-oxomorpholin-4-yl)methyl]phenyl}methyl)pyrazole-4-carboxamide;

3-amino-N-[2-(3-chlorophenoxy)ethyl]-1-({4-[(2-oxopiperidin-1-yl)methyl]phenyl}methyl)pyrazole-4-carboxamide;

3-amino-N-[2-(3-chlorophenoxy)ethyl]-1-[(6-{[(methylcarbamoyl)methyl]amino}pyridin-3-yl)methyl]pyrazole-4-carboxamide;

3-amino-N-[2-(3-chlorophenoxy)ethyl]-1-{[4-(pyrimidin-2-yl)phenyl]methyl}pyrazole-4-carboxamide;

3-amino-N-[2-(3-chlorophenoxy)ethyl]-1-[(3-phenyl-1,2,4-oxadiazol-5-yl)methyl]pyrazole-4-carboxamide;

3-amino-N-[2-(3-chlorophenoxy)ethyl]-1-[(6-chloropyridin-2-yl)methyl]pyrazole-4-carboxamide;

3-amino-N-[2-(3-chlorophenoxy)ethyl]-1-({4-[(N-methylacetamido)methyl]phenyl}methyl)pyrazole-4-carboxamide;

3-amino-N-[2-(3-chlorophenoxy)ethyl]-1-[(4-{[(dimethylcarbamoyl)(methyl)amino]methyl}phenyl)methyl]pyrazole-4-carboxamide;

3-amino-N-[2-(3-chlorophenoxy)ethyl]-1-[(4-[(N,2-dimethylpropanamido)methyl]phenyl}methyl)pyrazole-4-carboxamide;

3-amino-N-[2-(3-chlorophenoxy)ethyl]-1-({4-[(3-methyl-2-oxopyridin-1-yl)methyl]phenyl}methyl)pyrazole-4-carboxamide;

3-amino-N-[2-(3-chlorophenoxy)ethyl]-1-({4-[(2-oxopyrimidin-1-yl)methyl]phenyl}methyl)pyrazole-4-carboxamide;

3-amino-N-[2-(3-chlorophenoxy)ethyl]-1-[(4-{[methyl(pyridin-2-yl)amino]methyl}phenyl)methyl]pyrazole-4-carboxamide;

3-amino-N-[2-(3-chlorophenoxy)ethyl]-1-{[6-(pyrazol-1-yl)pyridin-3-yl]methyl}pyrazole-4-carboxamide;

3-amino-N-[2-(3-chlorophenoxy)ethyl]-1-{[6-(4-methylpyrazol-1-yl)pyridin-3-yl]methyl}pyrazole-4-carboxamide;

3-amino-1-[(3-benzyl-1,2,4-oxadiazol-5-yl)methyl]-N-[2-(3-chlorophenoxy)ethyl]pyrazole-4-carboxamide;

3-amino-N-[2-(3-chlorophenoxy)ethyl]-1-{[2-(pyridin-3-yl)pyridin-4-yl]methyl}pyrazole-4-carboxamide;

3-amino-N-[2-(3-chlorophenoxy)ethyl]-1-(1H-indazol-5-ylmethyl)pyrazole-4-carboxamide;

3-amino-N-[2-(3-chlorophenoxy)ethyl]-1-[(1-methylindazol-5-yl)methyl]pyrazole-4-carboxamide;

3-amino-N-[2-(3-chlorophenoxy)ethyl]-1-{[2-(2-oxopyrrolidin-1-yl)pyridin-4-yl]methyl}pyrazole-4-carboxamide;

3-amino-N-[2-(3-chlorophenoxy)ethyl]-1-[(1,2-dimethyl-1,3-benzodiazol-5-yl)methyl]pyrazole-4-carboxamide;

3-amino-N-[2-(3-chlorophenoxy)ethyl]-1-{[6-(2-oxopyrrolidin-1-yl)pyridin-3-yl]methyl}pyrazole-4-carboxamide;

3-amino-N-[2-(3-chlorophenoxy)ethyl]-1-{6-(pyridin-3-yl)pyridin-3-yl]methyl}pyrazole-4-carboxamide;

3-amino-N-[2-(3-chlorophenoxy)ethyl]-1-({3-methoxy-4-[(2-oxopyridin-1-yl)methyl]phenyl}methyl)pyrazole-4-carboxamide;

3-amino-N-[2-(3-chlorophenoxy)ethyl]-1-({4-[(2-fluoro-6-oxopyridin-1-yl)methyl]phenyl}methyl)pyrazole-4-carboxamide;

3-amino-N-[2-(3-chlorophenoxy)ethyl]-1-({4-[(5-fluoro-2-oxopyridin-1-yl)methyl]phenyl}methyl)pyrazole-4-carboxamide;

3-amino-N-[2-(3-chlorophenoxy)ethyl]-1-({2-fluoro-4-[(2-oxopyridin-1-yl)methyl]phenyl}methyl)pyrazole-4-carboxamide;

3-amino-N-[2-(3-chlorophenoxy)ethyl]-1-({5-[(2-oxopyridin-1-yl)methyl]pyridin-2-yl}methyl)pyrazole-4-carboxamide;

4-carboxamide;

N-[2-(3-chlorophenoxy)ethyl]-3,5-dimethyl-1-({4-[(2-oxopyridin-1-yl)methyl]phenyl}methyl)pyrazole-4-carboxamide;

N-[2-(3-chlorophenoxy)ethyl]-3-(methoxymethyl)-1-({4-[(4-methyl-2-oxopyridin-1-yl)methyl]phenyl}methyl)pyrazole-4-carboxamide;

3-amino-N-[(2S)-2-(3-chlorophenoxy)propyl]-1-({4-[(5-fluoro-2-oxopyridin-1-yl)methyl]phenyl}methyl)pyrazole-4-carboxamide;

3-amino-N-[(3S)-1-(3-chlorophenyl)pyrrolidin-3-yl]-1-({4-[(2-oxopyridin-1-yl)methyl]phenyl}methyl)pyrazole-4-carboxamide;

3-amino-N-[(3R)-1-(3-chlorophenyl)pyrrolidin-3-yl]-1-({4-[(2-oxopyridin-1-yl)methyl]phenyl}methyl)pyrazole-4-carboxamide;

3-amino-N-[(3S)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3R)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3S)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3R)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3S)-1-(3-chlorophenyl)-5-oxopyrrolidin-3-yl]-1-({4-[(2-oxopyridin-1-yl)methyl]phenyl}methyl)pyrazole-4-carboxamide;

3-amino-N-[(3S)-1-(4-chloropyridin-2-yl)pyrrolidin-3-yl]-1-({4-[(2-oxopyridin-1-yl)methyl]phenyl}methyl)pyrazole-4-carboxamide;

3-amino-N-[(2R)-1-(3-chlorophenoxy)propan-2-yl]-1-({4-[(2-oxopyridin-1-yl)methyl]phenyl}methyl)pyrazole-4-carboxamide;

3-amino-N-[(2S)-1-(3-chlorophenoxy)propan-2-yl]-1-({4-[(2-oxopyridin-1-yl)methyl]phenyl}methyl)pyrazole-4-carboxamide;

3-amino-N-[(2S)-2-(3-chlorophenoxy)propyl-1-({4-[(2-oxopyridin-1-yl)methyl]phenyl}methyl)pyrazole-4-carboxamide;

(2S)-2-{3-amino-1-({4-[(2-oxopyridin-1-yl)methyl]phenyl}methyl)pyrazol-4-yl]formamido}-N-(3-chlorophenyl)-N-methylpropanamide;

(2R)-2-{[3-amino-1-({4-[(2-oxopyridin-1-yl)methyl]phenyl}methyl)pyrazol-4-yl]formamido}-N-(3-chlorophenyl)-N-methylpropanamide;

3-amino-N-[(2R/S)-2-(3-chlorophenoxy)propyl]-1-({4-[(2-oxopyridin-1-yl)methyl]phenyl}methyl)pyrazole-4-carboxamide;

and pharmaceutically acceptable salts and solvates thereof.

The present invention also encompasses, but is not limited to, the compounds listed below:

3-amino-1-[4-(2-oxo-2H-pyridin-1-ylmethyl)-benzyl]-1H-pyrazole-4-carboxylic acid [2-(3-chloro-phenoxy)-ethyl]-amide;

3-amino-1-[4-(2-oxo-2H-pyridin-1-ylmethyl)-benzyl-1H-pyrazole-4-carboxylic acid [(3-chloro-phenylcarbamoyl)-methyl]-amide];

3-amino-N-[(2S)-2-(3-chlorophenoxy)propyl]-1-({4-[(2-oxopyridin-1-yl)methyl]phenyl}methyl)-pyrazole-4-carboxamide;

N-[2-(3-chlorophenoxy)ethyl]-3-(methylamino)-1-({4-[(2-oxopyridin-1-yl)methyl]phenyl}methyl)pyrazole-4-carboxamide 2-{[3-amino-1-({4-[(2-oxopyridin-1-yl)methyl]phenyl}methyl)pyrazol-4-yl]formamido}-N-(2-chlorophenyl)acetamide;

N-[2-(3-chlorophenoxy)ethyl]-3-cyclopropyl-1-({4-[(2-oxopyridin-1-yl)methyl]phenyl}methyl)pyrazole-4-carboxamide;

N-[2-(2-chlorophenoxy)ethyl]-3-(methoxymethyl)-1-({4-[(2-oxopyridin-1-yl)methyl]phenyl}methyl)pyrazole-4-carboxamide;

N-[2-(3-chlorophenoxy)ethyl]-3-(methoxymethyl)-1-({4-[(2-oxopyridin-1-yl)methyl]phenyl}methyl)pyrazole-4-carboxamide;

N-[2-(5-chloro-2-fluorophenoxy)ethyl]-3-(methoxymethyl)-1-({4-[(2-oxopyridin-1-yl)methyl]phenyl}methyl)pyrazole-4-carboxamide;

N-[2-(3-chloro-5-fluorophenoxy)ethyl]-3-(methoxymethyl)-1-({4-[(2-oxopyridin-1-yl)methyl]phenyl}methyl)pyrazole-4-carboxamide;

N-[2-(3-chloro-4-fluorophenoxy)ethyl]-3-(methoxymethyl)-1-({4-[(2-oxopyridin-1-yl)methyl]phenyl}methyl)pyrazole-4-carboxamide;

3-amino-N-[2-(5-chloro-2-methylphenoxy)ethyl]-1-({4-[(2-oxopyridin-1-yl)methyl]phenyl}methyl)pyrazole-4-carboxamide;

3-amino-N-[2-(3-chloro-4-methylphenoxy)ethyl]-1-({4-[(2-oxopyridin-1-yl)methyl]phenyl}methyl)pyrazole-4-carboxamide;

3-amino-N-[2-(2,3-dichlorophenoxy)ethyl]-1-({4-[(2-oxopyridin-1-yl)methyl]phenyl}methyl)pyrazole-4-carboxamide;

3-amino-N-[2-(3,4-dichlorophenoxy)ethyl]-1-({4-[(2-oxopyridin-1-yl)methyl]phenyl}methyl)pyrazole-4-carboxamide;

3-amino-N-[2-(3,5-dichlorophenoxy)ethyl]-1-({4-[(2-oxopyridin-1-yl)methyl]phenyl}methyl)pyrazole-4-carboxamide;

3-amino-N-[2-(5-chloro-2-methylphenoxy)ethyl]-1-({4-[(2-oxopyridin-1-yl)methyl]phenyl}methyl)pyrazole-4-carboxamide;

3-amino-N-[2-(2,5-dichlorophenoxy)ethyl]-1-({4-[(2-oxopyridin-1-yl)methyl]phenyl}methyl)pyrazole-4-carboxamide;

N-[2-(3-chlorophenoxy)ethyl]-3-(dimethylamino)-1-({4-[(2-oxopyridin-1-yl)methyl]phenyl}methyl)pyrazole-4-carboxamide;

N-[2-(3-chlorophenoxy)ethyl]-1-({4-[(2-oxopyridin-1-yl)methyl]phenyl}methyl)pyrazole-4-carboxamide;
N-[2-(3-chlorophenoxy)ethyl]-3-cyano-1-({4-[(2-oxopyridin-1-yl)methyl]phenyl}methyl)pyrazole-4-carboxamide;
N-[2-(3-chlorophenoxy)ethyl]-3-methyl-1-({4-[(2-oxopyridin-1-yl)methyl]phenyl}methyl)pyrazole-4-carboxamide;
2-{[3-amino-1-({4-[(2-oxopyridin-1-yl)methyl]phenyl}methyl)pyrazol-4-yl]formamido}-N-(3-chlorophenyl)-N-methylacetamide;
3-amino-N-{2-[(3-chlorophenyl)(methyl)amino]ethyl}-1-({4-[(2-oxopyridin-1-yl)methyl]phenyl}methyl)pyrazole-4-carboxamide;
3-amino-N-[3-(3-chlorophenyl)propyl]-1-({4-[(2-oxopyridin-1-yl)methyl]phenyl}methyl)pyrazole-4-carboxamide;
N-[2-(3-chlorophenoxy)ethyl]-2-methyl-1-({4-[(2-oxopyridin-1-yl)methyl]phenyl}methyl)imidazole-4-carboxamide;
5-amino-N-[2-(3-chlorophenoxy)ethyl]-1-({4-[(2-oxopyridin-1-yl)methyl]phenyl}methyl)pyrazole-4-carboxamide;
5-amino-N-[2-(3-chlorophenoxy)ethyl]-1-({4-[(pyrrolidin-1-yl)carbonyl]phenyl}methyl)pyrazole-4-carboxamide;
3-amino-N-{2-[(5-chloropyridin-3-yl)oxy]ethyl}-1-({4-[(2-oxopyridin-1-yl)methyl]phenyl}methyl)pyrazole-4-carboxamide;
3-amino-N-{2-[(4-chloropyridin-2-yl)amino]ethyl}-1-({4-[(2-oxopyridin-1-yl)methyl]phenyl}methyl)pyrazole-4-carboxamide;
N-[2-(3-chlorophenoxy)ethyl]-3-(methoxymethyl)-1-({4-[(4-methyl pyrazol-1-yl)methyl]phenyl}methyl)pyrazole-4-carboxamide;
N-[2-(3-chlorophenoxy)ethyl]-2,5-dimethyl-1-[(2-phenyl-1,3-thiazol-4-yl)methyl]pyrrole-3-carboxamide;
3-amino-N-[2-(3-chlorophenoxy)ethyl]-1-{[6-(pyrrolidin-1-yl)pyridin-3-yl]methyl}pyrazole-4-carboxamide;
3-amino-N-[2-(3-chlorophenoxy)ethyl]-1-{[2-(pyrrolidin-1-yl)pyridin-4-yl]methyl}pyrazole-4-carboxamide;
3-amino-N-[2-(3-chlorophenoxy)ethyl]-1-({4-[(pyrrolidin-1-yl)carbonyl]phenyl}methyl)pyrazole-4-carboxamide;
3-amino-N-[2-(3-chlorophenoxy)ethyl]-1-{[4-(2-oxopyridin-1-yl)methyl]phenyl}methyl)pyrazole-4-carboxamide;
3-amino-N-[2-(3-chlorophenoxy)ethyl]-1-{[6-(pyrrolidin-1-yl)pyridin-2-yl]methyl}pyrazole-4-carboxamide;
3-amino-N-[2-(3-chlorophenoxy)ethyl]-1-[(2-methylquinolin-6-yl)methyl]pyrazole-4-carboxamide;
3-amino-1-[(4-bromophenyl)methyl]-N-[2-(3-chlorophenoxy)ethyl]pyrazole-4-carboxamide;
3-amino-1-[(3-bromophenyl)methyl]-N-[2-(3-chlorophenoxy)ethyl]pyrazole-4-carboxamide;
3-amino-N-[2-(3-chlorophenoxy)ethyl]-1-{[3-(1,3-thiazol-5-yl)phenyl]methyl}pyrazole-4-carboxamide;
methyl 4-[(3-amino-4-{[2-(3-chlorophenoxy)ethyl]carbamoyl}pyrazol-1-yl)methyl]benzoate;
3-amino-N-[2-(3-chlorophenoxy)ethyl]-1-{[4-(methylcarbamoyl)phenyl]methyl}pyrazole-4-carboxamide;
ethyl 3-[(3-amino-4-{[2-(3-chlorophenoxy)ethyl]carbamoyl}pyrazol-1-yl)methyl]benzoate;
3-amino-N-[2-(3-chlorophenoxy)ethyl]-1-{[2-(pyrazol-1-yl)pyridin-4-yl]methyl}pyrazole-4-carboxamide;
3-amino-N-[2-(3-chlorophenoxy)ethyl]-1-[(4-phenoxyphenyl)methyl]pyrazole-4-carboxamide;
3-amino-N-[2-(3-chlorophenoxy)ethyl]-1-[(6-phenylpyridin-2-yl)methyl]pyrazole-4-carboxamide;
3-amino-N-[2-(3-chlorophenoxy)ethyl]-1-({4-[(pyrimidin-2-yloxy)methyl]phenyl}methyl)pyrazole-4-carboxamide;
3-amino-N-[2-(3-chlorophenoxy)ethyl]-1-({4-[(3-oxomorpholin-4-yl)methyl]phenyl}methyl)pyrazole-4-carboxamide;
3-amino-N-[2-(3-chlorophenoxy)ethyl]-1-({4-[(2-oxopiperidin-1-yl)methyl]phenyl}methyl)pyrazole-4-carboxamide;
3-amino-N-[2-(3-chlorophenoxy)ethyl]-1-[(6-{[(methylcarbamoyl)methyl]amino}pyridin-3-yl)methyl]pyrazole-4-carboxamide;
3-amino-N-[2-(3-chlorophenoxy)ethyl]-1-{[4-(pyrimidin-2-yl)phenyl]methyl}pyrazole-4-carboxamide;
3-amino-N-[2-(3-chlorophenoxy)ethyl]-1-[(3-phenyl-1,2,4-oxadiazol-5-yl)methyl]pyrazole-4-carboxamide;
3-amino-N-[2-(3-chlorophenoxy)ethyl]-1-({4-[(N-methylacetamido)methyl]phenyl}methyl)pyrazole-4-carboxamide;
3-amino-N-[2-(3-chlorophenoxy)ethyl]-1-[(4-{[(dimethylcarbamoyl)(methyl)amino]methyl}phenyl)methyl]pyrazole-4-carboxamide;
3-amino-N-[2-(3-chlorophenoxy)ethyl]-1-({4-[(N,2-dimethylpropanamido)methyl]phenyl}methyl)pyrazole-4-carboxamide;
3-amino-N-[2-(3-chlorophenoxy)ethyl]-1-({4-[(3-methyl-2-oxopyridin-1-yl)methyl]phenyl}methyl)pyrazole-4-carboxamide;
3-amino-N-[2-(3-chlorophenoxy)ethyl]-1-({4-[(2-oxopyrimidin-1-yl)methyl]phenyl}methyl)pyrazole-4-carboxamide;
3-amino-N-[2-(3-chlorophenoxy)ethyl]-1-[(4-{[methyl(pyridin-2-yl)amino]methyl}phenyl)methyl]pyrazole-4-carboxamide;
3-amino-N-[2-(3-chlorophenoxy)ethyl]-1-{[6-(pyrazol-1-yl)pyridin-3-yl]methyl}pyrazole-4-carboxamide;
3-amino-N-[2-(3-chlorophenoxy)ethyl]-1-{[6-(4-methyl pyrazol-1-yl)pyridin-3-yl]methyl}pyrazole-4-carboxamide;
3-amino-N-[2-(3-chlorophenoxy)ethyl]-1-{[2-(pyridin-3-yl)pyridin-4-yl]methyl}pyrazole-4-carboxamide;
3-amino-N-[2-(3-chlorophenoxy)ethyl]-1-{[2-(2-oxopyrrolidin-1-yl)pyridin-4-yl]methyl}pyrazole-4-carboxamide;
3-amino-N-[2-(3-chlorophenoxy)ethyl]-1-[(1,2-dimethyl-1,3-benzodiazol-5-yl)methyl]pyrazole-4-carboxamide;
3-amino-N-[2-(3-chlorophenoxy)ethyl]-1-{[6-(2-oxopyrrolidin-1-yl)pyridin-3-yl]methyl}pyrazole-4-carboxamide;
3-amino-N-[2-(3-chlorophenoxy)ethyl]-1-{[6-(pyridin-3-yl)pyridin-3-yl]methyl}pyrazole-4-carboxamide;
3-amino-N-[2-(3-chlorophenoxy)ethyl]-1-({3-methoxy-4-[(2-oxopyridin-1-yl)methyl]phenyl}methyl)pyrazole-4-carboxamide;
3-amino-N-[2-(3-chlorophenoxy)ethyl]-1-({4-[(2-fluoro-6-oxopyridin-1-yl)methyl]phenyl}methyl)pyrazole-4-carboxamide;
3-amino-N-[2-(3-chlorophenoxy)ethyl]-1-({4-[(5-fluoro-2-oxopyridin-1-yl)methyl]phenyl}methyl)pyrazole-4-carboxamide;
3-amino-N-[2-(3-chlorophenoxy)ethyl]-1-({2-fluoro-4-[(2-oxopyridin-1-yl)methyl]phenyl}methyl)pyrazole-4-carboxamide;
3-amino-N-[2-(3-chlorophenoxy)ethyl]-1-({5-[(2-oxopyridin-1-yl)methyl]pyridin-2-yl}methyl)pyrazole-4-carboxamide;
N-[2-(3-chlorophenoxy)ethyl]-3-(methoxymethyl)-1-({4-[(4-methyl-2-oxopyridin-1-yl)methyl]phenyl}methyl)pyrazole-4-carboxamide;

3-amino-N-[(3S)-1-(3-chlorophenyl)pyrrolidin-3-yl]-1-({4-[(2-oxopyridin-1-yl)methyl]phenyl}methyl)pyrazole-4-carboxamide;

3-amino-N-[(3R)-1-(3-chlorophenyl)pyrrolidin-3-yl]-1-({4-[(2-oxopyridin-1-yl)methyl]phenyl}methyl)pyrazole-4-carboxamide;

3-amino-N-[(3S)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3R)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3S)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3R)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3S)-1-(3-chlorophenyl)-5-oxopyrrolidin-3-yl]-1-({4-[(2-oxopyridin-1-yl)methyl]phenyl}methyl)pyrazole-4-carboxamide;

3-amino-N-[(3S)-1-(4-chloropyridin-2-yl)pyrrolidin-3-yl]-1-({4-[(2-oxopyridin-1-yl)methyl]phenyl}methyl)pyrazole-4-carboxamide;

3-amino-N-[(2R)-1-(3-chlorophenoxy)propan-2-yl]-1-({4-[(2-oxopyridin-1-yl)methyl]phenyl}methyl)pyrazole-4-carboxamide;

3-amino-N-[(2S)-1-(3-chlorophenoxy)propan-2-yl]-1-({4-[(2-oxopyridin-1-yl)methyl]phenyl}methyl)pyrazole-4-carboxamide;

(2S)-2-{[3-amino-1-({4-[(2-oxopyridin-1-yl)methyl]phenyl}methyl)pyrazol-4-yl]formamido}-N-(3-chlorophenyl)-N-methylpropanamide;

(2R)-2-{[3-amino-1-({4-[(2-oxopyridin-1-yl)methyl]phenyl}methyl)pyrazol-4-yl]formamido}-N-(3-chlorophenyl)-N-methylpropanamide;

3-amino-N-[(2R/S)-2-(3-chlorophenoxy)propyl]-1-({4-[(2-oxopyridin-1-yl)methyl]phenyl}methyl)pyrazole-4-carboxamide;

and pharmaceutically acceptable salts and solvates thereof.

The present invention also encompasses, but is not limited to, the compounds listed below:

3-amino-1-[4-(2-oxo-2H-pyridin-1-ylmethyl)-benzyl]-1H-pyrazole-4-carboxylic acid [2-(3-chloro-phenoxy)-ethyl]-amide;

3-amino-1-[4-(2-oxo-2H-pyridin-1-ylmethyl)-benzyl]-1H-pyrazole-4-carboxylic acid [(3-chloro-phenylcarbamoyl)-methyl]-amide];

3-amino-N-[(2S)-2-(3-chlorophenoxy)propyl]-1-({4-[(2-oxopyridin-1-yl)methyl]phenyl}methyl)pyrazole-4-carboxamide N-[2-(3-chlorophenoxy)ethyl]-3-(methylamino)-1-({4-[(2-oxopyridin-1-yl)methyl]phenyl}methyl)pyrazole-4-carboxamide N-[2-(3-chlorophenoxy)ethyl]-3-(methoxymethyl)-1-({4-[(2-oxopyridin-1-yl)methyl]phenyl}methyl)pyrazole-4-carboxamide;

N-[2-(5-chloro-2-fluorophenoxy)ethyl]-3-(methoxymethyl)-1-({4-[(2-oxopyridin-1-yl)methyl]phenyl}methyl)pyrazole-4-carboxamide;

N-[2-(3-chloro-5-fluorophenoxy)ethyl]-3-(methoxymethyl)-1-({4-[(2-oxopyridin-1-yl)methyl]phenyl}methyl)pyrazole-4-carboxamide;

N-[2-(3-chloro-4-fluorophenoxy)ethyl]-3-(methoxymethyl)-1-({4-[(2-oxopyridin-1-yl)methyl]phenyl}methyl)pyrazole-4-carboxamide;

3-amino-N-[2-(5-chloro-2-methylphenoxy)ethyl]-1-({4-[(2-oxopyridin-1-yl)methyl]phenyl}methyl)pyrazole-4-carboxamide;

3-amino-N-[2-(3-chloro-4-methylphenoxy)ethyl]-1-({4-[(2-oxopyridin-1-yl)methyl]phenyl}methyl)pyrazole-4-carboxamide;

3-amino-N-[2-(3,4-dichlorophenoxy)ethyl]-1-({4-[(2-oxopyridin-1-yl)methyl]phenyl}methyl)pyrazole-4-carboxamide;

3-amino-N-[2-(5-chloro-2-cyanophenoxy)ethyl]-1-({4-[(2-oxopyridin-1-yl)methyl]phenyl}methyl)pyrazole-4-carboxamide;

3-amino-N-[2-(3-chloro-5-methylphenoxy)ethyl]-1-({4-[(2-oxopyridin-1-yl)methyl]phenyl}methyl)pyrazole-4-carboxamide;

3-amino-N-[2-(2,5-dichlorophenoxy)ethyl]-1-({4-[(2-oxopyridin-1-yl)methyl]phenyl}methyl)pyrazole-4-carboxamide;

N-[2-(3-chlorophenoxy)ethyl]-3-(dimethylamino)-1-({4[(2-oxopyridin-1-yl)methyl]phenyl}methyl)pyrazole-4-carboxamide;

N-[2-(3-chlorophenoxy)ethyl]-1-({4-[(2-oxopyridin-1-yl)methyl]phenyl}methyl)pyrazole-4-carboxamide;

N-[2-(3-chlorophenoxy)ethyl]-3-cyano-1-({4-[(2-oxopyridin-1-yl)methyl]phenyl}methyl)pyrazole-4-carboxamide;

N-[2-(3-chlorophenoxy)ethyl]-3-methyl-1-({4-[(2-oxopyridin-1-yl)methyl]phenyl}methyl)pyrazole-4-carboxamide;

2-{[3-amino-1-({4-[(2-oxopyridin-1-yl)methyl]phenyl}methyl)pyrazol-4-yl]formamido}-N-(3-chlorophenyl)-N-methylacetamide;

3-amino-N-{2-[(3-chlorophenyl)(methyl)amino]ethyl}-1-{(4-[(2-oxopyridin-1-yl)methyl]phenyl}methyl)pyrazole-4-carboxamide;

3-amino-N-[3-(3-chlorophenyl)propyl]-1-({4-[(2-oxopyridin-1-yl)methyl]phenyl}methyl)pyrazole-4-carboxamide;

N-[2-(3-chlorophenoxy)ethyl]-2-methyl-1-({4-[(2-oxopyridin-1-yl)methyl]phenyl}methyl)imidazole-4-carboxamide 5-amino-N-[2-(3-chlorophenoxy)ethyl]-1-({4-[(2-oxopyridin-1-yl)methyl]phenyl}methyl)pyrazole-4-carboxamide;

3-amino-N-{2-[(4-chloropyridin-2-yl)amino]ethyl}-1-({4-[(2-oxopyridin-1-yl)methyl]phenyl}methyl)pyrazole-4-carboxamide;

N-[2-(3-chlorophenoxy)ethyl]-3-(methoxymethyl)-1-({4-[(4-methyl pyrazol-1-yl)methyl]phenyl}methyl)pyrazole-4-carboxamide;

3-amino-N-[2-(3-chlorophenoxy)ethyl]-1-[(2-methylquinolin-6-yl)methyl]pyrazole-4-carboxamide;

3-amino-N-[2-(3-chlorophenoxy)ethyl]-1-({4-[(3-oxomorpholin-4-yl)methyl]phenyl}methyl)pyrazole-4-carboxamide;

3-amino-N-[2-(3-chlorophenoxy)ethyl]-1-({4-[(2-oxopiperidin-1-yl)methyl]phenyl}methyl)pyrazole-4-carboxamide;

3-amino-N-[2-(3-chlorophenoxy)ethyl]-1-[(4-{[(dimethylcarbamoyl)(methyl)amino]methyl}phenyl)methyl]pyrazole-4-carboxamide;

3-amino-N-[2-(3-chlorophenoxy)ethyl]-1-({4-[(3-methyl-2-oxopyridin-1-yl)methyl]phenyl}methyl)pyrazole-4-carboxamide;

3-amino-N-[2-(3-chlorophenoxy)ethyl]-1-({4-[(2-oxopyrimidin-1-yl)methyl]phenyl}methyl)pyrazole-4-carboxamide;

3-amino-N-[2-(3-chlorophenoxy)ethyl]-1-({3-methoxy-4-[(2-oxopyridin-1-yl)methyl]phenyl}methyl)pyrazole-4-carboxamide;

3-amino-N-[2-(3-chlorophenoxy)ethyl]-1-({4-[(5-fluoro-2-oxopyridin-1-yl)methyl]phenyl}methyl)pyrazole-4-carboxamide;

3-amino-N-[2-(3-chlorophenoxy)ethyl]-1-({2-fluoro-4-[(2-oxopyridin-1-yl)methyl]phenyl}methyl)pyrazole-4-carboxamide;

3-amino-N-[2-(3-chlorophenoxy)ethyl]-1-({5-[(2-oxopyridin-1-yl)methyl]pyridin-2-yl}methyl)pyrazole-4-carboxamide;

3-amino-N-[(3S)-1-(3-chlorophenyl)pyrrolidin-3-yl]-1-({4-[(2-oxopyridin-1-yl)methyl]phenyl}methyl)pyrazole-4-carboxamide;

3-amino-N-[(3S)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3R)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3R)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3S)-1-(3-chlorophenyl)-5-oxopyrrolidin-3-yl]-1-({4-[(2-oxopyridin-1-yl)methyl]phenyl}methyl)pyrazole-4-carboxamide;

3-amino-N-[(2S)-1-(3-chlorophenoxy)propan-2-yl]-1-({4-[(2-oxopyridin-1-yl)methyl]phenyl}methyl)pyrazole-4-carboxamide;

3-amino-N-[(2R/S)-2-(3-chlorophenoxy)propyl]-1-({4-[(2-oxopyridin-1-yl)methyl]phenyl}methyl)pyrazole-4-carboxamide;

and pharmaceutically acceptable salts and solvates thereof.

The present invention also encompasses, but is not limited to, the compounds listed below:

3-amino-N-[2-(3-chlorophenoxy)ethyl]-1-({4-[(3-methyl-2-oxopyridin-1-yl)methyl]phenyl}methyl)pyrazole-4-carboxamide;

3-amino-N-[2-(3-chlorophenoxy)ethyl]-1-({3-methoxy-4-[(2-oxopyridin-1-yl)methyl]phenyl}methyl)pyrazole-4-carboxamide;

3-amino-N-[2-(3-chlorophenoxy)ethyl]-1-({4-[(5-fluoro-2-oxopyridin-1-yl)methyl]phenyl}methyl)pyrazole-4-carboxamide;

3-amino-N-[(2S)-2-(3-chlorophenoxy)propyl-1-({4-[(2-oxopyridin-1-yl)methyl]phenyl}methyl)pyrazole-4-carboxamide;

and pharmaceutically acceptable salts and solvates thereof.

The present invention also encompasses, but is not limited to, the compounds listed below:

3-amino-1-[4-(2-oxo-2H-pyridin-1-ylmethyl)-benzyl]-1H-pyrazole-4-carboxylic acid [2-(3-chloro-phenoxy)-ethyl]-amide;

3-amino-1-[4-(2-oxo-2H-pyridin-1-ylmethyl)-benzyl]-1H-pyrazole-4-carboxylic acid [(3-chloro-phenylcarbamoyl)-methyl]-amide];

N-[2-(3-chlorophenoxy)ethyl]-3-cyclopropyl-1-({4-[(2-oxopyridin-1-yl)methyl]phenyl}methyl)pyrazole-4-carboxamide;

N-[2-(3-chlorophenoxy)ethyl]-3-(methoxymethyl)-1-({4-[(2-oxopyridin-1-yl)methyl]phenyl}methyl)pyrazole-4-carboxamide;

N-[2-(5-chloro-2-fluorophenoxy)ethyl]-3-(methoxymethyl)-1-({4-[(2-oxopyridin-1-yl)methyl]phenyl}methyl)pyrazole-4-carboxamide;

N-[2-(3-chloro-5-fluorophenoxy)ethyl]-3-(methoxymethyl)-1-({4-[(2-oxopyridin-1-yl)methyl]phenyl}methyl)pyrazole-4-carboxamide;

5-amino-N-[2-(3-chlorophenoxy)ethyl]-1-({4-[(2-oxopyridin-1-yl)methyl]phenyl}methyl)pyrazole-4-carboxamide;

and pharmaceutically acceptable salts and solvates thereof.

In a further aspect, the present invention encompasses the following embodiments:

(i) A compound of formula (I),

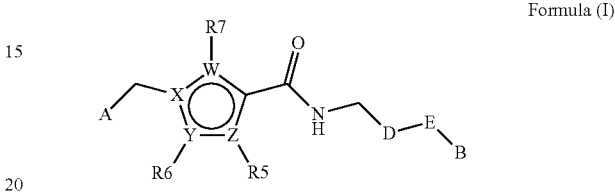

Formula (I)

wherein

B is phenyl substituted with 1 to 3 substituents selected from alkyl, alkoxy, OH, halo, CN, COOR8, CONR8R9, OCF$_3$, CF$_3$ and NR8R9;

or B is 5 or 6 membered heterocyclic ring containing one or two heteroatoms selected from N, O and S; said heterocyclic ring may be aromatic or non-aromatic and is substituted with 1 to 3 substituents selected from alkyl, alkoxy, OH, oxo, halo, CN, COOR8, CONR8R9, OCF$_3$, CF$_3$ and NR8R9;

D is absent or selected from CH$_2$ and CO;

E is absent or selected from NH, CH$_2$, S and 0;

wherein at least one of D or E is present;

W, X, Y and Z are independently selected from C, N, O and S, such that the ring containing W, X, Y and Z is a five membered aromatic heterocycle;

R5, R6 and R7 are independently absent or independently selected from H, alkyl, alkoxy, halo, OH, aryl, heteroaryl, —NR8R9, CN, COOR8, CONR8R9, —NR8COR9, CF$_3$, and R16;

A is selected from aryl and heteroaryl;

R8 and R9 are independently selected from H and alkyl;

R16 is a carbon-containing 3-, 4-, 5- or 6-membered monocyclic ring system which may be aromatic, saturated or unsaturated non-aromatic and which may optionally contain 1, 2, 3 or 4 heteroatoms selected from N, O and S, wherein the ring system R16 is in turn optionally substituted with substituents selected from alkyl and oxo;

alkyl is a linear saturated hydrocarbon having up to 10 carbon atoms (C$_1$-C$_{10}$) or a branched saturated hydrocarbon of between 3 and 10 carbon atoms (C$_3$-C$_{10}$); alkyl may optionally be substituted with 1 or 2 substituents independently selected from (C$_1$-C$_6$)alkoxy, OH, CN, CF$_3$, COOR10, CONR10R11, fluoro and NR10R11;

alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy may optionally be substituted with 1 or 2 substituents independently selected from OH, CN, CF$_3$, COOR10, CONR10R11, fluoro and NR10R11;

aryl is phenyl, biphenyl or naphthyl; aryl may be optionally substituted with 1, 2 or 3 substituents independently selected from alkyl, alkoxy, methylenedioxy, ethylenedioxy, OH, OCF$_3$, halo, CN, heteroaryl, —(CH$_2$)$_{0-3}$—O-heteroaryl, aryl$^b$, —O-aryl$^b$, —(CH$_2$)$_{1-3}$aryl$^b$, —(CH$_2$)$_{1-3}$-heteroaryl, —COOR10, —CONR10R11, —(CH$_2$)$_{0-3}$—NR10R11 and CF$_3$;

aryl$^b$ is phenyl, biphenyl or naphthyl, which may be optionally substituted with 1, 2 or 3 substituents independently selected from alkyl, alkoxy, OH, halo, CN, —COOR10, —CONR10R11, CF$_3$ and NR10R11;
heteroaryl is a 5, 6, 9 or 10 membered mono- or bi-cyclic aromatic ring, containing, where possible, 1, 2 or 3 ring members independently selected from N, NR8, S and O; heteroaryl may be optionally substituted with 1, 2 or 3 substituents independently selected from alkyl, alkoxy, OH, OCF$_3$, halo, CN, aryl, —(CH$_2$)$_{1-3}$-aryl, heteroaryl$^b$, —COOR10, —CONR10R11, CF$_3$ and —(CH$_2$)$_{0-3}$—NR10R11;
heteroaryl$^b$ is a 5, 6, 9 or 10 membered mono- or bi-cyclic aromatic ring, containing, where possible, 1, 2 or 3 ring members independently selected from N, NR8, S and O; wherein heteroaryl$^b$ may be optionally substituted with 1, 2 or 3 substituents independently selected from alkyl, alkoxy, OH, halo, CN, aryl, —(CH$_2$)$_{1-3}$-aryl, —COOR10, —CONR10R11, CF$_3$ and NR10R11;
R10 and R11 are independently selected from H, alkyl, aryl$^b$ and heteroaryl$^b$; or R10 and R11 together with the nitrogen atom to which they are attached form a carbon-containing 4-, 5-, 6- or 7-membered heterocylic ring, optionally containing an additional heteroatom selected from N, S and O, which may be saturated or unsaturated with 1 or 2 double bonds and which may be optionally mono- or di-substituted with substituents selected from oxo, alkyl, alkoxy, OH, halo and CF$_3$;
and tautomers, isomers, stereoisomers (including enantiomers, diastereoisomers and racemic and scalemic mixtures thereof), pharmaceutically acceptable salts and solvates thereof.
(ii) A compound according to embodiment (i), wherein D is selected from CH$_2$ and CO and E is selected from NH, CH$_2$, S and O.
(iii) A compound according to embodiment (i) or (ii), wherein B is selected from phenyl, pyridyl, pyrimidone, pyrimidine, thiazolyl, isothiazolyl, pyrazolyl, imidazolyl, isoxazolyl, oxazolyl, pyrrolyl, thiophenyl and furanyl, each substituted, when possible, with 1 to 3 substituents selected from alkyl, alkoxy, OH, oxo, halo, CN, COOR8, CONR8R9, OCF$_3$, CF$_3$ and NR8R9; wherein alkyl, alkoxy, R8 and R9 are as defined in embodiment (i).
(iv) A compound according to any one of embodiments (i) to (iii), wherein B is selected from phenyl and pyridyl, each substituted with 1 to 3 substituents selected from alkyl, alkoxy and halo; wherein alkyl and alkoxy are as defined in embodiment (i).
(v) A compound according to embodiment (iii) or embodiment (iv), wherein at least one of said 1 to 3 substituents is Cl.
(vi) A compound according to any one of embodiments (i) to (v), wherein W is C and X, Y and Z are independently selected from C and N, such that the ring containing W, X, Y and Z is a five membered aromatic heterocycle.
(vii) A compound according to any one of embodiments (i) to (vi), wherein R7 is selected from H, alkyl, alkoxy, NH$_2$ and CF$_3$; wherein alkyl and alkoxy are as defined in embodiment (i).
(viii) A compound according to any one of embodiments (i) to (viii), wherein R5 and R6 are independently absent or independently selected from H, alkyl, R16, alkoxy, CN, NR8R9 and CF$_3$; wherein R16 is cycloalkyl and cycloalkyl is a monocyclic saturated hydrocarbon of between 3 and 7 carbon atoms; and wherein alkyl, alkoxy, R8 and R9 are as defined in embodiment (i).
(ix) A compound according to embodiment (viii), wherein at least one of R5 and R6 is present and is not H.
(x) A compound according to any one of embodiments (i) to (ix), wherein A is phenyl substituted with —(CH$_2$)$_{1-3}$-heteroaryl or —(CH$_2$)$_{1-3}$—NR10R11 and, optionally, 1 or 2 additional substituents independently selected from alkyl, halo and CF$_3$; wherein alkyl, heteroaryl, R10 and R11 are as defined in embodiment (i).
(xi) A compound according to any one of embodiments (i) to (ix), wherein A is pyridyl substituted with heteroaryl$^b$ or —NR10R11 and, optionally, 1 or 2 additional substituents independently selected from alkyl, halo and CF$_3$; wherein alkyl, heteroaryl$^b$, R10 and R11 are as defined in embodiment (i).

Therapeutic Applications

As previously mentioned, the compounds of the present invention are potent and selective inhibitors of plasma kallikrein. They are therefore useful in the treatment of disease conditions for which over-activity of plasma kallikrein is a causative factor.

Accordingly, the present invention provides a compound of formula (I) for use in medicine.

The present invention also provides for the use of a compound of formula (I) in the manufacture of a medicament for the treatment or prevention of a disease or condition in which plasma kallikrein activity is implicated.

The present invention also provides a compound of formula (I) for use in the treatment or prevention of a disease or condition in which plasma kallikrein activity is implicated.

The present invention also provides a method of treatment of a disease or condition in which plasma kallikrein activity is implicated comprising administration to a subject in need thereof a therapeutically effective amount of a compound of formula (I).

In one aspect, the disease or condition in which plasma kallikrein activity is implicated is selected from impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery.

In a preferred aspect, the disease or condition in which plasma kallikrein activity is implicated is retinal vascular permeability associated with diabetic retinopathy and diabetic macular edema.

Combination Therapy

The compounds of the present invention may be administered in combination with other therapeutic agents. Suitable combination therapies include a compound of formula (I) combined with one or more agents selected from agents that inhibit platelet-derived growth factor (PDGF), endothelial growth factor (VEGF), integrin alpha5beta1, steroids, other agents that inhibit plasma kallikrein and other inhibitors of inflammation. Specific examples of therapeutic agents that may be combined with the compounds of the present invention include those disclosed in EP2281885A and by S. Patel in *Retina,* 2009 June; 29(6 Suppl):S45-8.

When combination therapy is employed, the compounds of the present invention and said combination agents may exist in the same or different pharmaceutical compositions, and may be administered separately, sequentially or simultaneously.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

Definitions

The term "alkyl" includes saturated hydrocarbon residues including:
  linear groups up to 10 carbon atoms ($C_1$-$C_{10}$), or of up to 6 carbon atoms ($C_1$-$C_6$), or of up to 4 carbon atoms ($C_1$-$C_4$). Examples of such alkyl groups include, but are not limited, to $C_1$-methyl, $C_2$-ethyl, $C_3$-propyl and $C_4$-n-butyl.
  branched groups of between 3 and 10 carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.
each optionally substituted as stated above.

Cycloalkyl is a monocyclic saturated hydrocarbon of between 3 and 7 carbon atoms, or between 3 and 6 carbon atoms, or between 3 and 5 carbon atoms; wherein cycloalkyl may optionally be substituted with a substituent selected from alkyl, alkoxy and NR12R13; wherein R12 and R13 are independently selected from H and alkyl or R12 and R13 together with the nitrogen to which they are attached form a 4-, 5-, 6- or 7-membered heterocylic ring which may be saturated or unsaturated with 1 or 2 double bonds and which may be optionally mono- or di-substituted with substituents selected from oxo, alkyl, alkoxy, OH, F and $CF_3$. Cycloalkyl groups may contain from 3 to 7 carbon atoms, or from 3 to 6 carbon atoms, or from 3 to 5 carbon atoms, or from 3 to 4 carbon atoms. Examples of suitable monocyclic cycloalkyl groups include cyclopropyl, cyclobutyl, cyclopentyl, cyclohexyl and cycloheptyl.

The term "alkoxy" includes O-linked hydrocarbon residues including:
  linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.
  branched groups of between 3 and 6 carbon atoms ($C_3$-$C_6$) or of between 3 and 4 carbon atoms ($C_3$-$C_4$). Examples of such alkoxy groups include, but are not limited to, $C_3$-iso-propoxy, and $C_4$-sec-butoxy and tert-butoxy.
each optionally substituted as stated above.

Unless otherwise stated, halo is selected from Cl, F, Br and I.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above). Preferably aryl is selected from phenyl, substituted phenyl (substituted as stated above) and naphthyl.

Heteroaryl is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Preferably heteroaryl is selected from pyridyl, benzothiazole, indole, N-methylindole, thiazole, substituted thiazole, thiophenyl, furyl, pyrazine, pyrazole and substituted pyrazole; wherein substituents are as stated above.

The term "azacarbocycle" includes 5 and 6 membered mono-cyclic carbon-containing rings, comprising one or two nitrogen atoms in the ring, which may optionally be substituted by oxo or alkyl$^b$. Examples of suitable azacarbocycles include pyrrolidine, pyrazolidine, imidazoline, piperidine and piperazine (optionally substituted as stated above). Preferably, "azacarbocycle" is a 5 or 6 membered mono-cyclic carbon-containing ring, comprising one or two nitrogen atoms in the ring, which may optionally be substituted by oxo. Preferably, azacarbocycle is a 5-membered mono-cyclic carbon-containing ring, comprising one or two nitrogen atoms in the ring, which may optionally be substituted by oxo. Preferably, azacarbocycle is a 5-membered mono-cyclic carbon-containing ring, comprising one nitrogen atom in the ring, which may optionally be substituted by oxo. More preferably, azacarbocycle is pyrrolidine, optionally substituted with oxo.

The term "N-linked", such as in "N-linked heterocycloalkyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as —$(CH_2)_{1-3}$-aryl, "-" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming prodrugs are described in 'The Practice of Medicinal Chemistry, $2^{nd}$ Ed. pp 561-585 (2003) and in F. J. Leinweber, *Drug Metab. Res.,* 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof.

For example, compounds of formula (I) wherein U or D are CHalkyl$^b$ or C(alkyl$^b$)$_2$ may be enantiomeric or diasteromeric. All enantiomers, diasteromers and racemates of such compounds are encompassed by the present invention. For example, the invention encompasses 3-amino-N-[(2S)-2-(3-chlorophenoxy)propyl]-1-({4-[(2-oxopyridin-1-yl)methyl]phenyl}methyl)pyrazole-4-carboxamide, 3-amino-N-[(2R)-2-(3-chlorophenoxy)propyl]-1-({4-[(2-oxopyridin-1-yl)methyl]phenyl}meth)pyrazole-4-carboxamide and 3-amino-N-[2-(3-chlorophenoxy)propyl]-1-({4-[(2-oxopyridin-1-yl)methyl]phenyl}methyl)pyrazole-4-carboxamide.

Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

Unless otherwise stated, the compounds of the invention include compounds that differ only in the presence of one or more isotopically enriched atoms. For example, compounds wherein hydrogen is replaced by deuterium or tritium, or wherein carbon is replaced by $^{13}$C or $^{14}$C, are within the scope of the present invention. Such compounds are useful, for example, as analytical tools or probes in biological assays.

In the context of the present invention, references herein to "treatment" include references to curative, palliative and prophylactic treatment.

General Methods

The compounds of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient.

For the treatment of conditions such as retinal vascular permeability associated with diabetic retinopathy and diabetic macular edema, the compounds of the invention may be administered in a form suitable for injection into the ocular region of a patient, in particular, in a form suitable for intra-vitreal injection. It is envisaged that formulations suitable for such use will take the form of sterile solutions of a compound of the invention in a suitable aqueous vehicle. The compositions may be administered to the patient under the supervision of the attending physician.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

In one embodiment, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvent. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The compounds according to general formula I can be prepared using conventional synthetic methods for example, but not limited to, the route outlined in Scheme 1. The amine 2 is coupled to an acid 1 to give the compound 3. This coupling is typically carried out using standard coupling conditions such as hydroxybenzotriazole and a carbodiimide, such as water soluble carbodiimide, in the presence of an organic base. Other standard coupling methods include the reaction of acids with amines in the presence of 2-(1H-benzotriazole-1-yl)-1,1,3,3-tetramethylaminium hexafluorophosphate, 2-(3H-[1,2,3]triazolo[4,5-b]pyridin-3-yl)-1,1,3,3-tetramethylisouronium hexafluorophosphate(V), benzotriazole-1-yl-oxy-tris-pyrrolidino-phosphoium hexafluorophosphate or bromo-trispyrolidino-phosphoium hexafluorophosphate in the presence of organic bases such as triethylamine, diisopropylethylamine or N-methylmorpholine. Alternatively the amide formation can take place via an acid chloride in the presence of an organic base. Such acid chlorides can be formed by methods well known in the literature, for example reaction of the acid with oxalyl chloride or thionyl chloride.

Scheme 1

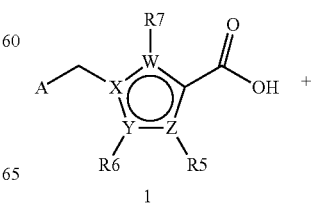

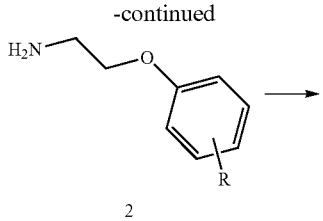

2

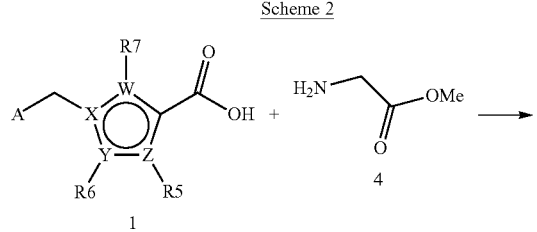

3

Alternatively compounds according to general formula I can be prepared using the route exemplified in Scheme 2. The acid 1 can be coupled for example to glycine using suitable coupling methods as previously described to give compound 5 in which the carboxyl group is protected with a standard protecting group such as an ester, for example methyl ester. In a typical second step the protecting group is removed to give compound 6 using standard methods as previously described. In a final step compound 6 is coupled with an amine such as compound 7 using suitable coupling methods as previously described to give the amide 8.

Scheme 2

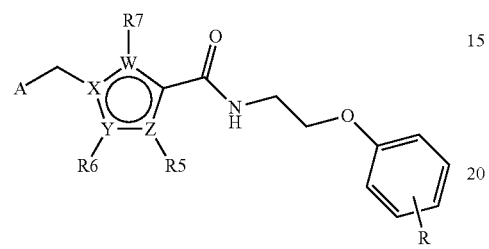

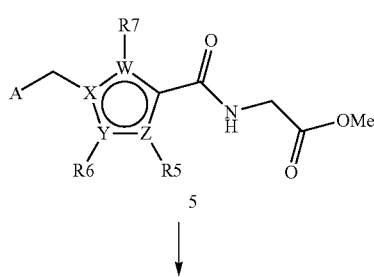

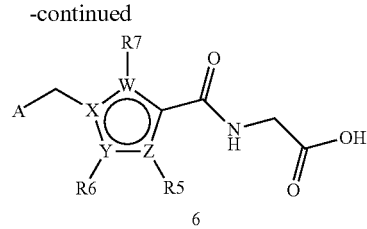

6

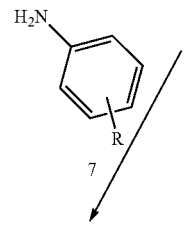

7

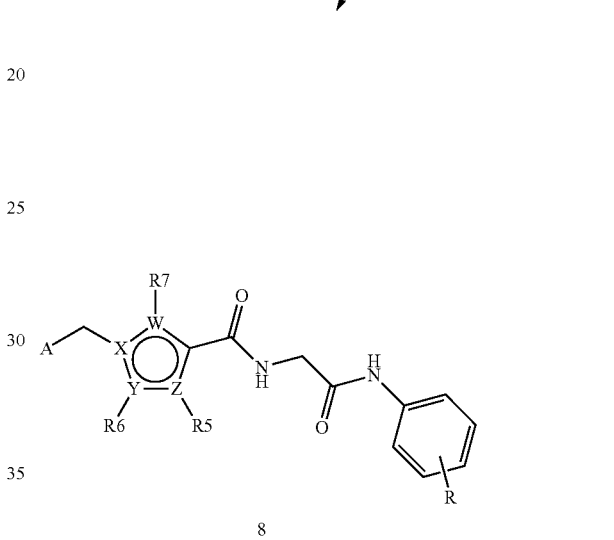

8

Alternatively compounds according to general formula I can be prepared using the route outlined in Scheme 3. The acid 9 can be coupled to an amine 2 using suitable coupling methods as previously described to give compound 10. In a typical second step the nitrogen of the heterocyclic ring is alkylated with compound 11 to give compound 12. The alkylation can be carried out in the presence of a base such as potassium carbonate, cesium carbonate, sodium carbonate or sodium hydride in which case the leaving group is a halide or sulphonate. Alternatively the alkylation may be carried out using an alcohol under Mitsunobu conditions in the presence of triphenylphosphine.

Scheme 3

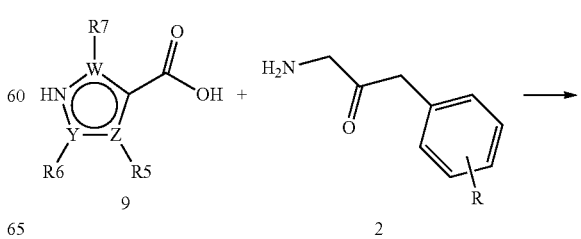

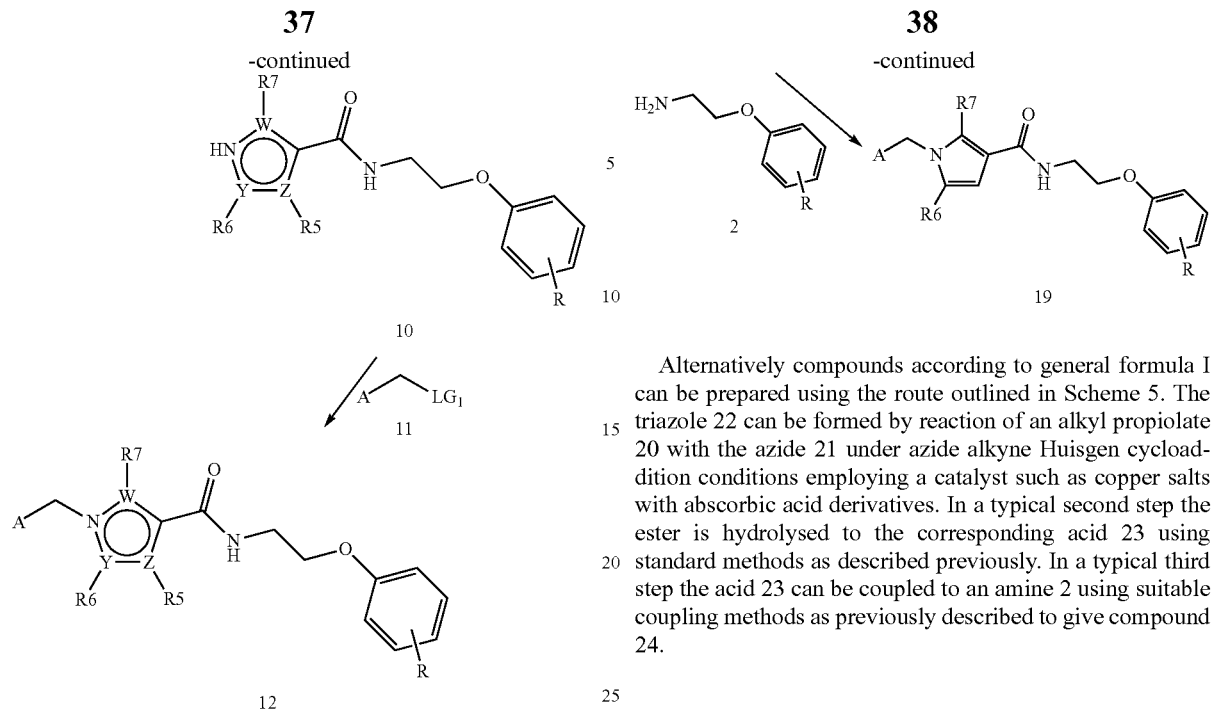

Alternatively compounds according to general formula I can be prepared using the route outlined in Scheme 4. The pyrrole 17 can be formed in two steps the first of which involves reaction of the sodium salt of an alkyl ketoacetate 13, typically protected with a protecting group (PG) as described previously, with a chloroketone 14 in the presence of a base such as potassium carbonate to give compound 15 which in a typical second step is reacted with the amine 16 in the presence of an acid such as but not limited to sulphonic acid derivatives e.g. p-toluenesulphonic acid to yield compound 17 which in a typical third step is subsequently hydrolysed to the corresponding acid 18 using standard methods as described previously. In a typical fourth step the acid 18 can be coupled to an amine 2 using suitable coupling methods as previously described to give compound 19.

Alternatively compounds according to general formula I can be prepared using the route outlined in Scheme 5. The triazole 22 can be formed by reaction of an alkyl propiolate 20 with the azide 21 under azide alkyne Huisgen cycloaddition conditions employing a catalyst such as copper salts with abscorbic acid derivatives. In a typical second step the ester is hydrolysed to the corresponding acid 23 using standard methods as described previously. In a typical third step the acid 23 can be coupled to an amine 2 using suitable coupling methods as previously described to give compound 24.

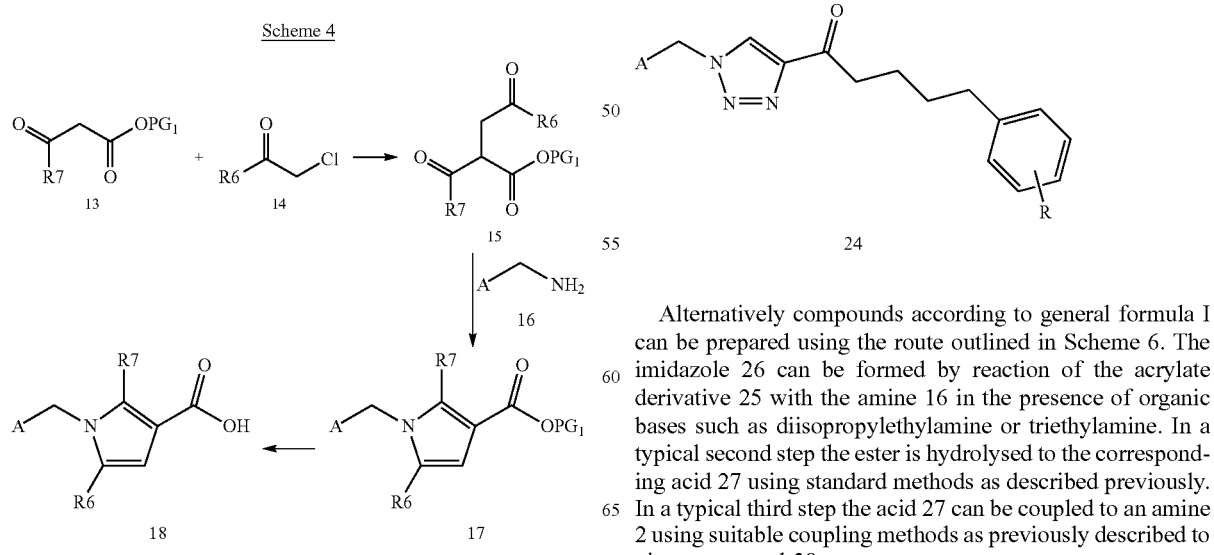

Alternatively compounds according to general formula I can be prepared using the route outlined in Scheme 6. The imidazole 26 can be formed by reaction of the acrylate derivative 25 with the amine 16 in the presence of organic bases such as diisopropylethylamine or triethylamine. In a typical second step the ester is hydrolysed to the corresponding acid 27 using standard methods as described previously. In a typical third step the acid 27 can be coupled to an amine 2 using suitable coupling methods as previously described to give compound 28.

Additional methods for the preparation of compounds according to general formula I are described in WO 2014/108670 A1.

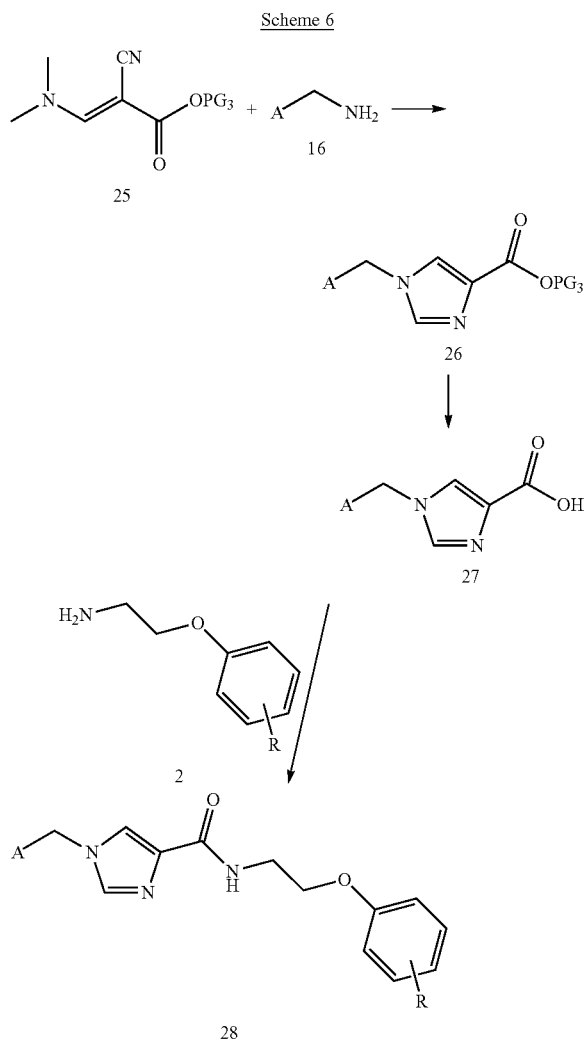

Scheme 6

EXAMPLES

The invention is illustrated by the following non-limiting examples in which the following abbreviations and definitions are used:

| aq | Aqueous solution |
|---|---|
| DCM | Dichloromethane |
| DMF | N,N-Dimethylformamide |
| DMSO | Dimethyl sulfoxide |
| EDC | 1-Ethyl-3-(3-dimethylaminopropyl)carbodiimide |
| EtOAc | Ethyl Acetate |
| HATU | 2-(3H-[1,2,3]triazolo[4,5-b]pyridin-3-yl)-1,1,3,3-tetramethyl-isouronium hexafluorophosphate(V) |
| hrs | Hours |
| HOBt | Hydroxybenzotriazole |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum - NMR spectra were recorded at a frequency of 400 MHz unless otherwise indicated |
| Pet. Ether | Petroleum ether fraction boiling at 60-80° C. |
| Ph | Phenyl |
| PyBrop | Bromo-trispyrolidino-phosphoium hexafluorophosphate |
| Sat. | Saturated |
| SWFI | Sterile water for injection |
| rt | room temperature |
| THF | Tetrahydrofuran |
| TFA | Trifluoroacetic acid |

All reactions were carried out under an atmosphere of nitrogen unless specified otherwise.

$^1$H NMR spectra were recorded on a Bruker (400 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% $HCO_2H$/MeCN into 0.1% $HCO_2H$/$H_2O$ over 13 min, flow rate 1.5 mL/min, or using Agilent, X-Select, acidic, 5-95% MeCN/water over 4 min. Data was collected using a Thermofinnigan Surveyor MSQ mass spectrometer with electrospray ionisation in conjunction with a Thermofinnigan Surveyor LC system.

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Products purified by automated flash chromatography, were done so using a Biotage Isolera using pre-packed silica cartridges (e.g. Biotage SNAP ultra). Reverse phase preparative HPLC purifications were carried out using a Waters 2525 binary gradient pumping system at flow rates of typically 20 mL/min using a Waters 2996 photodiode array detector.

All solvents and commercial reagents were used as received.

Chemical names were generated using automated software such as the Autonom software provided as part of the ISIS Draw package from MDL Information Systems or the Chemaxon software provided as a component of MarvinSketch or as a component of the IDBS E-WorkBook.

A. 1-(4-Hydroxymethyl-benzyl)-1H-pyridin-2-one 4-(Chloromethyl)benzylalcohol (5.0 g, 31.93 mmol) was dissolved in acetone (150 mL). 2-hydroxypyridine (3.64 g, 38.3 mmol) and potassium carbonate (13.24 g, 95.78 mmol) were added and the reaction mixture was stirred at 50° C. for 3 hrs after which time the solvent was removed in vacuo and the residue taken up in chloroform (100 mL). This solution was washed with water (30 mL), brine (30 mL), dried ($Na_2SO_4$) and evaporated in vacuo. The residue was purified by flash chromatography (silica), eluent 3% MeOH/97% $CHCl_3$, to give a white solid identified as 1-(4-hydroxymethyl-benzyl)-1H-pyridin-2-one (5.30 g, 24.62 mmol, 77% yield).

$[M+Na]^+$=238.

A2. 1-(4-(Hydroxymethyl)-2-methoxybenzyl)pyridine-2-one

To a stirred solution of methyl 3-methoxy-4-((2-oxopyridin-1(2H)-yl)methyl)benzoate (1.40 g, 5.11 mmol) in THF (20 mL) at −35° C. was added DIBAl-H (1M in toluene, 20.5 mL, 20.5 mmol) dropwise and left to warm to rt for 4 hrs. The reaction mixture was quenched by dropwise addition of sat. Rochelles salt solution until bubbling ceased. The thick suspension was diluted with ethyl acetate (100 mL) and filtered through Celite. The organics were dried over MgSO$_4$, filtered and concentrated. The residue was purified by automated flash chromatography eluting initially with ethyl acetate in isohexanes then 10% MeOH in ethyl acetate to elute the product. The title compound was isolated as a viscous yellow oil (664 mg, 2.65 mmol, 52% yield).
[MH]$^+$=246.2.

B1. 1-(4-Chloromethyl-benzyl)-1H-pyridin-2-one 1-(4-Hydroxymethyl-benzyl)-1H-pyridin-2-one (8.45 g, 39.3 mmol), dry DCM (80 mL) and triethylamine (7.66 ml, 55.0 mmol) were cooled in an ice bath. Methanesulfonyl chloride (3.95 ml, 51.0 mmol) was added and stirred in ice bath for 15 min. The ice bath was removed and stirring continued at rt temperature overnight. The reaction mixture was partitioned between DCM (100 mL) and saturated aqueous NH$_4$Cl solution (100 mL). The aqueous layer was extracted with further DCM (2×50 mL) and the combined organics washed with brine (50 mL), dried over Na$_2$SO$_4$, filtered and concentrated to give 1-(4-chloromethyl-benzyl)-1H-pyridin-2-one (8.65 g, 36.6 mmol, 93% yield) as a pale yellow solid.
[MH]$^+$=234.1.

B2. 1-(4-Bromomethyl-benzyl)-1H-pyridin-2-one 1-(4-Hydroxymethyl-benzyl)-1H-pyridin-2-one (2.30 g, 6.97 mmol) was dissolved in DCM (250 mL). To this solution was added phosphorous tribromide (5.78 g, 21.37 mmol) The reaction mixture was stirred at rt for 18 hrs and diluted with CHCl$_3$ (250 mL). The filtrate was washed with sat. NaHCO$_3$ (aq) (30 mL), water (30 mL), brine (30 mL), dried (Na$_2$SO$_4$) and evaporated in vacuo to give a white solid which was identified as 1-(4-bromomethyl-benzyl)-1H-pyridin-2-one (2.90 g, 10.43 mmol, 98%).
[MH]$^+$=277.7.

B3. 1-(4-Chloromethyl-benzyl)-5-fluoro-1H-pyridin-2-one

5-Fluoro-1-(4-hydroxymethyl-benzyl)-1H-pyridin-2-one (0.61 g, 2.63 mmol), dry DCM (6 mL) and triethylamine (0.51 ml, 3.68 mmol) were cooled in an ice bath. Methanesulfonyl chloride (0.27 ml, 3.42 mmol) was added and stirred in ice bath for 15 min. The ice bath was removed and stirring continued at ambient temperature. The reaction mixture was partitioned between DCM (50 mL) and saturated aqueous NH$_4$Cl solution (50 mL). The aqueous layer was extracted with further DCM (2×50 mL) and the combined organics washed with brine (50 mL), dried over MgSO$_4$, filtered and concentrated to give 1-(4-chloromethyl-benzyl)-5-fluoro-1H-pyridin-2-one (0.69 g, 2.59 mmol, 98% yield) as a pink solid.
[MH]$^+$=252.

C. [4-(4-Methyl-pyrazol-1-ylmethyl)-phenyl]-methanol 4-(Chloromethyl)benzylalcohol (5.47 g, 34.9 mmol) was dissolved in acetone (50 mL). 4-Methylpyrazole (2.86 g, 34.9 mmol) and potassium carbonate (5.07 g, 36.7 mmol) were added and the reaction mixture was stirred at 18 hrs and at 60° C. for 30 hrs after which time the solvent was removed in vacuo and the residue taken up in EtOAc (100 mL). This solution was washed with water (30 mL), brine (30 mL), dried (MgSO$_4$) and evaporated in vacuo. The residue was purified by flash chromatography (silica), eluent gradient of 10 to 80% EtOAc in iso-Hexane, fractions combined and evaporated in vacuo to give a white solid identified as [4-(4-methyl-pyrazol-1-ylmethyl)-phenyl]-methanol (3.94 g, 18.90 mmol, 54% yield).
[MH]$^+$=203.

D. 1-(4-Chloromethyl-benzyl)-4-methyl-1H-pyrazole

[4-(4-Methyl-pyrazol-1-ylmethyl)-phenyl]-methanol (2.03 g, 10.04 mmol) and triethylamine (1.13 g, 11.54 mmol) was dissolved in DCM (40 mL). To this solution was added methanesulphonyl chloride (1.26 g, 11.04 mmol) dropwise. The reaction mixture was stirred at rt for 18 hrs and diluted with CHCl$_3$ (250 mL). The mixture was washed with saturated NH$_4$Cl (30 mL), water (30 mL), brine (30 mL), dried (Na$_2$SO$_4$) and evaporated in vacuo. The residue was purified by flash chromatography (silica), eluent gradient of 0 to 60% EtOAc in iso-Hexane, fractions combined and evaporated in vacuo to give a white solid identified as 1-(4-chloromethyl-benzyl)-4-methyl-1H-pyrazole (1.49 g, 6.62 mmol, 60% yield).
[MH]$^+$=221, 223.

E. 3-Dimethylamino-1H-pyrazole-4-carboxylic acid ester

5-Amino-1H-pyrazole-4-carboxylic acid ester (1.0 g, 6.45 mmol) was dissolved in methanol (200 mL) and the solution purged with nitrogen. Formaldehyde (37% by weight in water, 4.5 mL, 21.2 mmol) was added followed by 10% Pd/C (1.0 g). The reaction mixture was shaken on a Parr hydrogenator at 10 psi for 18 hrs. The reaction mixture was filtered through celite to remove the catalyst and the residue washed with methanol (200 mL) and water (20 mL). The combined filtrates were evaporated in vacuo. The crude residue was triturated with methanol/diethyl ether and the filtrate concentrated to afford a colourless oil identified as the title compound (1.1 g, 6.00 mmol, 93% yield).
[MH]$^+$=183.7.

F. 3-Amino-1-(6-fluoro-pyridin-3-ylmethyl)-1H-pyrazole-4-carboxylic acid ethyl ester 5-Chloromethyl-2-fluoropyridine (375 mg, 2.58 mmol) was taken up in acetonitrile (25 mL) and potassium carbonate (534 mg, 3.87 mmol) added. Ethyl-3-(amino)-1H-pyrazole-4-carboxylate (400 mg, 2.58 mmol) was dissolved in acetonitrile (50 mL) and added dropwise over 3 hrs and the reaction stirred at rt until complete consumption of starting material. The solvent was removed under vacuum and the residue taken up in ethyl acetate (60 mL) and washed with water (20 mL). The organic layer was dried (MgSO$_4$), filtered and evaporated. The residue was purified by automated flash chromatography eluting with 0-100% of a mixture of ethyl acetate and acetonitrile (2:1 ratio) in petroleum ether to afford two regioisomers. The first regioisomer collected was identified as 5-amino-1-(6-fluoro-pyridin-3-ylmethyl)-1H-pyrazole-4-carboxylic acid ethyl ester (154 mg, 23% yield). The second regioisomer was identified as the title compound (115 mg, 17% yield).
[MH]$^+$=264.9.

G. Methyl 3-(methoxymethyl)-1-(4-((2-oxopyridin-1(2H)-yl)methyl)benzyl)-1H-pyrazole-4-carboxylate Potassium carbonate (519 mg, 3.76 mmol) was added to a solution of methyl 3-(methoxymethyl)-1H-pyrazole-4-carboxylate (320 mg, 1.88 mmol; CAS no. 318496-66-1 (synthesised according to the method described in WO 2012/009009)) and 1-(4-(chloromethyl)benzyl)pyridin-2(1H)-one (527 mg, 2.26 mmol) in DMF (5 mL) and heated at 60° C. overnight. The reaction mixture was diluted with EtOAc (50 mL) and washed with brine (2×100 mL), dried over magnesium sulfate, filtered and reduced in vacuo. The crude product was purified by flash chromatography (40 g column, 0-100% EtOAc in isohexanes) to afford two regioisomers. The second isomer off the column was collected to afford methyl 3-(methoxymethyl)-1-(4-((2-oxopyridin-1(2H)-yl)methyl)benzyl)-1H-pyrazole-4-carboxylate (378 mg, 1.01 mmol, 53.7% yield) as a colourless gum.
[MH]$^+$=368.2.

G2. 3-Amino-1-[4-(2-oxo-2H-pyridin-1-ylmethyl)-benzyl]-1H-pyrazole-4-carboxylic acid ethyl ester 1-(4-Bromomethyl-benzyl)-1H-pyridin-2-one (850 mg, 3.06 mmol) was dissolved in DMF (10 mL). 5-Amino-1H-pyrazole-4-carboxylic acid ethyl ester (522 mg, 3.36 mmol) and cesium carbonate (1.99 g, 6.11 mmol) were added and the reaction mixture was stirred at 50° C. for 18 hrs after which time the reaction mixture was diluted with EtOAc (100 mL). This solution was washed with water (30 mL), brine (30 mL), dried (Na$_2$SO$_4$) and evaporated in vacuo. The residue was purified by flash chromatography (silica), eluent gradient from 30% Pet Ether/70% EtOAc to 100% EtOAc, to afford two regioisomers. The first isomer was identified as 5-amino-1-[4-(2-oxo-2H-pyridin-1-ylmethyl)-benzyl]-1H-pyrazole-4-carboxylic acid ethyl ester (230 mg, 0.65 mmol, 21% yield) as a white solid. The second isomer off the column was collected to afford 3-amino-1-[4-(2-oxo-2H-pyridin-1-ylmethyl)-benzyl]-1H-pyrazole-4-carboxylic acid ethyl ester (480 mg, 1.36 mmol, 45% yield) as a white solid.
[MH]$^+$=353.1.

H. 3-(Methoxymethyl)-1-(4-((2-oxopyridin-1(2H)-yl)methyl)benzyl)-1H-pyrazole-4-carboxylic acid To methyl 3-(methoxymethyl)-1-(4-((2-oxopyridin-1(2H)-yl)methyl)benzyl)-1H-pyrazole-4-carboxylate (3.77 g, 10.26 mmol) in THF (5 mL) and MeOH (5 mL) was added 2M NaOH solution (15.39 ml, 30.8 mmol) and stirred at rt overnight. 1M HCl (50 mL) was added and extracted with EtOAc (50 mL). The organic layer was washed with brine (50 mL), dried over magnesium sulfate, filtered and reduced in vacuo to give 3-(methoxymethyl)-1-(4-((2-oxopyridin-1(2H)-yl)methyl)benzyl)-1H-pyrazole-4-carboxylic acid (1.22 g, 3.45 mmol, 33.6% yield) as a white powder.
[MH]$^+$=354.2.

H2. 3-Amino-1-[4-(2-oxo-2H-pyridin-1-ylmethyl)-benzyl]-1H-pyrazole-4-carboxylic acid 3-Amino-1-[4-(2-oxo-2H-pyridin-1-ylmethyl)-benzyl]-1H-pyrazole-4-carboxylic acid ethyl ester (480 mg, 1.36 mmol) was dissolved in THF (50 mL) and water (5 mL). Lithium hydroxide (16 3 mg, 6.81 mmol) was added. The reaction mixture was stirred at 50° C. for 18 hrs after which time the volatiles were removed in vacuo and the aqueous residue washed with CHCl$_3$ (150 mL). The aqueous layer was acidified with 1M HCl to pH7 and extracted with CHCl$_3$ (3×50 mL). The combined extracts were washed with water (30 mL), brine (30 mL), dried (Na$_2$SO$_4$) and evaporated in vacuo to give a white solid identified as 3-amino-1-[4-(2-oxo-2H-pyridin-1-ylmethyl)-benzyl]-1H-pyrazole-4-carboxylic acid (370 mg, 1.14 mmol, 84%).
[MH]$^+$=325.2.

I. [(S)-2-(3-Chloro-phenoxy)-propyl]-carbamic acid tert-butyl ester

To a stirred solution of (S)-tert-butyl-(2-hydroxypropyl) carbamate (1.50 g, 8.56 mmol) in THF (15 mL) was added 3-chlorophenol (1.00 g, 7.78 mmol) and triphenylphospine (2.24 g, 8.56 mmol). The reaction mixture was cooled to 0° C. and placed under nitrogen. A solution of diethyl azodicarboxylate (1.34 mL, 8.56 mmol) in THF (15 mL) was added dropwise. The reaction mixture was stirred at room temperature. The reaction mixture was concentrated and purified by automated flash column eluting with ethyl acetate/petrol to afford a colourless oil which contained the title compound and unreacted phenol. Taken through to next stage without further purification.

J. N-(2-Aminomethyl)-4-chloropyridin-2-amine

To a suspension of 2,4-dichloropyridine (500 mg, 3.38 mmol) in 1,4-dioxane (3 mL) was added N-boc-ethylenediamine (228 mg, 3.38 mmol) and triethylamine (0.47 mL, 3.38 mmol) and the reaction stirred at 95° C. for 24 hrs then increased to 120° C. for a further 24 hrs. The reaction mixture was cooled and solvent removed under vacuum. Ethyl acetate (70 ml) and water (25 mL) were added to the dry residue. The organic layer was washed with brine (25 mL), dried (MgSO$_4$), filtered and concentrated. The residue was purified by automated flash chromatography eluting with ethyl acetate and pet ether affording two products. The first product eluted was identified as [2-(4-chloro-pyridin-2-ylamino)-ethyl]-carbamic acid tert-butyl ester as an orange crystalline solid (50 mg, 0.18 mmol, 9% yield). The second product eluted was identified as [2-(2-chloro-pyridin-4-ylamino)-ethyl]-carbamic acid tert-butyl ester as an orange oil (95 mg, 0.35 mmol, 17% yield). [2-(4-Chloro-pyridin-2-ylamino)-ethyl]-carbamic acid tert-butyl ester was dissolved in 4M HCl in dioxane and stirred at rt for 3 hrs. The reaction mixture was concentrated under vacuum giving the title compound as a tan solid (39 mg, quantitative yield).
[MH]$^+$=172.0.

K. (S)-1-(3-chloro-phenyl)-pyrrolidin-3-ylamine (S)-3-Boc-aminopyrrolidine (150 mg, 0.81 mmol), Cs$_2$CO$_3$ (315 mg, 0.97 mmol), and 3-chlorobromobenzene (154 mg, 0.81 mmol) were suspended in dry toluene (2 mL). Nitrogen was bubbled through the mixture for 2-3 min then Pd$_2$(dba)$_3$ (37 mg, 0.04 mmol) and BINAP (75 mg, 0.12 mmol) were added. The reaction was heated at 110° C. for 18 hrs. The reaction mixture was cooled and ethyl acetate (15 mL) added. The solid material was filtered off and washed with further ethyl acetate (2×5 mL). The filtrate was concentrated and purified by automated flash chromatography eluting with ethyl acetate and pet ether to afford [(S)-1-(3-chloro-phenyl)-pyrrolidin-3-yl]-carbamic acid tert butyl ester (155 mg, 0.52 mmol, 65% yield). To the boc protected product was added 4M HCl in dioxane and stirred at rt for 4 hrs. The reaction mixture was concentrated to afford the title compound as the HCl salt (120 mg, 0.51 mmol, 99% yield).

[MH]$^+$=296.8.

L1. (S)-3-Amino-1-(3-chloro-phenyl)-pyrrolidin-2-one

[(S)-1-(3-Chloro-phenylcarbamoyl)-3-methylsulfanyl-propyl]-carbamic acid tert butyl ester Boc-L-methionine (1.0 g, 4.01 mmol) was dissolved in dichloromethane (50 mL), PyBrop (2.2 g, 4.81 mmol) was added followed by triethylamine (1.01 g, 10.0 mmol). After 20 min 3-chloroaniline (614 mg, 4.81 mmol) was added. The reaction mixture was stirred at room temperature for 18 hrs and diluted with chloroform (200 mL). This solution was washed with 0.3M KHSO$_4$ (1×50 mL), water (1×50 mL), brine (1×50 mL), dried (Na$_2$SO$_4$) and filtered through PS paper and evaporated in vacuo. The residue was purified by flash chromatography (silica) Eluent: 20% EtOAc, 80% Pet Ether 60-80° C. Fractions were combined and evaporated in vacuo to give a white solid identified as the title compound (545 mg, 1.52 mmol, 38% yield).

[MH]$^+$=358.9.

[(S)-1-(3-Chloro-phenylcarbamoyl)-3-(dimethyl-lambda*4*sulfanyl)-propyl]-carbamic acid tert butyl ester

[(S)-1-(3-Chloro-phenylcarbamoyl)-3-methylsulfanyl-propyl]-carbamic acid tert butyl ester (545 mg, 1.52 mmol) was dissolved in iodomethane (10 mL). After 3 days at room temperature the solvent was removed in vacuo to give a yellow solid identified as the title compound (560 mg 1.49 mmol, 98% yield).

[MH]$^+$=372.9.

[(S)-1-(3-Chloro-phenyl)-2-oxo-pyrrolidin-3-yl]-carbamic acid tert butyl ester Lithium bis(trimethylsilyl)amide (1M solution in toluene, 1.6 mL, 1.60 mmol) was added portionwise to a solution of [(S)-1-(3chloro-phenylcarbamoyl)-3-(dimethyl-lambda*4*sulfanyl)-propyl]-carbamic acid tert butyl ester (500 mg, 1.33 mmol) in anhydrous THF (25 mL) at 0° C. The mixture was stirred for 2 hrs at 0° C. to room temperature after which time the reaction mixture was diluted with EtOAc (100 mL), this solution was washed with water (1×30 mL), brine (1×30 mL), dried (Na$_2$SO$_4$) and filtered through PS paper and evaporated in vacuo. The residue was purified by flash chromatography (silica), eluent 30% EtOAc, 70% Pet Ether 60-80, fractions combined and evaporated in vacuo to give a pale yellow solid identified as the title compound (230 mg, 0.74 mmol, 55% yield).

[MH]$^+$=310.9.

(S)-3-Amino-1-(3-chloro-phenyl)-pyrrolidin-2-one

[(S)-1-(3-Chloro-phenyl)-2-oxo-pyrrolidin-3-yl]-carbamic acid tert butyl ester (230 mg, 6.07 mmol) was dissolved in 4M HCl in dioxane (30 mL). After 1 hr at room temperature the solvent was removed in vacuo to give a white solid identified as the title compound (180 mg, 0.73 mol, 98% yield).

[MH]+=210.8.

L2. (R)-3-amino-1-(3-chloro-phenyl)-pyrrolidin-2-one

Made in an analogous manner to (S)-3-amino-1-(3-chloro-phenyl)-pyrrolidin-2-one starting from Boc-D-methionine.

Example 1

3-Amino-1-[(4-(2-oxo-2H-pyridin-1-ylmethyl)-benzyl]-1H-pyrazole-4-carboxylic acid [2-(3-chlorophenoxy)-ethyl]-amide

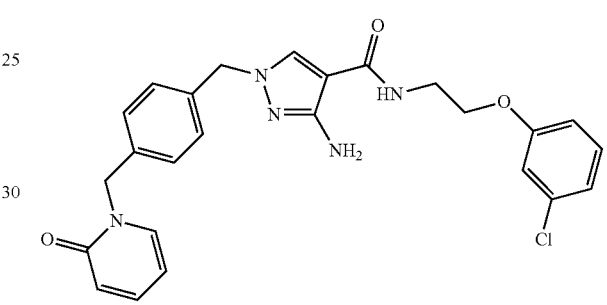

3-Amino-1-[4-(2-oxo-2H-pyridin-1-ylmethyl)-benzyl]-1H-pyrazole-4-carboxylic acid (80 mg, 0.25 mmol) was dissolved in DCM (20 mL) and DMF (1 mL). This solution was cooled to 0° C. 2-(3-Chlorophenoxy)-ethylamine (51 mg, 0.30 mmol) was added followed by HOBt (37 mg, 0.27 mmol) and triethylamine (75 mg, 0.74 mmol). Water soluble carbodiimide (57 mg, 0.30 mmol) was then added. The mixture was allowed to warm to rt and after 18 hrs the mixture was diluted with chloroform (200 mL) and washed with sat. NaHCO$_3$ (aq) (50 mL), water (50 ml) and brine (50 mL), dried (Na$_2$SO$_4$) and evaporated in vacuo. The residue was purified by flash chromatography (silica), eluent 4% MeOH/96% CHCl$_3$ to give a white solid identified as 3-amino-1-[4-(2-oxo-2H-pyridin-1-ylmethyl)-benzyl]-1H-pyrazole-4-carboxylic acid [2-(3-chloro-phenoxy)-ethyl]-amide (68 mg, 0.14 mmol, 52%).

[MH]$^+$=478.1.

$^1$H NMR: (d6-DMSO) δ: 3.48-3.50 (2H, m), 4.05 (2H, t, J=5.7 Hz), 5.04 (2H, s), 5.07 (2H, s), 5.37 (2H, d, J=9.6 Hz), 6.21-6.24 (1H, m), 6.39 (1H, d, J=8.8 Hz), 6.91-6.94 (1H, m), 6.98-7.00 (1H, m), 7.03 (1H, t, J=2.2 Hz), 7.18 (2H, d, J=8.2 Hz), 7.26 (2H, d, J=8.2 Hz), 7.30 (1H, t, J=8.2 Hz), 7.39-7.42 (1H, m), 7.77 (1H, dd, J=1.9, 8.2 Hz), 7.96 (1H, s), 8.00 (1H, t, J=5.5 Hz).

Example 2

3-Amino-1-[4-(2-oxo-2H-pyridin-1-ylmethyl)-benzyl]-1H-pyrazole-4-carboxylic acid [(3-chloro-phenylcarbamoyl)-methyl]-amide

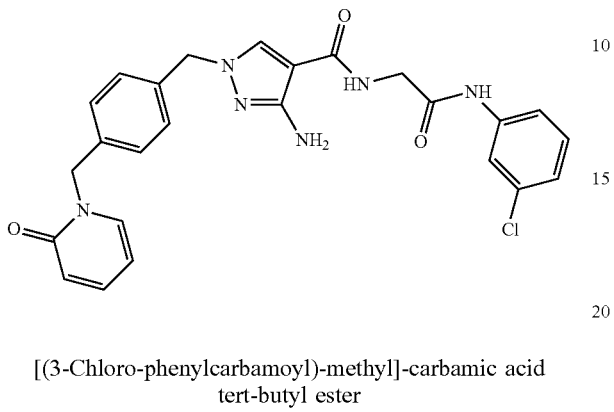

[(3-Chloro-phenylcarbamoyl)-methyl]-carbamic acid tert-butyl ester

Boc-Gly-OH (1.0 g, 5.71 mmol) was dissolved in DCM (50 mL). PyBrop (3.2 g, 6.85 mmol) was added followed by triethylamine (1.44 g, 14.27 mmol). After 20 mins 4-chloroaniline (873 mg, 6.85 mmol) was added. The reaction mixture was stirred at rt for 18 hrs. The reaction mixture was diluted with CHCl₃ (200 mL), washed with 0.3M KHSO₄ (50 mL), sat. NaHCO₃ (aq) (50 mL), water (50 mL) and brine (50 mL), dried (Na₂SO₄) and evaporated in vacuo. The residue was purified by flash chromatography (silica), eluent 60% EtOAc/40% Pet. Ether to give a white solid identified as [(3-chloro-phenylcarbamoyl)-methyl]-carbamic acid tert-butyl ester (800 mg, 2.81 mmol, 49%).

$[MH]^+$=285.1.

2-Amino-N-(3-chloro-phenyl)-acetamide hydrochloride

[(3-Chloro-phenylcarbamoyl)-methyl]-carbamic acid tert-butyl ester (360 mg, 1.26 mmol) was dissolved in 4M HCl in dioxan (40 mL). After 2 hrs at room temperature the solvent was removed in vacuo to give a pale yellow solid identified as 2-amino-N-(3-chloro-phenyl)-acetamide hydrochloride (270 mg, 1.22 mmol, 97%).

$[MH]^+$=185.2.

3-Amino-1-[4-(2-oxo-2H-pyridin-1-ylmethyl)-benzyl]-1H-pyrazole-4-carboxylic acid [(3-chloro-phenylcarbamoyl)-methyl]-amide 3-Amino-1-[4-(2-oxo-2H-pyridin-1-ylmethyl)-benzyl]-1H-pyrazole-4-carboxylic acid (60 mg, 0.19 mmol) was dissolved in DCM (20 mL) and DMF (1 ml). This solution was cooled to 0° C. 2-Amino-N-(3-chloro-phenyl)-acetamide hydrochloride (49 mg, 0.22 mmol) was added followed by HOBt (27 mg, 0.20 mmol) and triethylamine (560 mg, 0.56 mmol). Water soluble carbodiimide (43 mg, 0.228 mmol) was then added. The mixture was allowed to warm to rt and after 18 hrs the mixture was diluted with chloroform (200 mL) and washed with sat. NaHCO₃ (aq) (50 mL), water (50 mL) and brine (50 mL), dried (Na₂SO₄) and evaporated in vacuo. The residue was purified by flash chromatography (silica), eluent 4% MeOH/96% CHCl₃ to give a white solid identified as 3-amino-1-[4-(2-oxo-2H-pyridin-1-ylmethyl)-benzyl]-1H-pyrazole-4-carboxylic acid [(3-chloro-phenylcarbamoyl)-methyl]-amide] (12 mg, 0.024 mmol, 13%).

$[MH]^+$=491.1.

¹H NMR: (d6-DMSO) δ: 3.69 (2H, s), 3.93 (2H, d, J=5.8 Hz), 5.08 (4H, s), 6.22-6.25 (1H, m), 6.41 (1H, t, J=9.1 Hz), 7.09-7.12 (1H, m), 7.22 (2H, d, J=8.2 Hz), 7.27 (2H, d, J=8.2 Hz), 7.32-7.41 (1H, m), 7.45-7.47 (2H, m), 7.77-7.81 (2H, m), 8.03 (1H, s), 8.23 (1H, t, J=5.9 Hz), 10.20 (1H, s).

Example 115

3-Amino-N-[(2S)-2-(3-chlorophenoxy)propyl]-1-({4-[(2-oxopyridin-1-yl)methyl]phenyl}methyl)-pyrazole-4-carboxamide

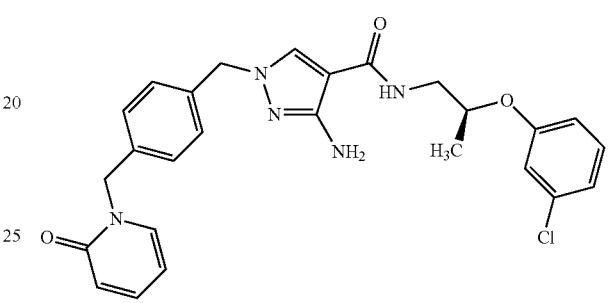

3-Amino-1-(6-pyrrolidin-1-yl-pyridin-3-ylmethyl)-1H-pyrazole-4-carboxylic acid ethyl ester To a suspension of 3-amino-1-(6-fluoro-pyridin-3-ylmethyl)-1H-pyrazole-4-carboxylic acid ethyl ester (115 mg, 0.44 mmol) in 1,4-dioxane (1 mL) was added pyrrolidine (0.36 mL, 4.35 mmol) and the reaction stirred at reflux. The volatiles were removed and the crude residue purified by automated flash chromatography eluting with a mixture of ethyl acetate and acetonitrile (1:1 ratio) in petroleum ether. The title product was isolated as a colourless oil (49 mg, 36% yield).

$[MH]^+$=315.9.

3-Amino-1-(6-pyrrolidin-1-yl-pyridin-3-ylmethyl)-1H-pyrazole-4-carboxylic acid To 3-amino-1-(6-pyrrolidin-1-yl-pyridin-3-ylmethyl)-1H-pyrazole-4-carboxylic acid ethyl ester (49 mg, 0.16 mmol) in ethanol (15 mL) was added sodium hydroxide (62 mg, 1.55 mmol) and the reaction heated at vigorous reflux. Upon completion the reaction mixture was cooled and concentrated under vacuum. The residue was diluted with water (1 mL) and adjusted to pH 5 with a solution of 2M HCl. The mixture was then again concentrated to dryness under vacuum. The acidified residue was taken up in 10% isopropanol in chloroform and filtered to remove the insoluble inorganic salts. The filtrate was concentrated to afford the desired product as an off white solid (44 mg, 99% yield).

$[MH]^+$=287.9.

3-Amino-N-[(2S)-2-(3-chlorophenoxy)propyl]-1-({4-[(2-oxopyridin-1-yl)methyl]phenyl}methyl)-pyrazole-4-carboxamide To 3-amino-1-(6-pyrrolidin-1-yl-pyridin-3-ylmethyl)-1H-pyrazole-4-carboxylic acid (44 mg, 0.15 mmol) in DCM (10 mL) was added 2-(3-chlorophenoxy)ethylamine (26 mg, 0.15 mmol) and the reaction mixture cooled to 0° C. HOBt (24.8 mg, 0.18 mmol), EDC (41.1 mg, 0.21 mmol) and triethylamine (107 µL, 0.77 mmol) were added and the reaction mixture stirred at rt for 48 hrs. The reaction mixture was diluted with chloroform (50 mL) and washed with a saturated solution of NaHCO$_3$ (10 mL). The organic layer was dried (MgSO$_4$), filtered and concentrated. The residue was purified by automated flash chromatography eluting with 0-12% methanol in a mixture of ethyl acetate and acetonitrile (1:1 ratio) to afford the title compound as a white solid (23 mg, 34% yield).

[MH]$^+$=492.0.

$^1$H NMR: (d6-DMSO) δ: 1.23 (3H, d, J=6.1 Hz), 3.20-3.26 (1H, m), 3.40-3.46 (1H, m) 4.49-4.56 (1H, m), 5.03 (2H, s), 5.07 (2H, s), 5.35 (2H, s), 6.20-6.24 (1H, m), 6.40 (1H, d, J=8.9 Hz), 6.94-6.97 (2H, m), 7.06 (1H, t, J=2.2 Hz), 7.19 (2H, d, J=8.1 Hz), 7.26 (2H, d, J=9.3 Hz), 7.29 (1H, s), 7.38-7.43 (1H, m), 7.75 (1H, dd, J=6.9, 1.9 Hz), 7.95 (2H, s).

Example 37

N-[2-(3-Chlorophenoxy)ethyl]-3-(methylamino)-1-({4-[(2-oxopyridin-1-yl)methyl]phenyl}methyl)pyrazole-4-carboxamide 3-Amino-1-[4-(2-oxo-2H-pyridin-1-ylmethyl)-benzyl]-1H-pyrazole-4-carboxylic acid [2-(3-chloro-phenoxy)-ethyl]-amide (80 mg, 0.17 mmol) was dissolved in dry DMF (10 mL) under nitrogen. Iodomethane (48 mg, 0.34 mmol) and caesium carbonate (109 mg, 0.34 mmol) were added and the reaction mixture was stirred at rt for 3 hrs after which time the reaction mixture was diluted with EtOAc (100 mL), this solution was washed with water (1×30 mL), brine (1×30 mL), dried (Na$_2$SO$_4$) and filtered through PS paper and evaporated in vacuo. The residue was purified by flash chromatography (silica), eluent gradient from 5% MeOH, 95% chloroform fractions combined and evaporated in vacuo, LCMS indicated not completely pure therefore the residue was further purified by Prep HPLC (Sunfire prep C18 OBD column. 19×250 mm, 10µ). 10 to 90% 0.1% TFA/MeCN into 0.1% TFA/H$_2$O over 35 min at 20 ml/min. Fractions combined and freeze dried to give a white solid identified as the title compound (21 mg, 0.04 mmol, 26% yield).

[MH]$^+$=492.1.

$^1$H NMR: (d6-DMSO) δ: 2.73 (3H, s), 3.48-3.49 (2H, m), 4.04 (2H, t, J=5.7 Hz), 4.25 (2H, dd, J=4.4, 14.2 Hz), 5.07 (2H, s), 5.09 (2H, s), 6.20-6.24 (1H, m), 6.39 (1H, d, J=8.9 Hz), 6.90-6.93 (1H, m), 6.96-7.00 (2H, m), 7.21 (2H, d, J=8.1 Hz), 7.26-7.31 (3H, m), 7.38-7.43 (1H, m), 7.75 (1H, dd, J=1.8, 6.8 Hz), 7.96 (1H, s).

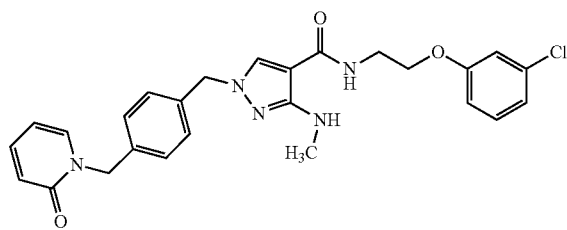 [SMILES: CNc1nn(Cc2ccc(Cn3ccccc3=O)cc2)cc1C(=O)NCCOc1cccc(Cl)c1]

Tabulated Examples

TABLE 1

| Example no. | $G_1$ | $G_2$ | $G_3$ | $G_4$ | $G_5$ | D | E | Free Base MW | [M + H]$^+$ |
|---|---|---|---|---|---|---|---|---|---|
| 3 | NH$_2$ | Cl | H | H | H | CO | NH | 490.9 | 491.0 |
| 4 | NH$_2$ | H | H | Cl | H | CO | NH | 490.9 | 491.1 |
| 5 | cyclopropyl | H | Cl | H | H | CH$_2$ | O | 503.0 | 503.1 |
| 6 | CH$_2$OMe | Cl | H | H | H | CH$_2$ | O | 507.0 | 507.0 |
| 7 | CF$_3$ | H | Cl | H | H | CH$_2$ | O | 530.9 | |

TABLE 1-continued

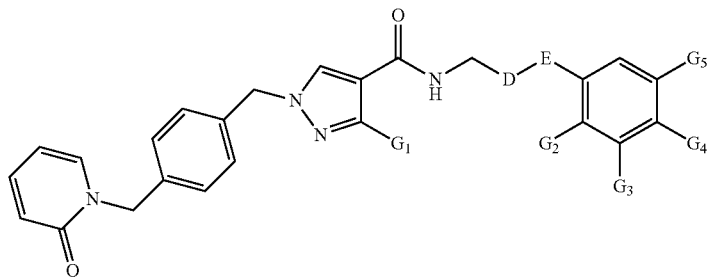

| Example no. | $G_1$ | $G_2$ | $G_3$ | $G_4$ | $G_5$ | D | E | Free Base MW | $[M + H]^+$ |
|---|---|---|---|---|---|---|---|---|---|
| 8 | $CH_2OMe$ | H | Cl | H | H | $CH_2$ | O | 507.0 | 507.0 |
| 9 | $CH_2OMe$ | F | H | H | Cl | $CH_2$ | O | 525.0 | 524.9 |
| 10 | $CH_2OMe$ | H | Cl | H | F | $CH_2$ | O | 525.0 | 525.0 |
| 11 | $CH_2OMe$ | H | Cl | H | OMe | $CH_2$ | O | 537.0 | 537.0 |
| 12 | $CH_2OMe$ | H | Cl | F | H | $CH_2$ | O | 525.0 | 525.0 |
| 14 | $NH_2$ | Me | H | H | Cl | $CH_2$ | O | 492.0 | 492.0 |
| 15 | $NH_2$ | H | Cl | Me | H | $CH_2$ | O | 492.0 | 492.0 |
| 29 | $NH_2$ | Cl | Cl | H | H | $CH_2$ | O | 512.4 | 513.9 |
| 30 | $NH_2$ | H | Cl | Cl | H | $CH_2$ | O | 512.4 | 513.9 |
| 31 | $NH_2$ | H | Cl | H | Cl | $CH_2$ | O | 512.4 | 512.0 |
| 32 | $NH_2$ | CN | H | H | Cl | $CH_2$ | O | 503.0 | 503.1 |
| 33 | $NH_2$ | H | Cl | H | Me | $CH_2$ | O | 492.0 | 492.1 |
| 34 | $NH_2$ | Cl | H | H | Cl | $CH_2$ | O | 512.4 | 514.0 |
| 35 | $NMe_2$ | H | Cl | H | H | $CH_2$ | O | 506.0 | 506.1 |
| 36 | H | H | Cl | H | H | $CH_2$ | O | 462.9 | 463.0 |
| 37 | NHMe | H | Cl | H | H | $CH_2$ | O | 492.0 | 492.1 |
| 38 | CN | H | Cl | H | H | $CH_2$ | O | 487.9 | 487.9 |
| 39 | Me | H | Cl | H | H | $CH_2$ | O | 477.0 | 477.0 |
| 40 | $NH_2$ | H | Cl | H | H | CO | NMe | 505.0 | 505.1 |
| 41 | $NH_2$ | H | Cl | H | H | $CH_2$ | NMe | 491.0 | 491.1 |
| 42 | $NH_2$ | H | Cl | H | H | $CH_2$ | $CH_2$ | 476.0 | 476.0 |

TABLE 2

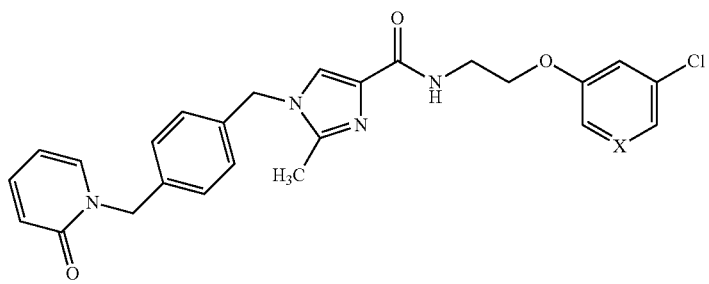

| Example no. | X | Free Base MW | $[M + H]^+$ |
|---|---|---|---|
| 16 | N | 477.9 | |
| 43 | $CH_2$ | 477.0 | 476.9 |

TABLE 3

Core structure: 5-amino-1-(A-CH2)-pyrazole-4-carboxamide-N-ethyl-O-(3-chlorophenyl)

| Example no. | A | Free Base MW | [M + H]+ |
|---|---|---|---|
| 17 | 4-((2-oxopyridin-1(2H)-yl)methyl)phenyl | 477.9 | 477.9 |
| 44 | 1H-indazol-5-yl | 410.9 | 410.9 |
| 45 | 4-(pyrrolidine-1-carbonyl)phenyl | 468.0 | 468.0 |

TABLE 4

Core structure: 1-(4-((2-oxopyridin-1(2H)-yl)methyl)benzyl)-3-G1-pyrazole-4-carboxamide-N-CH2CH2-E-B

| Example no. | G1 | E | B | Free Base MW | [M + H]+ |
|---|---|---|---|---|---|
| 18 | NH2 | O | 5-chloropyridin-3-yl | 478.9 | |
| 19 | CH2OMe | CH2 | 5-chloro-2-oxopyrimidin-1(2H)-yl | 523.0 | |
| 20 | CH2OMe | CH2 | 5-chlorothiazol-2-yl | 512.0 | |
| 21 | NH2 | CH2 | 4-chloro-1H-pyrazol-1-yl | 465.9 | 465.9 |
| 22 | NH2 | O | 4-chloro-1H-pyrazol-3-yl | 467.9 | |
| 23 | CH2OMe | O | 5-chlorothiazol-2-yl | 514.0 | |
| 24 | CH2OMe | CH2 | 5-chloroisoxazol-3-yl | 496.0 | |
| 25 | CH2OMe | S | 4-chlorothiophen-2-yl | 529.1 | |
| 26 | CH2OMe | S | 4-chlorofuran-2-yl | 513.0 | |
| 46 | CH2OMe | O | 5-chloropyridazin-3-yl | 509.0 | 509.0 |

TABLE 4-continued
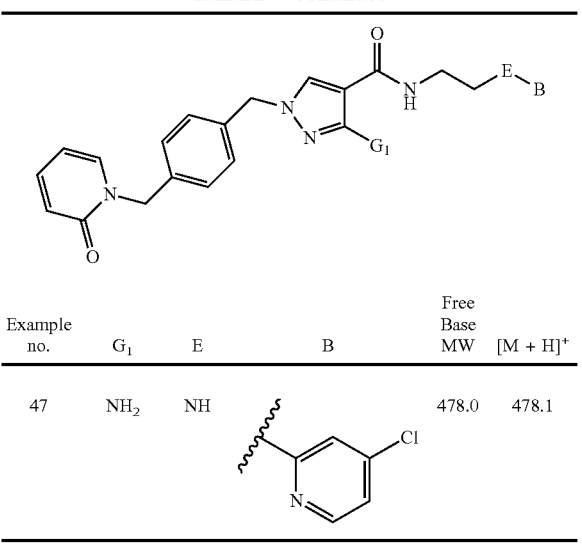
| Example no. | G₁ | E | B | Free Base MW | [M + H]⁺ |
|---|---|---|---|---|---|
| 47 | NH₂ | NH | | 478.0 | 478.1 |
TABLE 6
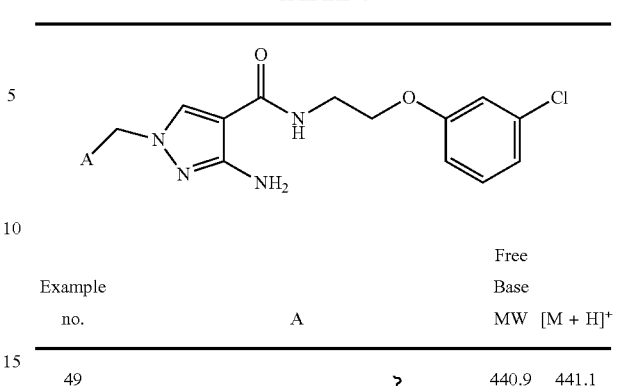
| Example no. | A | Free Base MW | [M + H]⁺ |
|---|---|---|---|
| 49 | | 440.9 | 441.1 |
TABLE 5
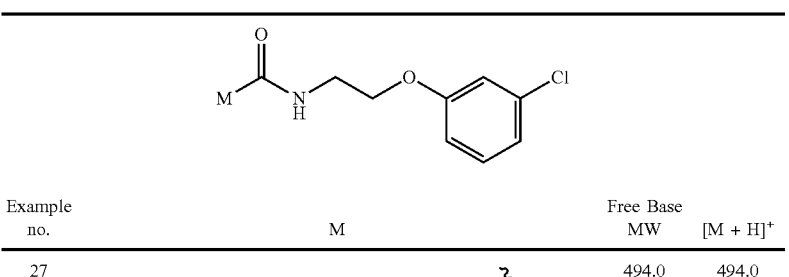
| Example no. | M | Free Base MW | [M + H]⁺ |
|---|---|---|---|
| 27 | 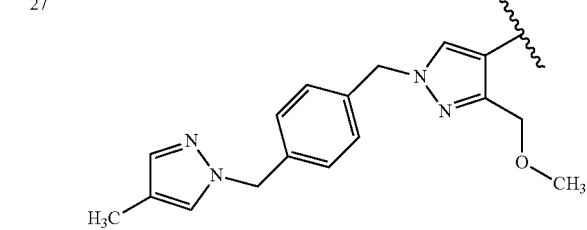 | 494.0 | 494.0 |
| 48 | 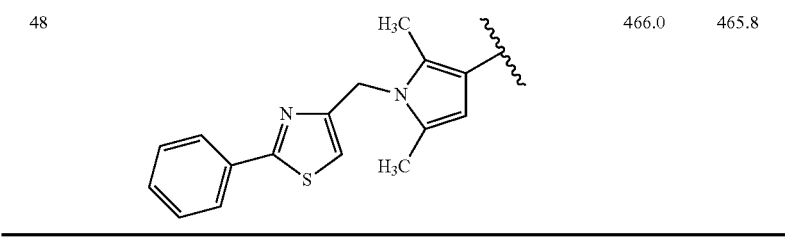 | 466.0 | 465.8 |

TABLE 6-continued

| Example no. | A | Free Base MW | [M + H]+ |
|---|---|---|---|
| 50 | 2-(pyrrolidin-1-yl)pyridin-4-yl | 440.9 | 441.0 |
| 51 | 4-(pyrrolidine-1-carbonyl)phenyl | 468.0 | 468.0 |
| 52 | 4-(2-oxopyridin-1(2H)-yl)phenyl | 463.9 | 464.0 |
| 53 | 6-(pyrrolidin-1-yl)pyridin-2-yl | 440.9 | 441.0 |
| 54 | 2-methylquinolin-6-yl | 435.9 | 435.9 |
| 55 | 4-bromophenyl | 449.7 | 449.1 |
| 56 | 3-bromophenyl | 449.7 | 449.1 |
| 57 | 3-(thiazol-5-yl)phenyl | 453.9 | 454.1 |
| 58 | 4-(methoxycarbonyl)phenyl | 428.9 | 429.2 |
| 59 | 4-(N,N-dimethylcarbamoyl)phenyl | 441.9 | 442.2 |
| 60 | 4-(piperidine-1-carbonyl)phenyl | 482.0 | 482.2 |
| 61 | 4-(methylcarbamoyl)phenyl | 427.9 | 428.2 |
| 62 | 3-(ethoxycarbonyl)phenyl | 442.9 | 443.0 |
| 63 | 3-carboxyphenyl | 414.8 | 414.9 |
| 64 | 3-(methylcarbamoyl)phenyl | 427.9 | 428.2 |

TABLE 6-continued

| Example no. | A | Free Base MW | [M + H]+ |
|---|---|---|---|
| 65 | N,N-dimethylbenzamide (3-position) | 441.9 | 442.2 |
| 66 | 2-(1H-pyrazol-1-yl)pyridin-4-yl | 437.9 | 438.1 |
| 67 | 2-[methyl(carboxymethyl)amino]pyridin-4-yl | 458.9 | 459.2 |
| 68 | 2-[(methylcarbamoylmethyl)amino]pyridin-4-yl | 457.9 | 458.1 |
| 69 | 4-carboxyphenyl | 414.8 | 415.2 |
| 70 | 3-(pyrrolidin-1-ylcarbonyl)phenyl | 468.0 | 468.0 |
| 71 | 4-phenoxyphenyl | 462.9 | 462.9 |
| 72 | 6-phenylpyridin-2-yl | 447.9 | 448.0 |
| 73 | 2-methoxypyridin-4-yl | 401.9 | 402.2 |
| 74 | 2-[methyl(methylcarbamoylmethyl)amino]pyridin-4-yl | 471.9 | 472.2 |
| 75 | 4-[(pyrimidin-2-yloxy)methyl]phenyl | 478.9 | 479.2 |
| 76 | 4-[(3-oxomorpholin-4-yl)methyl]phenyl | 484.0 | 484.2 |
| 77 | 4-[(2-oxopiperidin-1-yl)methyl]phenyl | 482.0 | 482.2 |
| 78 | 4-[(methylcarbamoylmethyl)amino]phenyl | 457.9 | 458.2 |
| 79 | 4-(pyrimidin-2-yl)phenyl | 448.9 | 449.1 |
| 80 | 3-phenyl-1,2,4-oxadiazol-5-yl | 438.9 | 439.2 |

TABLE 6-continued

| Example no. | A | Free Base MW | [M + H]+ |
|---|---|---|---|
| 81 | 6-chloropyridin-2-yl | 406.3 | 406.1 |
| 82 | 4-(N-methylacetamidomethyl)phenyl | 455.9 | 456.2 |
| 83 | 4-((3,3-dimethylureido)methyl)phenyl with N-methyl | 485.0 | 485.2 |
| 84 | 4-(N-methylisobutyramidomethyl)phenyl | 484.0 | 484.0 |
| 85 | 4-((3-methyl-2-oxopyridin-1(2H)-yl)methyl)phenyl | 492.0 | 492.2 |
| 86 | 4-((2-oxopyrimidin-1(2H)-yl)methyl)phenyl | 478.9 | 479.2 |
| 87 | 4-((methyl(pyridin-2-yl)amino)methyl)phenyl | 491.0 | 491.3 |
| 88 | 6-(1H-pyrazol-1-yl)pyridin-3-yl | 437.9 | 438.2 |
| 89 | 6-(4-methyl-1H-pyrazol-1-yl)pyridin-3-yl | 451.9 | 452.2 |

TABLE 6-continued

| Example no. | A | Free Base MW | [M + H]+ |
|---|---|---|---|
| 90 | 3-benzyl-1,2,4-oxadiazol-5-yl | 452.9 | 453.0 |
| 91 | 2,3'-bipyridin-4-yl | 448.9 | 449.0 |
| 92 | 1H-indazol-5-yl | 410.9 | 410.9 |
| 93 | 1-methyl-1H-indazol-5-yl | 424.9 | 424.9 |
| 94 | 2-(2-oxopyrrolidin-1-yl)pyridin-4-yl | 454.9 | 455.7 |
| 95 | 1,2-dimethyl-1H-benzimidazol-5-yl | 438.9 | 439.0 |

TABLE 6-continued

Structure: pyrazole-4-carboxamide with A-CH2- on N1, 3-NH2, N-(2-(3-chlorophenoxy)ethyl)

| Example no. | A | Free Base MW | [M + H]+ |
|---|---|---|---|
| 96 | 5-(2-oxopyrrolidin-1-yl)pyridin-2-yl | 454.9 | 455.1 |
| 97 | [2,3'-bipyridin]-5-yl | 448.9 | 449.0 |
| 98 | 3-methoxy-4-((2-oxopyridin-1(2H)-yl)methyl)phenyl | 508.0 | 508.2 |
| 99 | 4-((2-fluoro-6-oxopyridin-1(6H)-yl)methyl)phenyl | 495.9 | 496.2 |
| 100 | 4-((3-fluoro-2-oxopyridin-1(2H)-yl)methyl)phenyl | 495.9 | 496.2 |

TABLE 6-continued

| Example no. | A | Free Base MW | [M + H]+ |
|---|---|---|---|
| 101 | 2-fluoro-4-((2-oxopyridin-1(2H)-yl)methyl)phenyl | 495.9 | 496.0 |
| 102 | 6-((2-oxopyridin-1(2H)-yl)methyl)pyridin-3-yl | 478.9 | 478.9 |

TABLE 7

Structure: 1-((6-(pyrrolidin-1-yl)pyridin-3-yl)methyl)-3-(trifluoromethyl)-N-(2-(3-chlorophenoxy)ethyl)-1H-pyrazole-4-carboxamide

| Example no. | Free Base MW | [M + H]+ |
|---|---|---|
| 28 | 493.9 | 493.9 |

TABLE 8

Structure: 3,5-dimethyl-1-(4-((2-oxopyridin-1(2H)-yl)methyl)benzyl)-N-(2-(3-chlorophenoxy)ethyl)-1H-pyrazole-4-carboxamide

| Example no. | Free Base MW | [M + H]+ |
|---|---|---|
| 103 | 491.0 | 491.2 |

TABLE 9

| Example no. | Free Base MW | [M + H]⁺ |
|---|---|---|
| 104 | 521.0 | 521.2 |

TABLE 10

| Example no. | Free Base MW | [M + H]⁺ |
|---|---|---|
| 119 | 510.0 | 510.0 |

TABLE 11

| Example no. | ⸺NH–U–D–E–B | Free Base MW | [M + H]⁺ |
|---|---|---|---|
| 105 | (3-chlorophenyl)-pyrrolidin-3-ylamino | 503.0 | 503.1 |
| 106 | (3-chlorophenyl)-pyrrolidin-3-ylamino (enantiomer) | 503.0 | 503.1 |
| 107 | 1-(3-chlorophenyl)-2-oxopyrrolidin-3-ylamino | 517.0 | 517.1 |
| 108 | 1-(3-chlorobenzyl)-pyrrolidin-3-ylamino | 517.0 | 517.1 |

TABLE 11-continued

| Example no. | ⸨NH-U-D-E-B | Free Base MW | [M + H]+ |
|---|---|---|---|
| 109 | (3-chlorobenzyl)pyrrolidin-3-ylamino | 517.0 | 517.2 |
| 110 | 1-(3-chlorophenyl)-5-oxopyrrolidin-3-ylamino | 517.0 | 517.1 |
| 111 | 1-(3-chlorophenyl)-2-oxopyrrolidin-4-ylamino | 517.0 | 517.1 |
| 112 | 1-(4-chloropyridin-2-yl)pyrrolidin-3-ylamino | 504.0 | 504.1 |
| 113 | (S)-2-(3-chlorophenoxy)-1-methylethylamino | 492.0 | 492.1 |
| 114 | (R)-2-(3-chlorophenoxy)-1-methylethylamino | 492.0 | 492.1 |
| 115 | (R)-2-(3-chlorophenoxy)propylamino | 492.0 | 492.0 |
| 116 | (S)-N-(3-chlorophenyl)-N-methyl-2-aminopropanamide | 519.0 | 519.1 |
| 117 | (R)-N-(3-chlorophenyl)-N-methyl-2-aminopropanamide | 519.0 | 519.1 |
| 118 | (±)-2-(3-chlorophenoxy)propylamino | 492.0 | 492.1 |

TABLE 12

Compound names

| Example Number | Name |
|---|---|
| 3 | 2-{[3-amino-1-({4-[(2-oxopyridin-1-yl)methyl]phenyl}methyl)pyrazol-4-yl]formamido}-N-(2-chlorophenyl)acetamide |
| 4 | 2-{[3-amino-1-({4-[(2-oxopyridin-1-yl)methyl]phenyl}methyl)pyrazol-4-yl]formamido}-N-(4-chlorophenyl)acetamide |
| 5 | N-[2-(3-chlorophenoxy)ethyl]-3-cyclopropyl-1-({4-[(2-oxopyridin-1-yl)methyl]phenyl}methyl)pyrazole-4-carboxamide |
| 6 | N-[2-(2-chlorophenoxy)ethyl]-3-(methoxymethyl)-1-({4-[(2-oxopyridin-1-yl)methyl]phenyl}methyl)pyrazole-4-carboxamide |
| 7 | N-[2-(3-chlorophenoxy)ethyl]-1-({4-[(2-oxopyridin-1-yl)methyl]phenyl}methyl)-3-(trifluoromethyl)pyrazole-4-carboxamide |
| 8 | N-[2-(3-chlorophenoxy)ethyl]-3-(methoxymethyl)-1-({4-[(2-oxopyridin-1-yl)methyl]phenyl}methyl)pyrazole-4-carboxamide |
| 9 | N-[2-(5-chloro-2-fluorophenoxy)ethyl]-3-(methoxymethyl)-1-({4-[(2-oxopyridin-1-yl)methyl]phenyl}methyl)pyrazole-4-carboxamide |
| 10 | N-[2-(3-chloro-5-fluorophenoxy)ethyl]-3-(methoxymethyl)-1-({4-[(2-oxopyridin-1-yl)methyl]phenyl}methyl)pyrazole-4-carboxamide |

TABLE 12-continued

Compound names

| Example Number | Name |
|---|---|
| 11 | N-[2-(3-chloro-5-methoxyphenoxy)ethyl]-3-(methoxymethyl)-1-({4-[(2-oxopyridin-1-yl)methyl]phenyl}methyl)pyrazole-4-carboxamide |
| 12 | N-[2-(3-chloro-4-fluorophenoxy)ethyl]-3-(methoxymethyl)-1-({4-[(2-oxopyridin-1-yl)methyl]phenyl}methyl)pyrazole-4-carboxamide |
| 14 | 3-amino-N-[2-(5-chloro-2-methylphenoxy)ethyl]-1-({4-[(2-oxopyridin-1-yl)methyl]phenyl}methyl)pyrazole-4-carboxamide |
| 15 | 3-amlno-N-[2-(3-chloro-4-methylphenoxy)ethyl]-1-({4-[(2-oxopyridin-1-yl)methyl]phenyl}methyl)pyrazole-4-carboxamide |
| 29 | 3-amino-N-[2-(2,3-dichlorophenoxy}ethyl]-1-({4-[(2-oxopyridin-1-yl)methyl]phenyl}methyl)pyrazole-4-carboxamide |
| 30 | 3-amino-N-[2-(3,4-dichlorophenoxy}ethyl]-1-({4-[(2-oxopyridin-1-yl)methyl]phenyl}methyl)pyrazole-4-carboxamide |
| 31 | 3-amino-N-[2-(3,5-dichlorophenoxy)ethyl]-1-({4-[(2-oxopyridin-1-yl)methyl]phenyl}methyl)pyrazole-4-carboxamide |
| 32 | 3-amino-N-[2-(5-chloro-2-cyanophenoxy)ethyl]-1-({4-[(2-oxopyridin-1-yl)methyl]phenyl}methyl)pyrazole-4-carboxamide |
| 33 | 3-amino-N-[2-(3-chloro-5-methylphenoxy)ethyl]-1-({4-[(2-oxopyridin-1-yl)methyl]phenyl}methyl)pyrazole-4-carboxamide |
| 34 | 3-amino-N-[2-(2,5-dichlorophenoxy)ethyl]-1-({4-[(2-oxopyridin-1-yl)methyl]phenyl}methyl)pyrazole-4-carboxamide |
| 35 | N-[2-(3-chlorophenoxy)ethyl]-3-(dimethylamino)-1-({4-[(2-oxopyridin-1-yl)methyl]phenyl}methyl)pyrazole-4-carboxamide |
| 36 | N-[2-(3-chlorophenoxy)ethyl]-1-({4-[(2-oxopyridin-1-yl)methyl]phenyl}methyl)pyrazole-4-carboxamide |
| 37 | N-[2-(3-chlorophenoxy)ethyl]-3-(methylamino)-1-({4-[(2-oxopyridin-1-yl)methyl]phenyl}methyl)pyrazole-4-carboxamide |
| 38 | N-[2-(3-chlorophenoxy)ethyl]-3-cyano-1-({4-[(2-oxopyridin-1-yl)methyl]phenyl}methyl)pyrazole-4-carboxamide |
| 39 | N-[2-(3-chlorophenoxy)ethyl]-3-methyl-1-({4-[(2-oxopyridin-1-yl)methyl]phenyl}methyl)pyrazole-4-carboxamide |
| 40 | 2-{[3-amino-1-({4-[(2-oxopyridin-1-yl)methyl]phenyl}methyl)pyrazol-4-yl]formamido}-N-(3-chlorophenyl)-N-methylacetamide |
| 41 | 3-amino-N-{2-[(3-chlorophenyl)(methyl)amino]ethyl}-1-({4-[(2-oxopyridin-1-yl)methyl]phenyl}methyl)pyrazole-4-carboxamide |
| 42 | 3-amino-N-[3-(3-chlorophenyl)propyl]-1-({4-[(2-oxopyridin-1-yl)methyl]phenyl}methyl)pyrazole-4-carboxamide |
| 16 | N-{2-[(5-chloropyridin-3-yl)oxy]ethyl}-2-methyl-1-({4-[(2-oxopyridin-1-yl)methyl]phenyl}methyl)imidazole-4-carboxamide |
| 43 | N-[2-(3-chlorophenoxy)ethyl]-2-methyl-1-({4-[(2-oxopyridin-1-yl)methyl]phenyl}methyl)imidazole-4-carboxamide |
| 17 | 5-amino-N-[2-(3-chlorophenoxy)ethyl]-1-({4-[(2-oxopyridin-1-yl)methyl]phenyl}methyl)pyrazole-4-carboxamide |
| 44 | 5-amino-N-[2-(3-chlorophenoxy)ethyl]-1-(1H-indazol-5-ylmethyl)pyrazole-4-carboxamide |
| 45 | 5-amino-N-[2-(3-chlorophenoxy)ethyl]-1-({4-[(pyrrolidin-1-yl)carbonyl]phenyl}methyl)pyrazole-4-carboxamide |
| 18 | 3-amino-N-{2-[(5-chloropyridin-3-yl)oxy]ethyl}-1-({4-[(2-oxopyridin-1-yl)methyl]phenyl}methyl)pyrazole-4-carboxamide |
| 19 | N-[3-(5-chloro-2-oxopyrimidin-1-yl)propyl]-3-(methoxymethyl)-1-({4-[(2-oxopyridin-1-yl)methyl]phenyl}methyl)pyrazole-4-carboxamide |
| 20 | N-[3-(5-chloro-1,3-thiazol-2-yl)propyl]-3-(methoxymethyl)-1-({4-[(2-oxopyridin-1-yl)methyl]phenyl}methyl)pyrazole-4-carboxamide |
| 21 | 3-amino-N-[3-(4-chloropyrazol-1-yl)propyl]-1-({4-[(2-oxopyridin-1-yl)methyl]phenyl}methyl)pyrazole-4-carboxamide |
| 22 | 3-amino-N-{2-[(4-chloro-1H-pyrazol-3-yl)oxy]ethyl}-1-({4-[(2-oxopyridin-1-yl)methyl]phenyl}methyl)pyrazole-4-carboxamide |
| 23 | N-{2-[(5-chloro-1,3-thiazol-2-yl)oxy]ethyl}-3-(methoxymethyl)-1-({4-[(2-oxopyridin-1-yl)methyl]phenyl}methyl)pyrazole-4-carboxamide |
| 24 | N-[3-(5-chloro-1,2-oxazol-3-yl)propyl]-3-(methoxymethyl)-1-({4-[(2-oxopyridin-1-yl)methyl]phenyl}methyl)pyrazole-4-carboxamide |
| 25 | N-{2-[(4-chlorothiophen-2-yl)sulfanyl]ethyl}-3-(methoxymethyl)-1-({4-[(2-oxopyridin-1-yl)methyl]phenyl}methyl)pyrazole-4-carboxamide |
| 26 | N-{2-[(4-chlorofuran-2-yl)sulfanyl]ethyl}-3-(methoxymethyl)-1-({4-[(2-oxopyridin-1-yl)methyl]phenyl}methyl)pyrazole-4-carboxamide |
| 46 | N-{2-[(5-chloropyridazin-3-yl)oxy]ethyl}-3-(methoxymethyl)-1-({4-[(2-oxopyridin-1-yl)methyl]phenyl}methyl)pyrazole-4-carboxamide |
| 47 | 3-amino-N-{2-[(4-chloropyridin-2-yl)amino]ethyl}-1-({4-[(2-oxopyridin-1-yl)methyl]phenyl}methyl)pyrazole-4-carboxamide |
| 27 | N-[2-(3-chlorophenoxy)ethyl]-3-(methoxymethyl)-1-({4-[(4-methylpyrazol-1-yl)methyl]phenyl}methyl)pyrazole-4-carboxamide |
| 48 | N-[2-(3-chlorophenoxy)ethyl]-2,5-dimethyl-1-[(2-phenyl-1,3-thiazol-4-yl)methyl]pyrrole-3-carboxamide |
| 49 | 3-amino-N-[2-(3-chlorophenoxy)ethyl]-1-{[6-(pyrrolidin-1-yl)pyridin-3-yl]methyl}pyrazole-4-carboxamide |

TABLE 12-continued

Compound names

| Example Number | Name |
|---|---|
| 50 | 3-amino-N-[2-(3-chlorophenoxy)ethyl]-1-{[2-(pyrrolidin-1-yl)pyridin-4-yl]methyl}pyrazole-4-carboxamide |
| 51 | 3-amino-N-[2-(3-chlorophenoxy)ethyl]-1-({4-[(pyrrolidin-1-yl)carbonyl]phenyl}methyl)pyrazole-4-carboxamide |
| 52 | 3-amino-N-[2-(3-chlorophenoxy)ethyl]-1-{[4-(2-oxopyridin-1-yl)phenyl]methyl}pyrazole-4-carboxamide |
| 53 | 3-amino-N-[2-(3-chlorophenoxy)ethyl]-1-{[6-(pyrrolidin-1-yl)pyridin-2-yl]methyl}pyrazole-4-carboxamide |
| 54 | 3-amino-N-[2-(3-chlorophenoxy)ethyl]-1-[(2-methylquinolin-6-yl)methyl]pyrazole-4-carboxamide |
| 55 | 3-amino-1-[(4-bromophenyl)methyl]-N-[2-(3-chlorophenoxy)ethyl]pyrazole-4-carboxamide |
| 56 | 3-amino-1-[(3-bromophenyl)methyl]-N-[2-(3-chlorophenoxy)ethyl]pyrazole-4-carboxamide |
| 57 | 3-amino-N-[2-(3-chlorophenoxy)ethyl]-1-{[3-(1,3-thiazol-5-yl)phenyl]methyl}pyrazole-4-carboxamide |
| 58 | methyl 4-[(3-amino-4-{[2-(3-chlorophenoxy)ethyl]carbamoyl}pyrazol-1-yl)methyl]benzoate |
| 59 | 3-amino-N-[2-(3-chlorophenoxy)ethyl]-1-{[4-(dimethylcarbamoyl)phenyl]methyl}pyrazole-4-carboxamide |
| 60 | 3-amino-N-[2-(3-chlorophenoxy)ethyl]-1-({4-[(piperidin-1-yl)carbonyl]phenyl}methyl)pyrazole-4-carboxamide |
| 61 | 3-amino-N-[2-(3-chlorophenoxy)ethyl]-1-{[4-(methylcarbamoyl)phenyl]methyl}pyrazole-4-carboxamide |
| 62 | ethyl 3-[(3-amino-4-{[2-(3-chlorophenoxy)ethyl]carbamoyl}pyrazol-1-yl)methyl]benzoate |
| 63 | 3-[(3-amino-4-{[2-(3-chlorophenoxy)ethyl]carbamoyl}pyrazol-1-yl)methyl]benzoic acid |
| 64 | 3-amino-N-[2-(3-chlorophenoxy)ethyl]-1-{[3-(methylcarbamoyl)phenyl]methyl}pyrazole-4-carboxamide |
| 65 | 3-amino-N-[2-(3-chlorophenoxy)ethyl]-1-{[3-(dimethylcarbamoyl)phenyl]methyl}pyrazole-4-carboxamide |
| 66 | 3-amino-N-[2-(3-chlorophenoxy)ethyl]-1-{[2-(pyrazol-1-yl)pyridin-4-yl]methyl}pyrazole-4-carboxamide |
| 67 | ({4-[(3-amino-4-{[2-(3-chlorophenoxy)ethyl]carbamoyl}pyrazol-1-yl)methyl]pyridin-2-yl}(methyl)amino)acetic acid |
| 68 | 3-amino-N-[2-(3-chlorophenoxy)ethyl]-1-[(2-{[(methylcarbamoyl)methyl]amino}pyridin-4-yl)methyl]pyrazole-4-carboxamide |
| 69 | 4-[(3-amino-4-{[2-(3-chlorophenoxy)ethyl]carbamoyl}pyrazol-1-yl)methyl]benzoic acid |
| 70 | 3-amino-N-[2-(3-chlorophenoxy)ethyl]-1-({3-[(pyrrolidin-1-yl)carbonyl]phenyl}methyl)pyrazole-4-carboxamide |
| 71 | 3-amino-N-[2-(3-chlorophenoxy)ethyl]-1-[(4-phenoxyphenyl)methyl]pyrazole-4-carboxamide |
| 72 | 3-amino-N-[2-(3-chlorophenoxy)ethyl]-1-[(6-phenylpyridin-2-yl)methyl]pyrazole-4-carboxamide |
| 73 | 3-amino-N-[2-(3-chlorophenoxy)ethyl]-1-[(2-methoxypyridin-4-yl)methyl]pyrazole-4-carboxamide |
| 74 | 3-amino-N-[2-(3-chlorophenoxy)ethyl]-1-[(2-{methyl[(methylcarbamoyl)methyl]amino}pyridin-4-yl)methyl]pyrazole-4-carboxamide |
| 75 | 3-amino-N-[2-(3-chlorophenoxy)ethyl]-1-({4-[(pyrimidin-2-yloxy)methyl]phenyl}methyl)pyrazole-4-carboxamide |
| 76 | 3-amino-N-[2-(3-chlorophenoxy)ethyl]-1-({4-[(3-oxomorpholin-4-yl)methyl]phenyl}methyl)pyrazole-4-carboxamide |
| 77 | 3-amino-N-[2-(3-chlorophenoxy)ethyl]-1-({4-[(2-oxopiperidin-1-yl)methyl]phenyl}methyl)pyrazole-4-carboxamide |
| 78 | 3-amino-N-[2-(3-chlorophenoxy)ethyl]-1-[(6-{[(methylcarbamoyl)methyl]amino}pyridin-3-yl)methyl]pyrazole-4-carboxamide |
| 79 | 3-amino-N-[2-(3-chlorophenoxy)ethyl]-1-{[4-(pyrimidin-2-yl)phenyl]methyl}pyrazole-4-carboxamide |
| 80 | 3-amino-N-[2-(3-chlorophenoxy)ethyl]-1-[(3-phenyl-1,2,4-oxadiazol-5-yl)methyl]pyrazole-4-carboxamide |
| 81 | 3-amino-N-[2-(3-chlorophenoxy)ethyl]-1-[(6-chloropyridin-2-yl)methyl]pyrazole-4-carboxamide |
| 82 | 3-amino-N-[2-(3-chlorophenoxy)ethyl]-1-({4-[(N-methylacetamido)methyl]phenyl}methyl)pyrazole-4-carboxamide |
| 83 | 3-amino-N-[2-(3-chlorophenoxy)ethyl]-1-[(4-{[(dimethylcarbamoyl)(methyl)amino]methyl}phenyl)methyl]pyrazole-4-carboxamide |
| 84 | 3-amino-N-[2-(3-chlorophenoxy)ethyl]-1-({4-[(N,2-dimethylpropanamido)methyl]phenyl}methyl)pyrazole-4-carboxamide |
| 85 | 3-amino-N-[2-(3-chlorophenoxy)ethyl]-1-({4-[(3-methyl-2-oxopyridin-1-yl)methyl]phenyl}methyl)pyrazole-4-carboxamide |
| 86 | 3-amino-N-[2-(3-chlorophenoxy)ethyl]-1-({4-[(2-oxopyrimidin-1-yl)methyl]phenyl}methyl)pyrazole-4-carboxamide |
| 87 | 3-amino-N-[2-(3-chlorophenoxy)ethyl]-1-[(4-{[methyl(pyridin-2-yl)amino]methyl}phenyl)methyl]pyrazole-4-carboxamide |

TABLE 12-continued

Compound names

| Example Number | Name |
|---|---|
| 88 | 3-amino-N-[2-(3-chlorophenoxy)ethyl]-1-{[6-(pyrazol-1-yl)pyridin-3-yl]methyl}pyrazole-4-carboxamide |
| 89 | 3-amino-N-[2-(3-chlorophenoxy)ethyl]-1-{[6-(4-methylpyrazol-1-yl)pyridin-3-yl]methyl}pyrazole-4-carboxamide |
| 90 | 3-amino-1-[(3-benzyl-1,2,4-oxadiazol-5-yl)methyl]-N-[2-(3-chlorophenoxy)ethyl]pyrazole-4-carboxamide |
| 91 | 3-amino-N-[2-(3-chlorophenoxy)ethyl]-1-{[2-(pyridin-3-yl)pyridin-4-yl]methyl}pyrazole-4-carboxamide |
| 92 | 3-amino-N-[2-(3-chlorophenoxy)ethyl]-1-(1H-indazol-5-ylmethyl)pyrazole-4-carboxamide |
| 93 | 3-amino-N-[2-(3-chlorophenoxy)ethyl]-1-[(1-methylindazol-5-yl)methyl]pyrazole-4-carboxamide |
| 94 | 3-amino-N-[2-(3-chlorophenoxy)ethyl]-1-{[2-(2-oxopyrrolidin-1-yl)pyridin-4-yl]methyl}pyrazole-4-carboxamide |
| 95 | 3-amino-N-[2-(3-chlorophenoxy)ethyl]-1-[(1,2-dimethyl-1,3-benzodiazol-5-yl)methyl]pyrazole-4-carboxamide |
| 96 | 3-amino-N-[2-(3-chlorophenoxy)ethyl]-1-{[6-(2-oxopyrrolidin-1-yl)pyridin-3-yl]methyl}pyrazole-4-carboxamide |
| 97 | 3-amino-N-[2-(3-chlorophenoxy)ethyl]-1-{[6-(pyridin-3-yl)pyridin-3-yl]methyl}pyrazole-4-carboxamide |
| 98 | 3-amino-N-[2-(3-chlorophenoxy)ethyl]-1-({3-methoxy-4-[(2-oxopyridin-1-yl)methyl]phenyl}methyl)pyrazole-4-carboxamide |
| 99 | 3-amino-N-[2-(3-chlorophenoxy)ethyl]-1-({4-[(2-fluoro-6-oxopyridin-1-yl)methyl]phenyl}methyl)pyrazole-4-carboxamide |
| 100 | 3-amino-N-[2-(3-chlorophenoxy)ethyl]-1-({4-[(5-fluoro-2-oxopyridin-1-yl)methyl]phenyl}methyl)pyrazole-4-carboxamide |
| 101 | 3-amino-N-[2-(3-chlorophenoxy)ethyl]-1-({2-fluoro-4-[(2-oxopyridin-1-yl)methyl]phenyl}methyl)pyrazole-4-carboxamide |
| 102 | 3-amino-N-[2-(3-chlorophenoxy)ethyl]-1-({5-[(2-oxopyridin-1-yl)methyl]pyridin-2-yl}methyl)pyrazole-4-carboxamide |
| 28 | N-[2-(3-chlorophenoxy)ethyl]-1-{[6-(pyrrolidin-1-yl)pyridin-3-yl]methyl}-3-(trifluoromethyl)pyrazole-4-carboxamide |
| 103 | N-[2-(3-chlorophenoxy)ethyl]-3,5-dimethyl-1-({4-[(2-oxopyridin-1-yl)methyl]phenyl}methyl)pyrazole-4-carboxamide |
| 104 | N-[2-(3-chlorophenoxy)ethyl]-3-(methoxymethyl)-1-({4-[(4-methyl-2-oxopyridin-1-yl)methyl]phenyl}methyl)pyrazole-4-carboxamide |
| 119 | 3-amino-N-[(2S)-2-(3-chlorophenoxy)propyl]-1-({4-[(5-fluoro-2-oxopyridin-1-yl)methyl]phenyl}methyl)pyrazole-4-carboxamide |
| 105 | 3-amino-N-[(3S)-1-(3-chlorophenyl)pyrrolidin-3-yl]-1-({4-[(2-oxopyridin-1-yl)methyl]phenyl}methyl)pyrazole-4-carboxamide |
| 106 | 3-amino-N-[(3R)-1-(3-chlorophenyl)pyrrolidin-3-yl]-1-({4-[(2-oxopyridin-1-yl)methyl]phenyl}methyl)pyrazole-4-carboxamide |
| 107 | 3-amino-N-[(3S)-1-(3-chlorophenyl)-2-oxopyrrolidin-3-yl]-1-({4-[(2-oxopyridin-1-yl)methyl]phenyl}methyl)pyrazole-4-carboxamide |
| 108 | 3-amino-N-[(3R)-1-[(3-chlorophenyl)methyl]pyrrolidin-3-yl]-1-({4-[(2-oxopyridin-1-yl)methyl]phenyl}methyl)pyrazole-4-carboxamide |
| 109 | 3-amino-N-[(3S)-1-[(3-chlorophenyl)methyl]pyrrolidin-3-yl]-1-({4-[(2-oxopyridin-1-yl)methyl]phenyl}methyl)pyrazole-4-carboxamide |
| 110 | 3-amino-N-[(3R)-1-(3-chlorophenyl)-2-oxopyrrolidin-3-yl]-1-({4-[(2-oxopyridin-1-yl)methyl]phenyl}methyl)pyrazole-4-carboxamide |
| 111 | 3-amino-N-[(3S)-1-(3-chlorophenyl)-5-oxopyrrolidin-3-yl]-1-({4-[(2-oxopyridin-1-yl)methyl]phenyl}methyl)pyrazole-4-carboxamide |
| 112 | 3-amino-N-[(3S)-1-(4-chloropyridin-2-yl)pyrrolidin-3-yl]-1-({4-[(2-oxopyridin-1-yl)methyl]phenyl}methyl)pyrazole-4-carboxamide |
| 113 | 3-amino-N-[(2R)-1-(3-chlorophenoxy)propan-2-yl]-1-({4-[(2-oxopyridin-1-yl)methyl]phenyl}methyl)pyrazole-4-carboxamide |
| 114 | 3-amino-N-[(2S)-1-(3-chlorophenoxy)propan-2-yl]-1-({4-[(2-oxopyridin-1-yl)methyl]phenyl}methyl)pyrazole-4-carboxamide |
| 115 | 3-amino-N-[(2S)-2-(3-chlorophenoxy)propyl]-1-({4-[(2-oxopyridin-1-yl)methyl]phenyl}methyl)pyrazole-4-carboxamide |
| 116 | (2S)-2-{[3-amino-1-({4-[(2-oxopyridin-1-yl)methyl]phenyl}methyl)pyrazol-4-yl]formamido}-N-(3-chlorophenyl)-N-methylpropanamide |
| 117 | (2R)-2-{[3-amino-1-({4-[(2-oxopyridin-1-yl)methyl]phenyl}methyl)pyrazol-4-yl]formamido}-N-(3-chlorophenyl)-N-methylpropanamide |
| 118 | 3-amino-N-[(2R/S)-2-(3-chlorophenoxy)propyl]-1-({4-[(2-oxopyridin-1-yl)methyl]phenyl}methyl)pyrazole-4-carboxamide |

TABLE 13

NMR data of examples (solvent d6 DMSO)

| Example Number | Chemical shift |
|---|---|
| 3 | 3.90 (2H, s), 4.02 (2H, d, J = 5.8 Hz), 5.07 (2H, s), 5.09 (2H, s), 6.21-6.25 (1H, m), 6.39 (1H, t, J = 0.7 Hz), 7.17-7.19 (1H, m), 7.21 (2H, d, J = 8.2 Hz), 7.27 (2H, d, J = 8.2 Hz), 7.35 (1H, m), 7.39-7.43 (1H, m), 7.77 (1H, dd, J = 1.9, 6.6 Hz), 7.82 (2H, dd, J = 1.2, 7.31-8.1 Hz), 8.05 (1H, s), 8.35 (H, t, J = 5.0 Hz), 9.51 (1H, s) |
| 4 | 3.76 (2H), 3.92 (2H, d, J = 5.7 Hz), 5.08 (2H, s), 5.09 (2H, s), 6.21-6.25 (1H, m), 6.40 (1H, d, J = 8.9 Hz), 7.22 (2H, d, J = 8.1 Hz), 7.27 (2H, d, J = 8.1 Hz), 7.39-7.44 (3H, m), 7.61-7.63 (2H, m), 7.77-7.79 (1H, m), 8.04 (1H, s), 8.24 (1H, t, J = 5.9 Hz), 10.15 (1H, s) |
| 5 | 0.74-0.78 (2H, m), 0.79-0.84 (2H, m), 2.54-2.61 (1H, m), 3.49-3.52 (2H, m), 4.07 (2H, t, J = 5.8 Hz), 5.06 (2H, s), 5.18 (2H, s), 6.22 (1H, dt, J = 6.6, 1.4Hz), 6.39 (1H, d, J = 8.8 Hz), 6.93 (1H, dd, J = 7.9, 2.5 Hz), 6.98-7.00 (1H, m), 7.03 (1H, t, J = 2.1 Hz), 7.17 (2H, d, J = 8.1 Hz), 7.26 (2H, d, J = 8.1 Hz), 7.30 (1H, t, J = 8.1 Hz), 7.41 (1H, ddd, J = 9.0,6.6, 2.2 Hz), 7.77 (1H, dd, J = 6.9, 2.1 Hz), 8.05 (1H, t, J = 5.5 Hz), 8.07 (1H, s) |
| 6 | 3.30(3H, s), 3.54-3.60(2H, m), 4.14(2H, t, J = 5.3 Hz), 4.52(2H, s), 5.06(2H, s), 5.28(2H, s), 6.20-6.23(1H, m), 6.39(1H, d, J = 9.5 Hz), 6.93-6.97(1H, m), 7.16-7.30(6H, m), 7.38-7.43(2H, m), 7.74(1H, dd, J = 6.8, 1.9 Hz), 8.10(1H, t, J = 5.4 Hz), 8.21(1H, s) |
| 8 | 3.22 (3H, s), 3.53-3.56 (2H, m), 4.08 (2H, t, J = 5.5 Hz), 4.51 (2H, s), 5.06 (2H, s), 5.28 (2H, s), 6.20-6.24 (1H, m), 6.39 (1H, d, J = 8.9 Hz), 6.91-6.94 (1H, m), 6.98-7.00 (1H, m), 7.03 (1H, t, J = 2.2 Hz), 7.24 (2H, q, J = 8.2 Hz), 7.27 (1H, s), 7.28 (2H, d, J = 8.2 Hz), 7.41 (1H, t, 2.4 Hz), 7.75 (1H, dd, J = 1.6, 6.2 Hz), 8.00 (1H, t, J = 5.6 Hz), 8.22 (1H, s) |
| 9 | 3.22(3H, s), 3.54-3.58 (2H, m), 4.16(2H, t, J = 5.5 Hz), 4.51(2H, s), 5.06(2H, s), 5.28 (2H, s), 6.20-6.24(1H, m), 6.39(1H, d, J = 8.9 Hz), 6.98-7.01(1H, m), 7.20-7.28(5H, m), 7.31 (1H, dd, J = 7.5, 2.5 Hz), 7.39-7.43(1H, m), 7.76(1H, dd, J = 6.8, 2.0 Hz), 8.15(1H, t, J = 5.3 Hz), 8.21(1H, s) |
| 10 | 3.25(3H, s), 3.52-3.56 (2H, m), 4.10(2H, t, J = 5.5 Hz), 4.51(2H, s), 5.07(2H, s), 5.28 (2H, s), 6.20-6.24(1H, m), 6.39(1H, d, J = 8.9 Hz), 6.86-6.93(2H, m), 6.97-7.00(1H, m), 7.22(2H, d, J = 8.2 Hz), 7.26(2H , d, J = 8.2 Hz), 7.39-7.43(1H, m), 7.76(1H, dd, J = 6.5, 1.9 Hz), 8.13(1H, t, J = 5.5 Hz), 8.22(1H, s) |
| 11 | 3.23 (3H, s), 3.53 (2H, dd, J = 10.6, 5.2 Hz), 3.74 (3H, s), 4.06 (2H, t, J = 5.6 Hz), 4.51 (2H, s), 5.06 (2H, s), 5.28 (2H, s), 6.22 (1H, td, J = 6.7, 1.3 Hz), 6.39 (1H, d, J = 9.1 Hz), 6.49 (1H, t, J = 2.2 Hz), 6.61 (2H, dt, J = 3.8, 2.0 Hz), 7.21-7.27 (4H, m), 7.38-7.43 (1H, m), 7.75 (1H, dd, J = 6.6, 1.9 Hz), 8.09 (1H, t, J = 5.3 Hz), 8.21 (1H, s) |
| 12 | 3.22 (3H, s), 3.51-3.55 (2H, m), 4.06 (2H, t, J = 5.5 Hz), 4.51 (2H, s), 5.06 (2H, s), 5.28 (2H, s), 6.23 (1H, td, J = 6.6, 1.3 Hz), 6.40 (1H, d, J = 8.8 Hz), 6.94-6.98 (1H, m), 7.18-7.20 (1H, m), 7.21-7.27 (4H, m), 7.33 (1H, t, J = 9.2 Hz), 7.39-7.43 (1H, m), 7.77 (1H, d, J = 6.5, 1.9 Hz), 8.14 (1H, t, J = 5.4 Hz), 8.23 (1H, s) |
| 14 | 2.09 (3H, s), 3.49-3.53 (2H, m), 4.05 (2H, t, J = 5.8 Hz), 5.04 (2H, s), 5,07 (2H, s), 5.35 (2H, s), 6.22 (1H, td, J = 6.7, 1.3 Hz), 6.40 (1H, d, J = 9.0 Hz), 6.88 (1H, dd, J = 8.0, 2.0 Hz), 7.01 (1H, d, J = 2.0 Hz), 7.13 (1H, d, J = 8.0 Hz), 7.18 (2H, d, J = 8.2 Hz), 7.26 (2H, d, J = 8.2 Hz), 7.38-7.43 (1H, m), 7.76 (1H, dd, J = 6.8, 1.8 Hz), 7.92 (1H, s), 7.95 (1H, s) |
| 15 | 2.24 (3H, s), 3.46-3.50 (2H, m), 4.01 (2H, t, J = 5.7 Hz), 5.03 (2H, s), 5.07 (2H, s), 5.37 (2H, s), 6.22 (1H, t, J = 6.7 Hz), 6.40 (1H, d, J = 9.1 Hz), 6.83-6.86 (1H, m), 7.01 (1H, d, J = 2.5 Hz), 7.19 (2H, d, J = 8.0 Hz), 7.22-7.27 (3H, m), 7.38-7.43 (1H, m), 7.75-7.76 (1H, m), 7.96-7.98 (2H, m) |
| 29 | 3.51-3.53 (2H, m), 4.15 (2H, t, J = 5.9 Hz), 5.04 (2H, s), 5.07 (2H, s), 5.36 (2H, s) 6.22 (1H, t, J = 6.6 Hz), 6.40 (1H, d, J = 9.1 Hz), 7.18-7.21 (4H, m), 7.25-7.33 (3H, m), 7.39-7.43 (1H, m), 7.75-7.76 (1H, m), 7.95 (1H, s), 7.98 (1H, t, J = 5.4 Hz) |
| 30 | 3.46-3.51 (2H, m), 4.06 (2H, t, J = 5.7 Hz), 5.04 (2H, s), 5.06 (2H, s), 5.37 (2H, s), 6.20-6.24 (1H, m), 6.40 (1H, d, J = 9.0 Hz), 6.96-6.99 (1H, m), 7.19 (2H, d, J = 8.1 Hz), 7.25- 7.30(3H, m), 7.39-7.43 (1H, m), 7.51 (1H, d, J = 9.0 Hz), 7.76 (1H, dd, J = 6.8, 2.0 Hz), 7.95 (1H, s), 7.98 (1H, t, J = 5.5 Hz) |
| 31 | 3.46-3.50 (2H, m), 3.48 (2H, t, J = 5.6 Hz), 5.03 (2H, s), 5.07 (2H, s), 5.36 (2H, s), 6.22 (1H, td, J = 6.2, 1.2 Hz), 6.39 (1H, d, J = 9.0 Hz), 7.05 (2H, d, J = 1.6 Hz), 7.14 (1H, s), 7.18 (2H, d, J = 8.1 Hz), 7.26 (2H, d, J = 8.1 Hz), 7.38-7.43 (1H, m), 7.76 (1H, dd, J = 6.7, 1.7 Hz), 7.94 (2H, s) |
| 32 | 3.50-3.54 (2H, m), 4.25 (2H, t, J = 5.9 Hz), 5.04 (2H, s), 5.07 (2H, s), 5.35 (2H, s), 6.20-6.24 (1H, m), 6.39 (1H, d, J = 9.3 Hz), 7.18-7.20 (3H, m), 7.25-7.27 (2H, m), 7.40-7.43 (2H, m), 7.45 (1H, d, J = 1.6 Hz), 7.74-7.76 (1H, m), 7.93 (1H, s), 7.98 (1H, t, J = 5.4 Hz) |
| 33 | 2.25 (3H, s), 3.46- 3.50 (2H, m), 4.03 (2H, t, J = 5.8 Hz), 5.03 (2H, s), 5.07 (2H, s), 5.35 (2H, s), 6.20-6.24 (1H, m), 6.40 (1H, d, J = 9.0 Hz), 6.75 (1H, s), 6.81 (2H, d, J = 2.4 Hz), 7.19 (2H, d, J = 8.1 Hz), 7.26 (2H, d, J = 8.1 Hz), 7.38-7.43 (1H, m), 7.74-7.76 (1H, m), 7.95 (2H, s) |
| 34 | 3.48-3.53 (2H, m), 4.16 (2H, t, J = 6.0 Hz), 5.04 (2H, s), 5.07 (2H, s), 5.35 (2H, s), 6.20-6.24 (1H, m), 6.40 (1H, d, J = 8.8 Hz), 7.00-7.03 (1H, m), 7.19 (2H, d, J = 8.1 Hz), 7.26 (2H, d, J = 8.2 Hz), 7.30 (1H, d, J = 2.2 Hz), 7.38-7.45 (2H, m), 7.74-7.76 (1H, m), 7.94 (2H, s) |
| 35 | 2.71 (6H, s), 3.53-3.57 (2H, m), 4.08 (2H, t, J = 5.6 Hz), 5.07 (2H, s), 5.15 (2H, s), 6.20-6.24 (1H, m), 6.39 (1H, d, J = 8.9 Hz), 6.91-6.94 (1H, m), 6.97-7.00 (1H, m), 7.03 (1H, t, J = 2.2 Hz), 7.22-7.31 (5H, m), 7.39-7.43 (1H, m), 7.75 (1H, dd, J = 1.9, 6.8 Hz), 8.00 (1H, t, J = 5.3 Hz), 8.02 (1H, s) |
| 36 | 3.52 (2H, m), 4.07 (2H, t, J = 5.8 Hz), 5.06 (2H, s), 5.30 (2H, s), 6.20-6.23 (1H, m), 6.40 (1H, d, J = 9.1 Hz), 6.91-6.94 (1H, m), 6.97-7.00 (1H, m), 7.03 (1H, t, J = 2.2 Hz), |

TABLE 13-continued

NMR data of examples (solvent d6 DMSO)

| Example Number | Chemical shift |
|---|---|
| | 7.20- 7.31 (5H, m), 7.38-7.43 (1H, m), 7.75 (1H, dd, J = 4.8, 6.7 Hz), 7.85 (1H, s), 8.22 (1H, s), 8.27 (1H, t, J = 5.5 Hz) |
| 37 | 2.73 (3H, s), 3.48-3.49 (2H, m), 4.04 (2H, t, J = 5.7 Hz), 4.25 (2H, dd, J = 4.4, 14.2 Hz), 5.07 (2H, s), 5.09 (2H, s), 6.20-6.24 (1H, m), 6.39 (1H, d, J = 8.9 Hz), 6.90-6.93 (1H, m), 6.96-7.00 (2H, m), 7.21 (2H, d, J = 8.1 Hz), 7.26-7.31 (3H, m), 7.38-7.43 (1H, m), 7.75 (1H, dd, J = 1.8, 6.8 Hz), 7.96 (1H, s) |
| 38 | 3.53-3.56 (2H, m), 4.09 (2H, t, J = 5.6 Hz), 5.08 (2H, s), 5.44 (2H, s), 6.23 (1H, td, J = 1.4, 6.7 Hz), 6.40 (1H, ddd, J = 0.7, 1.4, 9.1 Hz), 6.92 (1H, ddd, J = 0.9, 2.4, 8.4 Hz), 6.99(1H, ddd, J = 0.9, 2.0, 7.9 Hz), 7.02 (1H, t, J = 2.2 Hz), 7.26-7.33 (5H, m), 7.41 (1H, ddd, J = 2.1, 6.6, 9.0 Hz), 7.77 (1H, ddd, J = 0.7, 2.1, 6.8 Hz), 8.45 (1H, s), 8.61 (1H, t, J = 5.5 Hz) |
| 39 | 2.29 (3H, s), 3.51-3.55 (2H, m), 4.06 (2H, t, J = 5.8 Hz), 5.07 (2H, s), 5.21 (2H, s), 6.22 (1H, td, J = 1.4, 6.7 Hz), 6.40 (1H, ddd, J = 0.7, 1.4, 9.2 Hz), 6.92 (1H, ddd, 1 = 0.9, 2.5, 8.4 Hz), 6.98 (1H, ddd, 1 = 0.9, 2.0, 8.0 Hz), 7.02 (1H, t, J = 2.2 Hz), 7.19-7.33 (5H, m), 7.41 (1H, ddd, J = 2.1, 6.6, 8.9 Hz), 7.76 (1H, ddd, J = 0.7, 2.1, 6.8 Hz), 8.03 (1H, t, J = 5.6 Hz), 8.13 (1H, s) |
| 40 | 3.74 (3H, s, br), 4.72 (2H, s, br), 5.06 (2H, s), 5.07 (4H, s), 6.21-6.24 (1H, m), 6.39 (1H, d, J = 9.0 Hz), 7.20 (2H, d, J = 8.2 Hz), 7.27 (2H, d, J = 8.1 Hz), 7.37-7.44 (4H, m), 7.48 (1H, d, J = 8.0 Hz), 7.75-7.77 (1H, m), 7.98 (1H, t, J = 5.4 Hz), 8.03 (1H, s) |
| 41 | 2.90 (3H, s), 3.26-3.28 (2H, m), 3.38-3,42 (2H, m), 5.03 (2H, s), 5.07 (2H, s), 5.34 (2H, s), 6.21-6.24 (1H, m), 6,39 (1H, d, J = 8.9 Hz), 6.58 (1H, dd, J = 1.7, 7.9 Hz), 6.67 (1H, dd, J = 2.2, 8.4 Hz), 6.71 (1H, d, J = 2.0 Hz), 7.11-7.15 (1H, m), 7.18 (2H, d, J = 8.1 Hz), 7.26 (2H, d, J = 8.1 Hz), 7.39-7.43 (1H, m), 7.76 (1H, dd, J = 1.9, 6.8 Hz), 7.84 (2H, s) |
| 42 | 1.72-1.77 (2H, m), 2.60 (2H, t, J = 7.5 Hz), 3.11-3.16 (2H, m), 5.03 (2H, s), 5.07 (2H, s), 5.34 (2H, br s), 6.22 (1H, td, J = 6.7, 1.4 Hz), 6.40 (1H, d, J = 9.0 Hz), 7.17-7.22 (3H, m), 7.24-7.32 (5H, m), 7.38-7.43 (1H, m), 7.74-7.77 (2H, m), 7.93 (1H, s) |
| 43 | 2.45 (3H, s), 3.52-3.57 (2H, m), 4.10 (2H, t, J = 6.1 Hz), 5.07 (2H, s), 5.16 (2H, s), 6.20-6.24 (1H, m), 6.40 (1H, d, J = 9.8 Hz), 6.93 (1H, dd, J = 8.6, 2.4 Hz), 6.98 (1H, dd, J = 8.0, 1.9 Hz), 7.04 (1H, d, J = 2.1 Hz), 7.16 (2H, d, J = 8.1 Hz), 7.27 (2H, d, J = 8.2 Hz), 7.31-7.27 (1H, m), 7.41 (1H, ddd, J = 8.8, 6.6, 2.1 Hz), 7.64 (1H, s), 7.75 (1H, dd, J = 6.9, 1.8 Hz), 7.96 (1H, br s) |
| 17 | 3.49-3.53 (2H, m), 4.07 (2H, t, J = 5.8 Hz), 5.05 (2H, s), 5.09 (2H, s), 6.21-6.24 (1H, m), 6.30 (2H, s), 6.38-6.41 (1H, m), 6.93-6.95 (1H, m), 6.98-7.00 (1H, m), 7.03-7.04 (1H, m),7.09 (2H, d, J = 8.0 Hz), 7.23 (2H, d, J = 8.1 Hz), 7.25-7.32 (1H, m), 7.38-7.43 (1H, m), 7.69 (1H, s), 7.73.7.77 (1H, m). 7.91-7.96 (1H, m) |
| 44 | 3.49-3.53 (2H, m), 4.08 (2H, t, J = 5.8 Hz), 5.26 (2H, s), 6.35 (2H, s), 6.91-7.04 (4H, m), 7.16 (1H, s), 7.27-7.33 (1H, m), 7.69 (1H, d, J = 8.3 Hz), 7.74 (1H, s), 7.93-8.04 (2H, m), 12.94 (1H, s) |
| 45 | 1.77-1.92 (4H, m), 3.36 (2H, t, J = 6.5 Hz), 3.44 (2H, t, J = 6.7 Hz), 3.50-3.54 (2H, m), 4.08 (2H, t, J = 5.9 Hz), 5.18 (2H, s), 6.35 (2H, s), 6.93-6.95 (1H, m), 6.98-7.00 (1H, m), 7.03 (1H, t, J = 2.1 Hz), 7.15 (2H, d, J = 8.2 Hz), 7.30 (2H, t, J = 8.1 Hz), 7.46 (1H, d, J = 8.1 Hz), 7.73 (1H, s), 7.94 (1H, t, J = 5.5 Hz) |
| 18 | 3.49-3.53 (2H, m), 4.15 (2H, t, J = 5,7 Hz), 5.05 (2H, s), 5.07 (2H, s), 6.22 (1H, td, J = 6.7, 1.3 Hz), 6.40 (1H, d, J = 9.0 Hz), 7.18 (2H, d, J = 8.2 Hz), 7.26 (2H, d, J = 8.1 Hz) 7.38- 7.43 (1H, m), 7.62 (1H, t, J = 2.2 Hz), 7.76 (1H, dd, J = 6.8, 1.9 Hz), 7.95 (1H, s), 7.99 (1H, t, J = 5.3 Hz), 8.21 (1H, d, J = 2.0 Hz), 8.30 (1H, d, J = 2.5 Hz) |
| 21 | 1.88-1.93 (2H, m), 3.04-3.13 (2H, m), 4.09 (2H, t, J = 6.9 Hz), 5.03 (2H, s), 5.07 (2H, s), 5.34 (2H, s), 6.20-6.24 (1H, m), 6.40 (1H, d, J = 9.1 Hz), 7.20 (2H, d, J = 9.1 Hz), 7.27 (2H, d, J = 9.1 Hz), 7.39-7.43 (1H, m), 7.52 (1H, s), 7.75-7.80 (2H, m), 7.91 (1H, s), 7.99 (1H, s) |
| 46 | 3.19 (3H, s), 3.46-3.50 (2H, m), 4.28 (2H, t, J = 5.3 Hz), 4.47 (2H, s), 5.06 (2H, s), 5.30 (2H, s), 6.21-6.25 (1H, m), 6.40 (1H, d, J = 8.9 Hz), 6.84 (1H, d, J = 2.3 Hz), 7.22-7.27 (4H, m), 7.39-7.44 (1H, m), 7.56 (1H, s), 7.77 (1H, dd, J = 5.9, 1.9 Hz), 8.36 (1H, s), 8.55 (1H, s) |
| 47 | 3.20-3.30 (4H, m), 5.03 (2H, s), 5.07 (2H, s), 5.34 (2H, br s), 6.22 (1H, td, J = 6.7, 1.3 Hz), 6.39 (1H, d, J = 8.7 Hz), 6.52-6.54 (2H, m), 6.89 (1H, br s), 7,19 (2H, d, J = 8.1 Hz), 7.26 (2H, d, J = 8.1 Hz), 7.39-7.43 (1H, m), 7.76 (1H, dd, J = 6.7, 1.8 Hz), 7.85 (1H, br s), 7.89 (1H, s), 7.92 (1H, d, J = 5.5 Hz) |
| 27 | 1.98(3H, s), 3.22(3H, s), 3.53-3.57 (2H, m), 4.08(2H, t, J = 5.5 Hz), 4.51(2H, s), 5.21 (2H, s), 5.28(2H, s), 6.92-6.94(1H, m), 6.98-7.00(1H, m), 7.03-7.04(1H, m), 7.16-7.23(5H, m), 7.30(1H, t, J = 8.1 Hz), 7.53(1H, s), 8.13(1H, t, J = 5.5 Hz), 8.22(1H, s) |
| 48 | 2.25 (3H, s), 2.55 (3H, s), 3.47-3.52 (2H, m), 4.05 (2H, t, J = 6.1 Hz), 5.16 (2H, s), 6.24 (1H, s), 6.93 (1H, dd, J = 8.7, 2.4 Hz), 6.98 (1H, dd, J = 7.9, 1.7 Hz), 7.03 (1H, dd, J = 2.1, 2.1 Hz), 7.23 (1H, s), 7.29 (1H, dd, J = 8.2, 8.1 Hz), 7.53-7.46 (3H, m), 7.68 (1H, br s), 7.91-7.88 (2H, m) |
| 49 | 1.91-1.94 (4H, m), 3.34-3.37 (4H, m), 3.47 3.50 (2H, m), 4.04 (2H, t, J = 5.8 Hz), 4.88 (2H, s), 5.34 (2H, br s), 6.42 (1H, d, J = 8.6 Hz), 6.91-6.94 (1H, m), 6.97-6.99 (1H, m), 7.01-7.02 (1H, m), 7.29 (1H, t, J = 8.1 Hz), 7.40 (1H, dd, J = 8.6, 2.4 Hz), 7.84 (1H, s), 7.94 (1H, t, J = 5.9 Hz), 8.04 (1H, d, J = 2.2 Hz) |
| 50 | 2.02 (4H, s), 3.52-3.54 (6H, m), 4.08 (2H, t, J = 5.3 Hz), 5.20 (2H, s), 6.51 (1H, d, J = 6.4 Hz), 6.92-7.01 (4H, m), 7.03-7.10 (2H, m), 7.29-7.33 (1H, m), 7.91(1H, d, J = 6.5 Hz), 8.09 (2H, d, J = 0.7 Hz) |
| 51 | 1.77-1.89 (4H, m), 3.43-3.53 (2H, m), 3.59-3.63 (2H, m), 4.07 (2H, t, J = 5.7 Hz), 5.13 (2H, s), 5.41 (2H, s), 6.92-7.05 (4H, m), 7.24-7.32 (4H, m), 7.49 (2H, d, J = 8.2 Hz), 8.02 (2H, s) |

TABLE 13-continued

NMR data of examples (solvent d6 DMSO)

| Example Number | Chemical shift |
|---|---|
| 52 | 3.49 3.53 (2H, m), 4.07 (2H, t, J = 5.8 Hz), 5.15 (2H, s), 5.41 (2H, s), 6.30-6.32 (1H, m), 6.46 (1H, d, J = 9.2 Hz), 6.92-7.04 (3H, m), 7.28-7.39 (5H, m), 7.47-7.52 (1H, m), 7.61 (1H, dd, J = 6.9, 1.9 Hz), 8.03 (1H, t, J = 5.5 Hz), 8.06 (1H, s) |
| 53 | 1.89-1.92 (4H, m), 3.32-3.36 (4H, m), 3.49-3.53 (2H, m), 4.07 (2H, t, J = 5.8 Hz), 4.93 (2H, s), 5.37 (2H, br s), 6.23 (1H, d, J = 7.2 Hz), 6.33 (1H, d, J = 8.4 Hz), 6.93 (1H, dd, J = 8.7, 2.4 Hz), 6.99 (1H, dd, J = 8.1, 1.9 Hz), 7.03 (1H, dd, J = 2.2, 2.0 Hz), 7.28-7.32 (1H, m), 7.42 (1H, dd, J = 8.4, 7.5 Hz), 7.95-8.04 (1H, m), 8.01 (1H, s) |
| 54 | 2.64 (3H, s), 3.48-3.52 (2H, m), 4.06 (2H, t, J = 5.8 Hz), 5.26 (2H, s), 5.40 (2H, s), 6.91-6.94 (2H, m), 6.97-7.00 (1H, m), 7.02 (1H, s), 7.27-7.31 (1H, m), 7.41 (1H, d, J = 8.4 Hz), 7.55 (1H, dd, J = 2.0, 8.6 Hz), 7.75 (1H, d, J = 1.5 Hz), 7.89 (1H, d, J = 8.7 Hz), 7.99 (1H, t, J = 5.5 Hz), 8.22 (1H, d, J = 8.4 Hz) |
| 55 | 3.46-3.57 (2H, m), 4.07 (2H, t, J = 5.8 Hz), 5.08 (2H, s), 6.94 (1H, dd, J = 2.0, 8.0 Hz), 6.98-7.02 (1H, m), 7.02-7.06 (1H, m), 7.17-7.22 (2H, m), 7.28-7.34 (1H, m), 7.54-7.60 (2H, m), 7.99 (1H, s), 8.01-8.08 (1H, m) |
| 56 | 3.50-3.54 (2H, m), 4.08 (2H, t, J = 5.7 Hz), 5.13 (2H, s), 6.90-6.96 (1H, m), 6.98-7.03 (1H, m), 7.04 (1H, t, J = 2.2 Hz), 7.21-7.27 (1H, m), 7.27-7.37 (2H, m), 7.41-7.47 (1H, m), 7.48-7.56 (1H, m), 8.05 (1H, s), 8.09 (1H, t, J = 5.5 Hz) |
| 57 | 3.49-3.52 (2H, m), 4.06 (2H, t, J = 5.7 Hz), 5.14 (2H, s), 5.42 (2H, s), 6.91-6.95 (1H, m), 6.97-7.01 (1H, m), 7.02-7.06 (1H, m), 7.21 (1H, d, J = 7.9 Hz), 7.30 (1H, t, J = 8.2 Hz), 7.45 (1H, t, J = 7.7 Hz), 7.59 (1H, s), 7.64-7.69 (1H, m), 7.99-8.06 (2H, m), 8.30 (1H, s), 9.10 (1H, d, J = 0.6 Hz) |
| 58 | 3.50-3.54 (2H, m), 3.85 (3H, s), 4.07 (2H, t, J = 5.7 Hz), 5.19 (2H, s), 5.43 (2H, s), 6.89-6.96 (1H, m), 6.98-7.02 (1H, m), 7.03-7.05 (1H, m), 7.27-7.37 (3H, m), 7.95 (2H, d, J = 8.4 Hz), 8.00-8.06 (2H, m) |
| 59 | 2.89 (3H, s), 2.97 (3H, s), 3.49-3.53 (2H, m), 4.07 (2H, t, J = 5.7 Hz), 5.13 (2H, s), 5.42 (2H, s), 6.91-6.98 (1H, m), 6.96-7.03 (1H, m), 7.01-7.07 (1H, m), 7.22-7.29 (2H, m), 7.31 (1H, t, J = 8.1 Hz), 7.35-7.42 (2H, m), 7.99-8.06 (2H, m) |
| 60 | 1.41-1.65 (6H, m), 3.16-3.28 (2H, m), 3.47-3.62 (4H, m), 4.07 (2H, t, J = 5.7 Hz), 5.13 (2H, s), 5.42 (2H, s), 6.91-6.97 (1H, m), 6.97-7.02 (1H, m), 7.02-7.06 (1H, m), 7.24-7.37 (5H, m), 8.01-8.06 (2H, m) |
| 61 | 2.78 (3H, d, J = 4.6 Hz), 3.49-3.52 (2H, m), 4.07 (2H, t, J = 5.7 Hz), 5.14 (2H, s), 5.41 (2H, s), 6.91-6.97 (1H, m), 6.98-7.02 (1H, m), 7.04 (1H, t, J = 2.2 Hz), 7.26-7.34 (3H, m), 7.78-7.83 (2H, m), 7.99-8.05 (2H, m), 8.35-8.46 (1H, m) |
| 62 | 1.31 (3H, t, J = 7.1 Hz), 3.48-3.52 (2H, m), 4.06 (2H, t, J = 5.8 Hz), 4.31 (2H, q, J = 7.1 Hz), 5.17 (2H, s), 5.42 (2H, s), 6.93 (1H, ddd, J = 0.9, 2.5, 8.4 Hz), 6.99 (1H, ddd, J = 0.9, 2.0, 7.9 Hz), 7.03 (1H, t, J = 2.2 Hz), 7.30 (1H, t, J = 8.1 Hz), 7.48-7.54 (2H, m), 7.84 (1H, dd, J = 0.9, 1.9 Hz), 7.89 (1H, ddd, J = 1.8, 3,1, 6.1 Hz), 8.02 (2H, d, J = 1.8 Hz) |
| 63 | 3.50-3.51 (2H, m), 4.06 (2H, t, J = 5.8 Hz), 5.16 (2H, s), 5.42 (2H, s, br), 6.93 (1H, dd, J = 2.4, 8.2 Hz), 6.99 (1H, dd, J = 1.9, 7.7 Hz), 7.03 (1H, t, J = 2.2 Hz), 7.30 (1H, t, J = 8.2 Hz), 7.42-7.55 (2H, m), 7.80 (1H, s), 7.87 (1H, ddt, J = 2.8, 5.5, 7.3 Hz), 8.02 (2H, m), 13.01 (1H, s, br) |
| 64 | 2.76 (3H, d, J = 4.5 Hz), 3.48-3.51 (2H, m), 4.06 (2H, t, J = 5.8 Hz), 5.12 (2H, s), 5.40 (2H, s), 6.93 (1H, ddd, J = 0.9, 2.5, 8.4 Hz), 6.99 (1H, ddd, J = 0.8, 2.0, 8.0 Hz), 7.03 (1H, t, J= 2.2 Hz), 7.30 (1H, t, J = 8.1 Hz), 7.35 (1H, dt, J = 1.5, 7.7 Hz), 7.43 (1H, t, J = 7.6 Hz), 7.70-7.78 (2H, m), 8.01 (H, d, J = 8,2 Hz), 8.44 (1H, m) |
| 65 | 2.87 (3H, s), 2.96 (3H, s), 3.48-3.51 (2H, m), 4.06 (2H, t, .1 = 5.8 Hz), 5.12 (2H, s), 5.41 (2H, s), 6.93 (1H, ddd, J = 0.9, 2.5, 8.3 Hz), 6.99 (1H, ddd, J = 0.9, 2.0, 7.9 Hz), 7.03 (1H,t, J = 2.2 Hz), 7.23 (1H, d, J = 1.7 Hz), 7.27-7.34 (3H, m), 7.41 (1H, t, J = 7.6 Hz), 8.02 (2H, m) |
| 66 | 3.50-3.54 (2H, m), 4.08 (2H, t, J = 5.7 Hz), 5.28 (2H, s), 5.48 (2H, s), 6.57 (1H, dd, J = 2.6, 1.7 Hz), 6.94 (1H, dd, J = 8.4, 2.5 Hz), 6.99 (1H, dd, J = 7.9, 2.0 Hz), 7.04 (1H, t, J = 2.2 Hz), 7.14 (1H, dd, J = 5.1, 1.5 Hz), 7.30 (1H, t, J = 8.1 Hz), 7.69 (1H, s), 7.81 (1H, d, J = 1.7 Hz), 8.04-8.12 (2H, m), 8.42 (1H, d, J = 5.0 Hz), 8.60 (1H, d, J = 2.6 Hz) |
| 68 | 2.55 (3H, d, J = 4.7 Hz), 3.49-3.53 (2H, m), 3.77 (2H, d, J = 5.9 Hz), 4.07 (2H, t, J = 5.7 Hz), 4.97 (2H, s), 5.42 (2H, s), 6.27 (1H, s), 6.33 (1H, dd, J = 5.3, 1.5 Hz), 6.86 (1H, t, J = 6.0 Hz), 6.94 (1H, dd, J = 8.4, 2.4 Hz), 6.99 (1H, dd, J = 7.9, 2.0 Hz), 7.03 (1H, t, J = 2.2 Hz), 7.30 (1H, t, J = 8.1 Hz), 7.68-7.69 (1H, m), 7.89 (1H, d, J = 5.3 Hz), 8.00 (1H, s), 8.05 (1H, t, J = 5.6 Hz) |
| 70 | 1.77-1.86 (4H, m), 3.33-3.35 (2H, m), 3.44 (2H, t, J = 6.8 Hz), 3.48-3.53 (2H, m), 4.06 (2H, t, J = 5.8 Hz), 5.13 (2H, s), 5,41 (2H, s br), 6.93 (1H, ddd, J = 0.9, 2.5, 8.4 Hz), 6.99 (1H, ddd, J = 0.8, 1.9, 7.9 Hz), 7.03 (1H, t, J = 2.2 Hz), 7.30 (2H, ddd, J = 3.7, 5.4, 8.2 Hz), 7.34 (1H, d, J = 1.7 Hz), 7.38-7.46 (2H, m), 8.02 (2H, m) |
| 71 | 3.49-3.52 (2H, m), 4.06 (2H, t, J = 5.8 Hz), 5.05 (2H, s), 5.40 (2H, s br), 6.93 (1H, ddd, J = 0.9, 2.5, 8.4 Hz), 6.96-7.01 (5H, m), 7.03 (1H, t, J = 2.2 Hz), 7.11-7.16 (1H, m), 7.24-7.32 (3H, m), 7.35-7.42 (2H, m), 7.98 (1H, s), 8.01 (1H, t, J = 5.6 Hz) |
| 72 | 3.50-3.54 (2H, m), 4.04-4.11 (2H, t, J = 5.7 Hz), 5.25 (2H, s), 5.43 (2H, s br), 6.91-6.96 (1H, ddd, J = 0.9, 2.4, 8.4 Hz), 6.97-7.01 (1H, ddd, J = 0.9, 2.0, 7.9 Hz), 7.03-7.07 (2H, m), 7.26-7.34 (1H, t, J = 8.2 Hz), 7.41-7.51 (3H, m), 7.84-7.91 (2H, m), 8.04-8.10 (3H, m), 8.12-8.15 (1H, s) |
| 73 | 3.49-3.53 (2H, m), 3.82 (3H, s), 4.07 (2H, t, J = 5.8 Hz), 5.10 (2H, s), 5.44 (2H, s), 6.53-6.56 (1H, m), 6.76 (1H, dd, J = 1.4 & 5.3 Hz), 6.94 (1H, ddd, J = 0.8 & 2.5 & 8.4 Hz), 6.99 (1H, ddd, J = 0.8 & 2.0 & 7.9 Hz), 7.04 (1H, t, J = 2.2 Hz), 7.30 (1H, t, J = 8.2 Hz), 8.02 (1H, s), 8.04 (1H, t, J = 5.6 Hz), 8.11 (1H, dd, J = 0.6 & 5.3 Hz). |

TABLE 13-continued

NMR data of examples (solvent d6 DMSO)

| Example Number | Chemical shift |
|---|---|
| 74 | 2.55 (3H, d, J = 4.6 Hz), 2.99 (3H, s), 3.49-3.53 (2H, m), 4.02-4.13 (4H, m), 5.01 (2H, s), 5.41 (2H, s), 6.34 (1H, dd, J = 5.2, 1.3 Hz), 6.49 (1H, s), 6.93 (1H, dd, J = 8.4, 2.5 Hz), 6.99 (1H, dd, J = 7.9, 2.0 Hz), 7.03 (1H, t, J = 2.2 Hz), 7.30 (1H, t, J = 8.1 Hz), 7.71 (1H, q, J = 4.3 Hz), 7.94-8.07 (3H, m) |
| 75 | 3.50 (2H, m), 4.05 (2H, q, J = 5.8 Hz), 5.08 (2H, s), 5.37 (2H, s), 5.39 (2H, s), 6.93 (1H, dd, J = 8.3, 2.5 Hz), 6.99 (1H, dd, J = 7.9, 2.0 Hz), 7.03 (1H, t, J = 2.2 Hz), 7.15 (1H, t, J = 4.8 Hz), 7.24 (2H, d, J = 8.2 Hz), 7.30 (1H, t, J = 8.1 Hz), 7.43 (2H, d, J = 8.1 Hz), 7.97 (1H, s), 8.00 (1H, t, J = 5.6 Hz), 8.61 (2H, d, J = 4.8 Hz) |
| 76 | 3.20-3.26 (2H, m), 3.48-3.52 (2H, m), 3.76-3.83 (2H, m), 4.06 (2H, t, J = 5.8 Hz), 4.10 (2H, s), 4.52 (2H, s), 5.06 (2H, s), 5.39 (2H, s), 6.93 (1H, dd, J = 8.4, 2.4 Hz), 6.99 (1H, dd, J = 7.9, 2.0 Hz), 7.03 (1H, t, J = 2.2 Hz), 7.17-7.28 (4H, m), 7.30 (1H, t, J = 8.1 Hz), 7.95-8.04 (2H, m) |
| 77 | 1.65-1.73 (4H, m), 2.25-2.31 (2H, m) 3.12-3.18 (2H, m), 3.48-3.52 (2H, m), 4.06 (2H, t, J = 5.8 Hz), 4.47 (2H, s), 5.04 (2H, s), 5.38 (2H, s), 6.93 (1H, dd, J = 8.4, 2.5 Hz), 6.99 (1H, dd, J = 7.9, 2.0 Hz), 7.03 (1H, t, J = 2.2 Hz), 7.16-7.22 (4H, m), 7.30 (1H, t, J = 8.1 Hz), 7.96-8.02 (2H, m) |
| 78 | 2.57 (3H, d, J = 4.6 Hz), 3.46-3.52 (2H, m), 3.80 (2H, d, J = 5.9 Hz), 4.05 (2H, t, J = 5.8 Hz), 4.87 (2H, s), 5.37 (2H, s), 6.54 (1H, d, J = 8.6 Hz), 6.88 (1H, t, J = 5.9 Hz), 6.91-6.96 (1H, m), 6.97-7.06 (2H, m), 7.27-7.35 (2H, m), 7.70-7.77 (1H, m), 7.89 (1H, s), 7.95 (1H, d, J = 2.1 Hz), 7.99 (1H, t, J = 5.6 Hz) |
| 79 | 3.49-3.52 (2H, m), 4.07 (2H, t, J = 5.8 Hz), 5.18 (2H, s), 5.43 (2H, s), 6.90-6.96 (1H, m), 6.97-7.02 (1H, m), 7.02-7.05 (1H, m), 7.30 (1H, t, J = 8.2 Hz), 7.37 (2H, d, J = 8.5 Hz), 7.45 (1H, t, J = 4.8 Hz), 8.00-8.07 (2H, m), 8.35-8.41 (2H, m), 8.91 (2H, d, J = 4.9 Hz) |
| 80 | 3.52-3.55 (2H, m), 4.10 (2H, t, J = 5.8 Hz), 5.54 (2H, s), 5.66 (2H, s), 6.93-6.98 (1H, m), 6.98-7.02 (1H, m), 7.05 (1H, t, J = 2.2 Hz), 7.31 (1H, t, J = 8.2 Hz), 7.55-7.62 (3H, m), 7.96-8.03 (2H, m), 8.15-8.22 (2H, m) |
| 81 | 3.50-3.53 (2H, m), 4.06-4.09 (2H, t, J = 5.8 Hz), 5.17 (2H, s), 5.44 (2H, s br), 6.94 (1H, ddd, J = 0.9, 2.5, 8.4 Hz), 6.99 (1H, ddd, J = 0.9, 2.0, 8.0 Hz), 7.03-7.04 (1H, t, J = 2.2 Hz), 7.13 (1H, dd, J = 0.8, 7.6 Hz), 7.28-7.32 (1H, t, J = 8.2 Hz), 7.44-7.46 (1H, dd, J = 0.8, 8.0 Hz), 7.84-7.88 (1H, t, J = 7.8 Hz), 8.07-8.10 (2H, m) |
| 82 | 2.04 (3H, s), 2.88 (3H, br s), 3.49-3.53 (2H, m), 4.11 (2H, t, J = 6.0 Hz), 4.50 (2H, s), 5.05 (2H, s), 5.14 (2H, s), 6.93 (1H, dd, J = 8.3, 2.4 Hz), 6.97 (1H, dd, J = 7.9, 2.0 Hz), 7.01 (1H, t, J = 2.2 Hz), 7.18-7.31 (5H, m), 7.60 (1H, br s), 7.92 (1H, s) |
| 83 | 2.63 (3H, s), 2.73 (6H, s), 3.49-3.53 (2H, m), 4.06 (2H, t, J = 5.8 Hz), 4.26 (2H, s), 5.05 (2H, s), 5.39 (2H, s), 6.93 (1H, dd, J = 8.4, 2.4 Hz), 6.99 (1H, dd, J = 7.9, 2.0 Hz), 7.03 (1H, t, J = 2.2 Hz), 7.16-7.26 (4H, m), 7.30 (1H, t, J = 8.2 Hz), 7.95-8.04 (2H, m) |
| 84 | 1.05 (6H, d, J = 6.7 Hz), 2.85-2.95 (4H, m), 3.48-3.52 (2H, m), 4.11 (2H, t, J = 6.0 Hz), 4.53 (2H, s), 5.04 (2H, s), 5.14 (2H, s), 6.93 (1H, dd, J = 8.3, 2.5 Hz), 6.97 (1H, dd, J = 7.9, 2.0 Hz), 7.00 (1H, t, J = 2.2 Hz), 7.18 (2H, d, J = 8.2 Hz), 7.23 (2H, d, J = 8.2 Hz), 7.28 (1H, t, J = 8.1 Hz), 7.60 (1H, br s), 7.92 (1H, s) |
| 85 | 1.98 (3H, s), 3.47-3.51 (2H, m), 4.05 (2H, t, J = 5.8 Hz), 5.03 (2H, s), 5.07 (2H, s), 5.37 (2H, s), 6.14 (1H, t, J = 6.8 Hz), 6.93 (1H, dd, J = 8.4, 2.5 Hz), 6.99 (1H, dd, J = 7.9, 2.0 Hz), 7.02 (1H, t, J = 2.2 Hz), 7.18 (2H, d, J = 8.2 Hz), 7.23-7.33 (4H, m), 7.63 (1H, dd, J = 6.9, 2.1 Hz), 7.96 (1H, s), 7.98 (1H, t, J = 5.6 Hz) |
| 86 | 3.47-3.52 (2H, m), 4.05 (2H, t, J = 5.8 Hz), 5.03 (2H, s), 5.05 (2H, s), 5.37 (2H, s), 6.45 (1H, dd, J = 6.4, 4.1 Hz), 6.93 (1H, dd, J = 8.4, 2.5 Hz), 6.99 (1H, dd, J = 8.0, 2.0 Hz), 7.03 (1H, t, J = 2.2 Hz), 7.21 (2H, d, J = 8.2 Hz), 7.27-7.33 (3H, m), 7.97 (1H, s), 8.00 (1H, t, J = 5.5 Hz), 8.32 (1H, dd, J = 6.5, 2.8 Hz), 8.55 (1H, dd, J = 4.1, 2.8 Hz) |
| 87 | 3.00 (3H, s), 3.47-3.51 (2H, m), 4.05 (2H, t, J = 5.8 Hz), 4.76 (2H, s), 5.02 (2H, s), 5.37 (2H, s), 6.55 (1H, dd, J = 7.1, 4.9 Hz), 6.60 (1H, d, J = 8.6 Hz), 6.93 (1H, dd, J = 8.4, 2.5 Hz), 6.99 (1H, dd, J = 7.9, 2.0 Hz), 7.02 (1H, t, J = 2.2 Hz), 7.17 (4H, s), 7.29 (1H, t, J = 8.1 Hz), 7.47 (1H, ddd, J = 8.9, 7.1, 2.0 Hz), 7.96 (1H, s), 7.98 (1H, t, J = 5.5 Hz), 8.06 (1H, dd, J = 4.9, 2.0 Hz) |
| 88 | 3.47-3.56 (2H, m), 4.07 (2H, t, J = 5.8 Hz), 5.18 (2H, s), 5.44 (2H, s), 6.58 (1H, dd, J = 1.7, 2.6 Hz), 6.94 (1H, dd, J = 2.0, 8.0 Hz), 6.99 (1H, dd, 1 = 1.1, 7.9 Hz), 7.03 (1H, t, J = 2.2 Hz), 7.30 (1H, t, J = 8.2 Hz), 7.80-7.88 (2H, m), 7.94 (1H, d, J = 8.4 Hz), 7.98-8.06 (2H, m), 8.42 (1H, d, J = 1.7 Hz), 8.61 (1H, dd, J = 0.7, 2.6 Hz) |
| 89 | 2.11 (3H, s), 3.46-3.56 (2H, m), 4.07 (2H, t, J = 5.7 Hz), 5.16 (2H, s), 5.43 (2H, s), 6.94 (1H, dd, J = 2.0, 8.0 Hz), 6.97-7.01 (1H, m), 7.03 (1H, t, J = 2.2 Hz), 7.30 (1H, t, J = 8.2 Hz), 7.64 (1H, s), 7.81 (1H, dd, J = 2.3, 8.5 Hz), 7.85-7.90 (1H, m), 8.01 (2H, s), 8.36-8.40 (2H, m) |
| 90 | 3.50-3.54 (2H, m), 4.04-4.11 (4H, m), 5.50(2H, s), 5.52 (2H, s), 6.94 (1H, dd, J = 8.4, 2.4 Hz), 6.99 (1H, dd, J = 7.9, 2.0 Hz), 7.04 (1H, t, J = 2.2 Hz), 7.22-7.35 (6H, m), 8.10 (1H, s), 8.14 (1H, t, J = 5.5 Hz) |
| 91 | 3.50- 3.54 (2H, m), 4.07 (2H, 1, J = 5.7 Hz), 5.24 (2H, s), 5.46 (2H, s), 6.93 (1H, dd, J = 8.4, 2.4 Hz), 6.99 (1H, dd, J = 7.9, 2.0 Hz), 7.03 (1H, t, J = 2.2 Hz), 7.13 (1H, dd, J = 5.0, 1.5 Hz), 7.30 (1H, t, J = 8.1 Hz), 7.53 (1H, ddd, J = 8.0, 4.8, 0.9 Hz), 7.92 (1H, s), 8.06 (1H, t, J = 5.6 Hz), 8.09 (1H, s), 8.38 (1H, ddd, J = 8.0, 2.3, 1.7 Hz), 8.64 (1H, dd, J = 4.8, 1.6 Hz), 8.67 (1H, d, J = 5.0 Hz), 9.21 (1H, dd, J = 2.3, 0.9 Hz) |
| 92 | 3.47-3.52 (2H, m), 4.05 (2H, t, J = 5.8 Hz), 5.21 (2H, s), 5.39 (2H, s), 6.91-7.04 (4H, m), 7.28 (1H, d, J = 8.2 Hz), 7.32 (1H, d, J = 8.3 Hz), 7.72 (1H, d, J = 8.3 Hz), 7.96-8.01 (2H, m), 8.04 (1H, s), 13.02 (1H, s) |

TABLE 13-continued

NMR data of examples (solvent d6 DMSO)

Example Number Chemical shift 93 3.47-3.51 (2H, m), 4.02 (3H, s), 4.05 (2H, t, J = 5.7 Hz), 5.20 (2H, s), 5.38 (2H, s), 6.90-6.93 (1H, m), 6.97-7.04 (3H, m), 7.26-7.32 (1H, m), 7.56 (1H, s), 7.72 (1H, d, J = 8.6 Hz), 7.95-7.99 (2H, m), 8.02 (1H, d, J = 0.7 Hz)

94 1.97-2.07 (2H, m), 2.52-2.59 (2H, m), 3.49-3.53 (2H, m), 3.96 (2H, dd, J = 7.5, 6.6 Hz), 4.07 (2H, t, J = 5.8 Hz), 5.15 (2H, s), 5.43 (2H, s), 6.90 (1H, dd, J = 5.1, 1.5 Hz), 6.94 (1H, dd, J = 8.4, 2.5 Hz), 6.99 (1H, dd, J = 7.9, 2.0 Hz), 7.04 (1H, t, J = 2.2 Hz), 7.30 (1H, t, J = 8.1 Hz), 8.01-8.07 (2H, m), 8.15 (1H, s), 8.32 (1H, d, J = 5.1 Hz)

95 2.60 (3H, s), 3.65 (2H, t, J = 5.6 Hz), 3.79 (3H, s), 4.09 (2H, t, J = 5.6 Hz), 5.21 (2H, s), 6.87 (1H, ddd, J = 0.9, 2.5, 8.4 Hz), 6.92 (1H, ddd, J = 0.9, 2.0, 7.9 Hz), 6.96 (1H, t, J = 2.2 Hz), 7.19-7.25 (2H, m), 7.45 (1H, d, J = 8.3 Hz), 7.47-7.50 (1H, m), 7.86 (1H, s), 8.39 (1H, s)

96 1.98-2.08 (2H, m), 2.57 (2H, t, J = 8.1 Hz), 3.47-3.50 (2H, m), 3.94-4.01 (2H, m), 4.05 (2H, t, J = 5.8 Hz), 5.07 (2H, s), 5.40 (2H, s br), 6.93 (1H, ddd, J = 0.9, 2.5, 8.4 Hz), 6.99 (1H, ddd, J = 0.9, 2.0, 7.9 Hz), 7.03 (1H, t, J = 2.2 Hz), 7.30 (1H, t, J = 8.1 Hz), 7.70 (1H, dd, J = 2.4, 8.7 Hz), 7.96 (1H, s), 7.99 (1H, t, J = 5.6 Hz), 8.27 (1H, dd, J = 0.8, 8.6 Hz), 8.32 (1H, d, J = 2.3 Hz)

97 3.49-3.52 (2H, m), 4.06 (2H, t, J = 5.7 Hz), 5.20 (2H, s), 5.44 (2H, s br), 6.93 (1H, ddd, J = 0.9, 2.5, 8.4 Hz), 6.99 (1H, ddd, J = 0.9, 2.0, 7.9 Hz), 7.03 (1H, t, J = 2.2 Hz), 7.30 (1H, t, J = 8.1 Hz), 7.52 (1H, ddd, J = 0.9, 4.8, 8.0 Hz), 7.77 (1H, dd, J = 2.4, 8.2 Hz), 8.02-8.07 (3H, m), 8.41 (1H, dt, J = 1.9, 8.0 Hz), 8.59-8.66 (2H, m), 9.24 (1H, dd, J = 0.9, 2.4 Hz)

98 3.45-3.54 (2H, m), 3.81 (3H, s), 4.06 (2H, t, J = 5.8 Hz), 4.99 (2H, s), 5.04 (2H, s), 5.38 (2H, s), 6.18-6.26 (1H, m), 6.39 (1H, ddd, J = 0.7, 1.4, 9.1 Hz), 6.75 (1H, dd, J = 1.5, 7.7 Hz), 6.87-7.07 (5H, m), 7.30 (1H, t, J = 8.1 Hz), 7.42 (1H, ddd, J = 2.1, 6.6, 8.9 Hz), 7.63 (1H, ddd, J = 0.7, 2.1, 6.8 Hz), 7.95 (1H, s), 7.99 (1H, t, J = 5.5 Hz)

99 3.48-3.52 (2H, m), 4.06 (2H, t, J = 5.8 Hz), 5.08 (2H, s), 5.27 (2H, s), 5.38 (2H, s), 6.69-6.74 (1H, m), 6.77-6.81 (1H, m), 6.93 (1H, ddd, J = 0.9, 2.5, 8.3 Hz), 6.99 (1H, ddd, J = 0.9, 2.0, 7.9 Hz), 7.03 (1H, t, J = 2.2 Hz), 7.20-7.26 (2H, m), 7.30 (1H, t, J = 8.1 Hz), 7.41-7.44 (2H, m), 7.89 (1H, dt, J = 7.9, 8.7 Hz), 7.99 (2H, m)

100 3.47-3.51 (2H, m), 4.05 (2H, t, J = 5.8 Hz), 5.01 (2H, s), 5.04 (2H, s), 5.37 (2H, s), 6.44 (1H, dd, J = 5.4, 10.1 Hz), 6.93 (1H, ddd, J = 0.9, 2.5, 8.4 Hz), 6.99 (1H, ddd, J = 0.9, 2.0, 8.0 Hz), 7.02 (1H, t, J = 2.2 Hz), 7.18-7.31 (5H, m), 7.56 (1H, ddd J = 3.4, 7.2, 10.4 Hz), 7.97 (2H, d, J = 8.3 Hz), 8.03 (1H, dd, J = 3.3, 4.8 Hz)

101 3.47-3.52 (2H, m), 4.05 (2H, t, J = 5.8 Hz), 5.08 (4H, s), 5.39 (2H, s), 6.24 (1H, td, J = 1.4, 6.7 Hz), 6.41 (1H, dd, J = 1.3, 9.1 Hz), 6.93 (1H, ddd, J = 0.9, 2.5, 8.4 Hz), 6.96-7.00 (1H, m), 7.03 (1H, t, J = 2.2 Hz), 7.12 (2H, td, J = 1.6, 9.7, 10.4 Hz), 7.27 (2H, dt, J = 7.9, 22.0 Hz), 7.43 (1H, ddd, J = 2.1, 6.6, 8.9 Hz), 7.79 (1H, dd, J = 2.1, 6.8 Hz), 7.98 (1H, s), 8.01 (1H, t, J = 5.6 Hz)

102 3.47-3.52 (2H, m), 4.07 (2H, t, J = 5.8 Hz), 5.09 (2H, s), 5.13 (2H, s), 5.38 (2H, s), 6.23-6.26 (1H, m), 6.40 (1H, d, J = 8.9 Hz), 6.91-7.04 (3H, m), 7.13 (1H, d, J = 8.0 Hz), 7.28-7.32 (1H, m), 7.40-7.44 (1H, m), 7.69 (1H, dd, J = 8.0, 2.2 Hz), 7.85 (1H, dd, J = 6.8, 2.0 Hz), 8.03 (1H, t, J = 5.6 Hz), 8.05 (1H, s), 8.51 (1H, d, J = 2.0 Hz)

28 1.91-1.94 (4H, m), 3.34-3.38 (4H, m), 3.50-3.54 (2H, m), 4.07 (2H, t, J = 5.5 Hz), 5.26 (2H, s), 6.45 (1H, d, J = 8.6 Hz), 6.92 (1H, dd, J = 2.4, 8.5 Hz), 7.02 (2H, q, J = 4.9 Hz), 7.26-7.32 (1H, m), 7.49(1H, dd, J = 2.4, 8.8 Hz), 8.14 (1H, d, J = 2.2 Hz), 8.32 (1H, s), 8.50 (1H, t, J = 5.5 Hz)

103 2.21 (3H, s), 2.29 (3H, s), 3.52-3.54 (2H, m), 4.09 (2H, t, J = 5.8 Hz), 5.06 (2H, s), 5.19 (2H, s), 6.23 (1H, td, J = 1.4, 6.7 Hz), 6.36 - 6,43 (1H, m), 6.91- 6.96 (1H, m), 6.97-7.02 (1H, m), 7.03 (1H, t, J = 2.2 Hz), 7.08-7.13 (2H, m), 7.21 - 7.26 (2H, m), 7.30 (1H, t, J = 8.1 Hz), 7.41 (1H, ddd, J = 2.1, 6.6, 9.0 Hz), 7.66 (1H, t, J = 5.7 Hz), 7.75-7.80 (1H, m)

104 2.10 (3H, s), 3.22 (3H, s), 3.50-3.54 (2H, m), 4.08 (2H, t, J = 5.5 Hz), 4.51 (2H, s), 5.02 (2H, s), 5.27 (2H, s), 6.06-6.09 (1H, m), 6.20 (1H, s), 6.93 (1H, dd, J = 8.7, 2.5 Hz), 6.98-7.03 (2H, m), 7.20-7.32 (5H, m), 7.62 (1H, d, J = 7.0 Hz), 8.10 (1H, t, J = 5.2 Hz), 8.21 (1H, s)

105 1.90-1.99 (1H, m), 2.13-2.25 (1H, m), 3.10 (1H, dd, J = 9.9, 4.7 Hz), 3.22-3.31 (1H, m), 3.34-3.41 (1H, m), 3.51 (1H, dd, J = 9.9, 6.7 Hz), 4.45-4.55 (1H, m), 5.02 (2H, s), 5.06 (2H, s), 5.38 (2H, s), 6.22 (1H, dt, J = 6.7, 1.4 Hz), 6.39 (1H, d, J = 9.0Hz), 6.48 (1H, dd, J = 8.4, 1.8 Hz), 6.51 (1H, t, J = 2.0 Hz), 6.60 (1H, d, J = 7.6, 1.6 Hz), 7.15 (1H, dd, J = 8.1, 8.0), 7.19 (2H, d, J = 8.2 Hz), 7.26 (2H, d, J = 8.1 Hz), 7.40 (1H, ddd, J = 8.9, 6.6, 2.1 Hz), 7.75 (1H, dd, J = 6.8, 2.0 Hz), 7.87 (1H, br d, J = 6.7 Hz), 7.99 (1H, s)

106 1.90-1.99 (1H, m), 2.13-2.25 (1H, m), 3.10 (1H, dd, J = 10.0, 4.5 Hz), 3.22-3.30 (1H, m), 3.32-3.41 (1H, m), 3.51 (1H, dd, J = 9.9, 6.7 Hz), 4.47-4.53 (1H, m), 5.02 (2H, s), 5.06 (2H, s), 5.38 (2H, s), 6.22 (1H, dt, J = 6.7, 1.4 Hz), 6.39 (1H, d, J = 8.8 Hz), 6.48 (1H, dd, J = 8.4, 2.0 Hz), 6.51 (1H, t, J = 2.1 Hz), 6.60 (1H, d, J = 7.8, 1.6 Hz), 7.15 (1H, dd, J = 8.1, 8.0), 7.19 (2H, d, J = 8.2 Hz), 7.26 (2H, d, J = 8.1 Hz), 7.41 (1H, ddd, J = 8.9, 6.5, 2.0 Hz), 7.75 (1H, dd, J = 6.6, 1.9 Hz), 7.89 (1H, br d, J = 6.4 Hz), 8.00 (1H, s)

107 1.98-2.09 (1H, m), 2.32-2.42 (1H, m), 3.80-3.83 (2H, m), 4.65-4.72 (1H, m), 5.06 (2H, s), 5.07 (2H, s), 5.37 (2H, s), 6.22-6.24 (1H, m), 6.40 (1H, d, J = 9.1 Hz), 7.21 (3H, d, J =8.2 Hz), 7.27 (2H, d, J = 8.1 Hz), 7.40-7.44 (2H, m), 7.59-7.61 (1H, m), 7.76 (1H, q, J = 1.8 Hz), 7.88 (1H, t, J = 2.0 Hz), 7.95 (1H, s), 8.21 (1H, t, J = 8.3 Hz)

108 1.61-1.69 (1H, m), 2.05-2.14 (1H, m), 2.31-2.35 (1H, m), 2.41-2.46 (1H, m), 2.56-2.61 (1H, m), 2.66-2.73 (1H, m), 3.57 (2H, s), 4.23-4.31 (1H, m), 5.02 (2H, s), 5.07 (2H, s),

TABLE 13-continued

NMR data of examples (solvent d6 DMSO)

| Example Number | Chemical shift |
|---|---|
| | 5.32 (2H, s), 6.20-6.24 (1H, m), 6.40 (1H, d, J = 8.8 Hz), 7.19 (2H, d, J = 8.2 Hz), 7.26 (2H, d, J = 8.1 Hz), 7.28-7.36 (4H, m), 7.38-7.43 (1H, m), 7.73-7.76 (2H, m), 8.00 (1H, s) |
| 109 | 1.61-1.70 (1H, m), 2.05-2.14 (1H, m), 2.32-2.35 (1H, m), 2.41-2.46 (1H, m), 2.56-2.62 (1H, m), 2.66-2.73 (1H, m), 3.57 (2H, s), 4.23-4.30 (1H, m), 5.02 (2H, s), 5.07 (2H, s), 5.32 (2H, s), 6.20-6.24 (1H, m), 6.40 (1H, d, J = 8.8 Hz), 7.19 (2H, d, J = 8.2 Hz), 7.27 (2H, d, J = 8.0 Hz), 7.29-7.36 (4H, m), 7.38-7.44 (1H, m), 7.75-7.76 (2H, m), 8.00 (1H, s) |
| 110 | 1.98-2.09 (1H, m), 2.32-2.40 (1H, m), 3.71-3.85 (2H, m), 4.67-4.72 (1H, m), 5.06 (2H, s), 5.07 (2H, s), 5.37 (2H, s), 6.21-6.24 (1H, m), 6.40 (1H, d, J = 9.1 Hz), 7.21 (3H, d, J = 8.1 Hz), 7.27 (2H, d, J = 8.1 Hz), 7.40-7.44 (2H, m), 7.60 (1H, q, J = 1.6 Hz), 7.76 (1H, q, J = 1.9 Hz), 7.88 (1H, t, J = 2.0 Hz), 7.95 (1H, s), 8.21 (1H, t, J = 8.2 Hz) |
| 111 | 2.46-2.47 (1H, m), 2.92-2.98 (1H, m), 3.66-3.69 (1H, m), 4.13-4.18 (1H, m), 4.51-4.55 (1H, m), 5.03 (2H, s), 5.06 (2H, s), 5.37 (2H, s), 6.20-6.23 (1H, m), 6.39 (1H, d, J = 9.6 Hz), 7.17-7.20 (3H, m), 7.25 (2H, d, J = 8.2 Hz), 7.39-7.41 (2H, m), 7.52-7.55 (1H, m), 7.75 (1H, dd, J = 1.9, 6.8 Hz), 7.89 (1H, t, J = 2.1 Hz), 7.95 (1H, s), 8.16 (1H, d, J = 6.5 Hz) |
| 112 | 1.91-1.95 (1H, m), 2.15-2.33 (1H, m), 3.40-3.44 (4H, m), 3.60-3.70 (1H, m), 4.10-4.20 (1H, m), 5.06 (4H, s), 5.37 (2H, s), 6.19 (1H, q, J = 6.7 Hz), 6.38 (1H, d, J = 9.0 Hz), 6.57-6.61, 2H, m), 7.18-7.27 (4H, m), 7.38-7.42 (1H, m), 7.74 (1H, dd, J = 1.8, 6.8 Hz), 7.86 (1H, d, J = 5.8 Hz), 8.16 (1H, s) |
| 113 | 1.18 (3H, d, J = 6.8 Hz), 3.83-3.87 (1H, m), 3.99-4.03 (1H, m), 4.20-4.27 (1H, m), 5.03 (2H, s), 5.07 (2H, s), 5.36 (2H, s), 6.20-6.24 (1H, m), 6.39 (1H, d, J = 9.0 Hz), 6.92-6.99 (2H, m), 7.03-7.04 (1H, m), 7.20 (2H, d, J = 8.1 Hz), 7.24-7.31 (3H, m), 7.39-7.43 (1H, m), 7.69 (1H, d, J = 7.8 Hz), 7.75 (1H, dd, J = 6.8, 2.0 Hz), 7.98 (1H, s) |
| 114 | 1.18 (3H, d, J = 6.8 Hz), 3.83-3.87 (1H, m), 3.99-4.03 (1H, m), 4.20-4.27 (1H, m), 5.03 (2H, s), 5.07 (2H, s), 5.36 (2H, s), 6.20-6.24 (1H, m), 6.40 (1H, d, J = 9.3 Hz), 6.92-6.99 (2H, m), 7.03-7.04 (1H, m), 7.20 (2H, d, J = 8.2 Hz), 7.26-7.31 (3H, m), 7.39-7.43 (1H, m), 7.69 (1H, d, J = 7.6 Hz), 7.75 (1H, dd, J = 6.7, 1.9 Hz), 7.98 (1H, m) |
| 115 | 1.23 (3H, d, J = 6.1 Hz), 3.20-3.26 (1H, m), 3.40-3.46 (1H, m) 4.49-4.56 (1H, m), 5.03 (2H, s), 5.07 (2H, s), 5.35 (2H, s), 6.20-6.24 (1H, m), 6.40 (1H, d, J = 8.9 Hz), 6.94-6.97 (2H, m), 7.06 (1H, t, J = 2.2 Hz), 7.19 (2H, d, J = 8.1 Hz), 7.26 (2H, d, J = 9.3 Hz), 7.29 (1H, s), 7.38-7.43 (1H, m), 7.75 (1H, dd, J = 6.9, 1.9 Hz), 7.95 (2H, s) |
| 116 | 1.11 (3H, s br), 3.17 (3H, s br), 4.37 (1H, s br), 5.03 (2H, s), 5.07 (2H, s), 5.31 (2H, s), 6.20-6.24 (1H, m), 6.39 (1H, d, J = 8.9 Hz), 7.20 (2H, d, J = 8.1 Hz), 7.27 (2H, d, J = 8.2 Hz), 7.38-7.48 (4H, m), 7.58 (1H, s br), 7.75 (1H, dd, J = 1.8, 6.7Hz), 7.89 (1H, s br), 8.06 (1H, s) |
| 117 | 1.11 (3H, s br), 3.17 (3H, s br), 4.38 (1H, s br), 5.03 (2H, s), 5.07 (2H, s), 5.31 (2H, s), 6.20-6.25 (1H, m), 6.39 (1H, d, J = 9.1 Hz), 7.20 (2H, d, J = 8.1 Hz), 7.27 (2H, d, J = 8.1 Hz), 7.38-7.48 (4H, m), 7.58 (1H, s br), 7.75 (1H, dd, J = 1.8, 6.8 Hz), 7.89 (1H, s br), 8.06 (1H, s) |
| 118 | 1.23 (3H, d, J = 6.1 Hz), 3.19-3.25 (1H, m), 3.40-3.46 (1H, m) 4.49-4.56 (1H, m), 5.03 (2H, s), 5.07 (2H, s), 5.38 (2H, s), 6.21-6.25 (1H, m), 6.40 (1H, d, J = 9.1 Hz), 6.96 (2H, d, J = 8.4 Hz), 7.06-7.07 (1H, m), 7.18 (2H, d, J = 8.0 Hz), 7.25-7.30(3H, m), 7.39-7.43 (1H, m), 7.77 (1H, d, J = 6.5 Hz), 7.96 (1H, s), 8.00 (1H, d, J = 5.2 Hz) |
| 119 | (MeOD) 1.33 (3H, d, J = 6.2 Hz), 3.51 (2H, d, J = 5.2 Hz), 4.64 (1H, q, J = 6.0 Hz), 5.11(2H, s), 5.18 (2H, s), 6.61 (1H, dd, J = 10.0, 5.3 Hz), 6.91-6.94 (2H, m), 7.02 (1H, t, J =2.2 Hz), 7.23 (1H, d, J = 8.2 Hz), 7.27 (1H, d, J = 8.0 Hz), 7.37 (2H, d, J = 8.2 Hz), 7.56-7.61 (1H, m), 7.82 (1H, t, J = 3.8 Hz), 7.85 (1H, s) |

Biological Methods

The ability of the compounds of formula (I) to inhibit plasma kallikrein may be determined using the following biological assays:

Determination of the $IC_{50}$ for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 25° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data acquired from these assays are shown in Table 14

Selected compounds were further screened for inhibitory activity against the related enzyme KLK1. The ability of the compounds of formula (I) to inhibit KLK1 may be determined using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human KLK1 (Callbiochem) was incubated at 25° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

Data acquired from this assay are shown in Table 14

Selected compounds were further screened for inhibitory activity against the related enzyme FXIa. The ability of the compounds of formula (I) to inhibit FXIa may be determined using the following biological assay:

Determination of the % Inhibition for FXIa

FXIa inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human FXIa (Enzyme Research Laboratories) was incubated at 25° C. with the fluorogenic substrate Z-Gly-Pro-Arg-AFC and 40 µM of the test compound. Residual enzyme activity (initial rate of reaction) was determined by measuring the change in optical absorbance at 410 nm.

Data acquired from this assay are shown in Table 14

TABLE 14

| Example Number | $IC_{50}$ (human PKal) nM | IC50 (human KLK1) nM | % Inhibition @ 40 µM (human FXIa) |
|---|---|---|---|
| 1 | 2.9 | >10000 | 2 |
| 2 | 60.2 | >10000 | 0 |
| 115 | 5.6 | >40000 | |
| 37 | 18.5 | >40000 | 8 |
| 3 | 5530 | >10000 | 0 |
| 4 | >10000 | >10000 | |
| 5 | 68.4 | >10000 | 0 |
| 6 | 1890 | >10000 | 0 |
| 8 | 16.6 | >10000 | 0 |
| 9 | 191 | >10000 | 0 |
| 10 | 134 | >10000 | 0 |
| 11 | >10000 | >10000 | |
| 12 | 266 | >10000 | 0 |
| 14 | 161 | >40000 | 0 |
| 15 | 24.6 | >40000 | 1 |
| 29 | 2930 | >40000 | 0 |
| 30 | 96.8 | >40000 | 0 |
| 31 | 646 | >40000 | 47 |
| 32 | 10.1 | >40000 | 10 |
| 33 | 114 | >40000 | 29 |
| 34 | 92.8 | >40000 | 7 |
| 35 | 122 | >40000 | 1 |
| 36 | 6.1 | >40000 | 0 |
| 38 | 6.5 | >40000 | |
| 39 | 16.3 | >40000 | |
| 40 | 12.6 | >40000 | 0 |
| 41 | 264 | >40000 | 0 |
| 42 | 3.2 | >40000 | 0 |
| 43 | 77 | >10000 | |
| 17 | 96.0 | >10000 | 2 |
| 44 | >10000 | >40000 | |
| 45 | 6250 | >40000 | |
| 18 | 2010 | >40000 | 0 |
| 21 | 2790 | >40000 | 56 |
| 46 | >10000 | >10000 | |
| 47 | 30.1 | >40000 | 32 |
| 27 | 231 | >10000 | 0 |
| 48 | 6620 | >10000 | 3 |
| 49 | 847 | >40000 | 0 |
| 50 | 326 | >40000 | 59 |
| 51 | 427 | >40000 | 51 |
| 52 | 335 | >40000 | 0 |
| 53 | 4730 | >40000 | 0 |
| 54 | 245 | >40000 | 67 |
| 55 | 6410 | >40000 | 80 |
| 56 | 8490 | >40000 | 0 |
| 57 | 6830 | >40000 | 0 |
| 58 | 5420 | >40000 | 1 |
| 59 | >10000 | >40000 | |
| 60 | >10000 | >40000 | |
| 61 | 7250 | >40000 | 0 |
| 62 | 7150 | >40000 | 4 |
| 63 | >10000 | >40000 | |
| 64 | >10000 | >40000 | |
| 65 | >10000 | >40000 | |
| 66 | 4920 | >40000 | 0 |
| 67 | >10000 | >40000 | |
| 68 | >10000 | >40000 | 0 |
| 69 | >10000 | >40000 | 0 |
| 70 | >10000 | >40000 | 6 |
| 71 | 2070 | >40000 | 0 |

TABLE 14-continued

| Example Number | $IC_{50}$ (human PKal) nM | IC50 (human KLK1) nM | % Inhibition @ 40 µM (human FXIa) |
|---|---|---|---|
| 72 | 5940 | >40000 | 26 |
| 73 | >10000 | >40000 | 0 |
| 74 | >10000 | >40000 | 4 |
| 75 | 3670 | >40000 | 0 |
| 76 | 227 | >40000 | 0 |
| 77 | 112 | >40000 | 0 |
| 78 | 6930 | >40000 | 4 |
| 79 | 5870 | >40000 | 9 |
| 80 | 6330 | >40000 | 0 |
| 81 | >10000 | >40000 | |
| 82 | 710 | >40000 | 0 |
| 83 | 298 | >40000 | 0 |
| 84 | 731 | >40000 | 3 |
| 85 | 3.5 | >40000 | 1 |
| 86 | 30.2 | >40000 | 0 |
| 87 | 780 | >40000 | 0 |
| 88 | 9180 | >40000 | 0 |
| 89 | 3350 | >40000 | 33 |
| 90 | >10000 | >40000 | 0 |
| 91 | 3780 | >40000 | 0 |
| 92 | >10000 | >10000 | 2 |
| 93 | >10000 | >40000 | 2 |
| 94 | 3140 | >40000 | |
| 95 | 1900 | >40000 | |
| 96 | 2230 | >40000 | |
| 97 | 1130 | >40000 | |
| 98 | 9.4 | >40000 | |
| 99 | 2070 | >40000 | |
| 100 | 6.2 | >40000 | |
| 101 | 7.6 | >40000 | |
| 102 | 72.1 | >40000 | |
| 28 | 2390 | >10000 | 0 |
| 103 | >10000 | >40000 | |
| 104 | 413 | >40000 | |
| 105 | 3.8 | >40000 | 0 |
| 106 | 684 | >40000 | 4 |
| 107 | 4.8 | >40000 | 2 |
| 108 | 299 | >40000 | 0 |
| 109 | 384 | >40000 | 0 |
| 110 | 4.0 | >40000 | 13 |
| 111 | 42.1 | >40000 | 23 |
| 112 | 7460 | >40000 | 29 |
| 113 | 316 | >40000 | 3 |
| 114 | 140 | >40000 | 0 |
| 116 | 390 | >40000 | 0 |
| 117 | 3020 | >40000 | 4 |
| 118 | 13.3 | >40000 | |

Pharmacokinetics

Pharmacokinetic studies of the compounds in Table 15 were performed to assess the pharmacokinetics following a single oral dose in male Sprague-Dawley rats. Two rats were given a single po dose of 5 mL/kg of a nominal 2 mg/mL (10 mg/kg) composition of test compound in 10% DMSO/10% cremophor/80% SWFI. Following dosing, blood samples were collected over a period of 24 hours. Sample times were 5, 15 and 30 minutes then 1, 2, 4, 6, 8 and 12 hours. Following collection, blood samples were centrifuged and the plasma fraction analysed for concentration of test compound by LCMS. Oral exposure data acquired from these studies are shown below:

TABLE 15

Oral exposure data

| Example Number | Dose po (mg/kg) | Cmax (ng/mL) | Tmax (min) |
|---|---|---|---|
| 115 | 7.6 | 538 | 30 |
| 85 | 8.4 | 228 | 45 |

The invention claimed is:
1. A compound of formula (I),

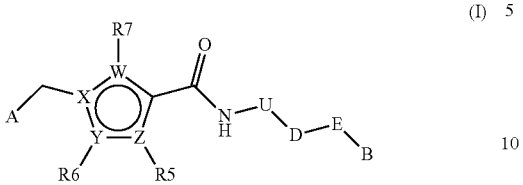

wherein:
- B is $(CH_2)_n$phenyl, wherein n is 0 or 1 and phenyl is substituted with 1 to 3 alkyl, alkoxy, OH, halo, CN, COOalkyl, CONR8R9, $OCF_3$, $CF_3$, or NR8R9 substituents;
- or B is a 5 or 6 membered heterocyclic ring containing one or two N, O, or S atoms; said heterocyclic ring is aromatic or non-aromatic and is substituted with 1 to 3 alkyl, alkoxy, OH, oxo, halo, CN, COORS, CONR8R9, $OCF_3$, $CF_3$, or NR8R9 substituents;
- D is $CH_2$, CHalkyl$^b$, C(alkyl$^b$)$_2$, or CO; and
either:
- U is $CH_2$, CHalkyl$^b$, or C(alkyl$^b$)$_2$; and E is NH, Nalkyl$^b$, $CH_2$, or O; or
- U is CH; and E is N; and U, D and E together form part of an azacarbocycle;
- W and X are independently C or N, and Y and Z are independently C, N, O, or S, such that the ring containing W, X, Y and Z is a five-membered aromatic heterocycle that is thiene, furan, pyrrole, pyrazole, or imidazole;
  - wherein when the ring containing W, X, Y and Z is pyrazole, either (i) W is C, X is N, Y is N, and Z is C or (ii) W is C, X is C, Y is N and Z is N;
- R5 and R6 are, independently, absent, H, alkyl, $-NH_2$, CN, $CF_3$, or R16; provided at least one of R5 and R6 is present and is not H;
- R7 is H;
- A is aryl or heteroaryl;
- R8 and R9 are, independently, H or alkyl;
- R16 is a monocyclic saturated hydrocarbon of between 3 and 7 carbon atoms, wherein R16 is optionally substituted with alkyl substituents;
- alkyl is a linear saturated hydrocarbon having up to 10 carbon atoms ($C_1$-$C_{10}$) or a branched saturated hydrocarbon of between 3 and 10 carbon atoms ($C_3$-$C_{10}$); alkyl is optionally substituted with 1 or 2 independent ($C_1$-$C_6$)alkoxy, OH, CN, $CF_3$, COOR10, CONR10R11, fluoro, or NR10R11 substituents;
- alkyl$^b$ is a linear saturated hydrocarbon having up to 6 carbon atoms ($C_1$-$C_6$) or a branched saturated hydrocarbon of between 3 and 6 carbon atoms ($C_3$-$C_6$); alkyl$^b$ is optionally substituted with 1 or 2 independent methoxy, ethoxy, n-propoxy, n-butoxy, isopropoxy, sec-butoxy, tert-butoxy, OH, CN, $CF_3$, or fluoro substituents;
- alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy is optionally substituted with 1 or 2 independent OH, CN, $CF_3$, $-$COOR14, $-$CONR14R15, fluoro, or NR14R15 substituents;
- azacarbocycle is a 5- or 6-membered mono-cyclic carbon-containing ring, which comprises one or two nitrogen atoms in the ring, and which is optionally substituted by oxo;
- aryl is substituted phenyl, optionally substituted biphenyl or optionally substituted naphthyl; wherein the substituents are 1, 2 or 3 independent alkyl, alkoxy, methylenedioxy, ethylenedioxy, OH, $OCF_3$, halo, CN, heteroaryl, $-(CH_2)_{0-3}$-O-heteroaryl, aryl$^b$, $-$O-aryl$^b$, $-(CH_2)_{1-3}$-aryl$^b$, $-(CH_2)_{1-3}$-heteroaryl, $-$COOR10, $-$CONR10R11, $-(CH_2)_{0-3}-$NR10R11, or $CF_3$ substituents;
- aryl$^b$ is phenyl, biphenyl or naphthyl, optionally substituted with 1, 2 or 3 independent alkyl$^b$, alkoxy, OH, halo, CN, $-$COOR14, $-$CONR14R15, fluoro, or NR14R15 substituents;
- heteroaryl is a 5, 6, 9 or 10 membered mono- or bi-cyclic aromatic ring, containing, where possible, 1, 2 or 3 independent N, NR8, S, or O ring members; heteroaryl is optionally substituted with 1, 2 or 3 independent alkyl, alkoxy, OH, $OCF_3$, halo, CN, aryl$^b$, $-(CH_2)_{1-3}$-aryl$^b$, heteroaryl$^b$, $-$COOR10, $-$CONR10R11, $CF_3$, or $-(CH_2)_{0-3}-$NR10R11 substituents;
- heteroaryl$^b$ is a 5, 6, 9 or 10 membered mono- or bi-cyclic aromatic ring, containing, where possible, 1, 2 or 3 independent N, S, or O ring members; wherein heteroaryl$^b$ is optionally substituted with 1, 2 or 3 independent alkyl$^b$, alkoxy, OH, halo, CN, aryl$^b$, $-(CH_2)_{1-3}$-aryl$^b$, $-$COOR14, $-$CONR14R15, $CF_3$, or NR14R15 substituents;
- R10 and R11 are independent H, alkyl$^b$, CONR14R15, COR17, aryl$^b$, or heteroaryl$^b$ substituents; or R10 and R11 together with the nitrogen atom to which they are attached form a carbon-containing 4-, 5-, 6- or 7-membered heterocyclic ring, optionally containing an additional N, S, or O atom, which is saturated or unsaturated with 1 or 2 double bonds and optionally mono- or di-substituted with independent oxo, alkyl$^b$, alkoxy, OH, halo, or $CF_3$ substituents;
- R14, R15 and R17 are independently H or alkyl$^b$;

or a tautomer, stereoisomer, pharmaceutically acceptable salt, or solvate thereof.

2. A compound according to claim 1, wherein:
- B is phenyl substituted with 1 to 3 independent alkyl, alkoxy, OH, halo, CN, $-$COOalkyl, CONR8R9, $OCF_3$, $CF_3$, or NR8R9 substituents;
- or B is 5 or 6 membered heterocyclic ring containing one or two N, O and S atoms; said heterocyclic ring is aromatic or non-aromatic and substituted with 1 to 3 alkyl, alkoxy, OH, oxo, halo, CN, COORS, CONR8R9, $OCF_3$, $CF_3$, or NR8R9 substituents;
- D is $CH_2$ or CO;
- U is $CH_2$;
- E is NH, $CH_2$, or O;
- R10 and R11 are, independently, H, alkyl$^b$, aryl$^b$, or heteroaryl$^b$; or R10 and R11 together with the nitrogen atom to which they are attached form a carbon-containing 4-, 5-, 6- or 7-membered heterocyclic ring, optionally containing an additional N, S and O atom, which is saturated or unsaturated with 1 or 2 double bonds and which is optionally mono- or di-substituted with oxo, alkyl$^b$, alkoxy, OH, halo, or $CF_3$ substituents.

3. A compound according to claim 1, wherein:
B is (CH$_2$)$_n$phenyl, wherein n is 0 or 1 and phenyl is substituted with 1 to 3 alkyl, alkoxy, halo, CN, —COOalkyl, CONR8R9, OCF$_3$, CF$_3$, or NR8R9 substituents;
or B is 5 or 6 membered heterocyclic ring containing one or two N, O, or S atoms; said heterocyclic ring is aromatic or non-aromatic and substituted with 1 to 3 alkyl, alkoxy, OH, oxo, halo, CN, COORS, CONR8R9, OCF$_3$, CF$_3$, or NR8R9 substituents.

4. A compound according to claim 1, wherein B is phenyl or pyridyl, each substituted with 1 to 3 alkyl, alkoxy or halo substituents.

5. A compound according to claim 1, wherein at least one of said 1 to 3 substituents on B is Cl.

6. A compound according to claim 1, wherein B is

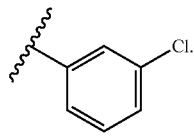 [SMILES: *c1cccc(Cl)c1]

7. A compound according to claim 1, wherein D is CH$_2$ or CHMe, and E is O.

8. A compound according to claim 1, wherein the ring containing W, X, Y, and Z is a pyrrole, pyrazole, or imidazole substituted by at least one alkyl, —NH$_2$, CN, CF$_3$, or R16.

9. A compound according to claim 1, wherein R7 is H, R6 is absent and R5 is methyl, CH$_2$OCH$_3$, R16, NH$_2$, or CF$_3$; wherein R16 is cyclopropyl.

10. A compound according to claim 1, wherein R7 is H, R6 is absent and R5 is NH$_2$.

11. A compound according to claim 1, wherein A is phenyl substituted with —(CH$_2$)$_{1-3}$-heteroaryl or —(CH$_2$)$_{1-3}$—NR10R11 and, optionally, 1 or 2 additional alkyl, alkoxy, halo, or CF$_3$ independent substituents.

12. A compound according to claim 1, wherein A is pyridyl substituted with heteroaryl$^b$ or —NR10R11 and, optionally, 1 or 2 additional alkyl, halo, or CF$_3$ independent substituents.

13. A compound according to claim 1, wherein —NR10R11 is

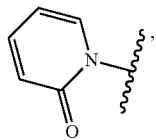 [SMILES: *n1ccccc1=O]

optionally mono-substituted with alkyl$^b$, alkoxy, OH, halo, or CF$_3$.

14. A compound according to claim 1, that is:
3-amino-1-[4-(2-oxo-2H-pyridin-1-ylmethyl)-benzyl]-1H-pyrazole-4-carboxylic acid [2-(3-chloro-phenoxy)-ethyl]-amide;
3-amino-1-[4-(2-oxo-2H-pyridin-1-ylmethyl)-benzyl]-1H-pyrazole-4-carboxylic acid [(3-chloro-phenylcarbamoyl)-methyl]-amide];
2-{[3-amino-1-({4-[(2-oxopyridin-1-yl)methyl]phenyl}methyl)pyrazol-4-yl]formamido}-N-(2-chlorophenyl)acetamide;
2-{[3-amino-1-({4-[(2-oxopyridin-1-yl)methyl]phenyl}methyl)pyrazol-4-yl]formamido}-N-(4-chlorophenyl)acetamide;
N-[2-(3-chlorophenoxy)ethyl]-3-cyclopropyl-1-({4-[(2-oxopyridin-1-yl)methyl]phenyl}methyl)pyrazole-4-carboxamide;
N-[2-(2-chlorophenoxy)ethyl]-3-(methoxymethyl)-1-({4-[(2-oxopyridin-1-yl)methyl]phenyl}methyl)pyrazole-4-carboxamide;
N-[2-(3-chlorophenoxy)ethyl]-1-({4-[(2-oxopyridin-1-yl)methyl]phenyl}methyl)-3-(trifluoromethyl)pyrazole-4-carboxamide;
N-[2-(3-chlorophenoxy)ethyl]-3-(methoxymethyl)-1-({4-[(2-oxopyridin-1-yl)methyl]phenyl}methyl)pyrazole-4-carboxamide;
N-[2-(5-chloro-2-fluorophenoxy)ethyl]-3-(methoxymethyl)-1-({4-[(2-oxopyridin-1-yl)methyl]phenyl}methyl)pyrazole-4-carboxamide;
N-[2-(3-chloro-5-fluorophenoxy)ethyl]-3-(methoxymethyl)-1-({4-[(2-oxopyridin-1-yl)methyl]phenyl}methyl)pyrazole-4-carboxamide;
N-[2-(3-chloro-5-methoxyphenoxy)ethyl]-3-(methoxymethyl)-1-({4-[(2-oxopyridin-1-yl)methyl]phenyl}methyl)pyrazole-4-carboxamide;
N-[2-(3-chloro-4-fluorophenoxy)ethyl]-3-(methoxymethyl)-1-({4-[(2-oxopyridin-1-yl)methyl]phenyl}methyl)pyrazole-4-carboxamide;
3-amino-N-[2-(5-chloro-2-methylphenoxy)ethyl]-1-({4-[(2-oxopyridin-1-yl)methyl]phenyl}methyl)pyrazole-4-carboxamide;
3-amino-N-[2-(3-chloro-4-methylphenoxy)ethyl]-1-({4-[(2-oxopyridin-1-yl)methyl]phenyl}methyl)pyrazole-4-carboxamide;
3-amino-N-[2-(2,3-dichlorophenoxy)ethyl]-1-({4-[(2-oxopyridin-1-yl)methyl]phenyl}methyl)pyrazole-4-carboxamide;
3-amino-N-[2-(3,4-dichlorophenoxy)ethyl]-1-({4-[(2-oxopyridin-1-yl)methyl]phenyl}methyl)pyrazole-4-carboxamide;
3-amino-N-[2-(3,5-dichlorophenoxy)ethyl]-1-({4-[(2-oxopyridin-1-yl)methyl]phenyl}methyl)pyrazole-4-carboxamide;
3-amino-N-[2-(5-chloro-2-cyanophenoxy)ethyl]-1-({4-[(2-oxopyridin-1-yl)methyl]phenyl}methyl)pyrazole-4-carboxamide;
3-amino-N-[2-(3-chloro-5-methylphenoxy)ethyl]-1-({4-[(2-oxopyridin-1-yl)methyl]phenyl}methyl)pyrazole-4-carboxamide;
3-amino-N-[2-(2,5-dichlorophenoxy)ethyl]-1-({4-[(2-oxopyridin-1-yl)methyl]phenyl}methyl)pyrazole-4-carboxamide;
N-[2-(3-chlorophenoxy)ethyl]-3-cyano-1-({4-[(2-oxopyridin-1-yl)methyl]phenyl}methyl)pyrazole-4-carboxamide;
N-[2-(3-chlorophenoxy)ethyl]-3-methyl-1-({4-[(2-oxopyridin-1-yl)methyl]phenyl}methyl)pyrazole-4-carboxamide;
2-{[3-amino-1-({4-[(2-oxopyridin-1-yl)methyl]phenyl}methyl)pyrazol-4-yl]formamido}-N-(3-chlorophenyl)-N-methylacetamide;
3-amino-N-{2-[(3-chlorophenyl)(methyl)amino]ethyl}-1-({4-[(2-oxopyridin-1-yl)methyl]phenyl}methyl)pyrazole-4-carboxamide;
3-amino-N-[3-(3-chlorophenyl)propyl]-1-({4-[(2-oxopyridin-1-yl)methyl]phenyl}methyl)pyrazole-4-carboxamide;

N-{2-[(5-chloropyridin-3-yl)oxy]ethyl}-2-methyl-1-({4-[(2-oxopyridin-1-yl)methyl]phenyl}methyl)imidazole-4-carboxamide;

N-[2-(3-chlorophenoxy)ethyl]-2-methyl-1-({4-[(2-oxopyridin-1-yl)methyl]phenyl}methyl)imidazole-4-carboxamide;

3-amino-N-{2-[(5-chloropyridin-3-yl)oxy]ethyl}-1-({4-[(2-oxopyridin-1-yl)methyl]phenyl}methyl)pyrazole-4-carboxamide;

N-[3-(5-chloro-2-oxopyrimidin-1-yl)propyl]-3-(methoxymethyl)-1-({4-[(2-oxopyridin-1-yl)methyl]phenyl}methyl)pyrazole-4-carboxamide;

N-[3-(5-chloro-1,3-thiazol-2-yl)propyl]-3-(methoxymethyl)-1-({4-[(2-oxopyridin-1-yl)methyl]phenyl}methyl)pyrazole-4-carboxamide;

3-amino-N-[3-(4-chloropyrazol-1-yl)propyl]-1-({4-[(2-oxopyridin-1-yl)methyl]phenyl}methyl)pyrazole-4-carboxamide;

3-amino-N-{2-[(4-chloro-1H-pyrazol-3-yl)oxy]ethyl}-1-({4-[(2-oxopyridin-1-yl)methyl]phenyl}methyl)pyrazole-4-carboxamide;

N-{2-[(5-chloro-1,3-thiazol-2-yl)oxy]ethyl}-3-(methoxymethyl)-1-({4-[(2-oxopyridin-1-yl)methyl]phenyl}methyl)pyrazole-4-carboxamide;

N-[3-(5-chloro-1,2-oxazol-3-yl)propyl]-3-(methoxymethyl)-1-({4-[(2-oxopyridin-1-yl)methyl]phenyl}methyl)pyrazole-4-carboxamide;

N-{2-[(4-chlorothiophen-2-yl)sulfanyl]ethyl}-3-(methoxymethyl)-1-({4-[(2-oxopyridin-1-yl)methyl]phenyl}methyl)pyrazole-4-carboxamide;

N-{2-[(4-chlorofuran-2-yl)sulfanyl]ethyl}-3-(methoxymethyl)-1-({4-[(2-oxopyridin-1-yl)methyl]phenyl}methyl)pyrazole-4-carboxamide;

N-{2-[(5-chloropyridazin-3-yl)oxy]ethyl}-3-(methoxymethyl)-1-({4-[(2-oxopyridin-1-yl)methyl]phenyl}methyl)pyrazole-4-carboxamide;

3-amino-N-{2-[(4-chloropyridin-2-yl)amino]ethyl}-1-({4-[(2-oxopyridin-1-yl)methyl]phenyl}methyl)pyrazole-4-carboxamide;

N-[2-(3-chlorophenoxy)ethyl]-3-(methoxymethyl)-1-({4-[(4-methylpyrazol-1-yl)methyl]phenyl}methyl)pyrazole-4-carboxamide;

3-amino-N-[2-(3-chlorophenoxy)ethyl]-1-{[6-(pyrrolidin-1-yl)pyridin-3-yl]methyl}pyrazole-4-carboxamide;

3-amino-N-[2-(3-chlorophenoxy)ethyl]-1-{[2-(pyrrolidin-1-yl)pyridin-4-yl]methyl}pyrazole-4-carboxamide;

3-amino-N-[2-(3-chlorophenoxy)ethyl]-1-({4-[(pyrrolidin-1-yl)carbonyl]phenyl}methyl)pyrazole-4-carboxamide;

3-amino-N-[2-(3-chlorophenoxy)ethyl]-1-{[4-(2-oxopyridin-1-yl)phenyl]methyl}pyrazole-4-carboxamide;

3-amino-N-[2-(3-chlorophenoxy)ethyl]-1-{[6-(pyrrolidin-1-yl)pyridin-2-yl]methyl}pyrazole-4-carboxamide;

3-amino-N-[2-(3-chlorophenoxy)ethyl]-1-[(2-methylquinolin-6-yl)methyl]pyrazole-4-carboxamide;

3-amino-1-[(4-bromophenyl)methyl]-N-[2-(3-chlorophenoxy)ethyl]pyrazole-4-carboxamide;

3-amino-1-[(3-bromophenyl)methyl]-N-[2-(3-chlorophenoxy)ethyl]pyrazole-4-carboxamide;

3-amino-N-[2-(3-chlorophenoxy)ethyl]-1-{[3-(1,3-thiazol-5-yl)phenyl]methyl}pyrazole-4-carboxamide;

methyl 4-[(3-amino-4-{[2-(3-chlorophenoxy)ethyl]carbamoyl}pyrazol-1-yl)methyl]benzoate;

3-amino-N-[2-(3-chlorophenoxy)ethyl]-1-{[4-(dimethylcarbamoyl)phenyl]methyl}pyrazole-4-carboxamide;

3-amino-N-[2-(3-chlorophenoxy)ethyl]-1-({4-[(piperidin-1-yl)carbonyl]phenyl}methyl)pyrazole-4-carboxamide;

3-amino-N-[2-(3-chlorophenoxy)ethyl]-1-{[4-(methylcarbamoyl)phenyl]methyl}pyrazole-4-carboxamide;

ethyl 3-[(3-amino-4-{[2-(3-chlorophenoxy)ethyl]carbamoyl}pyrazol-1-yl)methyl]benzoate;

3-[(3-amino-4-{[2-(3-chlorophenoxy)ethyl]carbamoyl}pyrazol-1-yl)methyl]benzoic acid;

3-amino-N-[2-(3-chlorophenoxy)ethyl]-1-{[3-(methylcarbamoyl)phenyl]methyl}pyrazole-4-carboxamide;

3-amino-N-[2-(3-chlorophenoxy)ethyl]-1-{[3-(dimethylcarbamoyl)phenyl]methyl}pyrazole-4-carboxamide;

3-amino-N-[2-(3-chlorophenoxy)ethyl]-1-{[2-(pyrazol-1-yl)pyridin-4-yl]methyl}pyrazole-4-carboxamide;

({4-[(3-amino-4-{[2-(3-chlorophenoxy)ethyl]carbamoyl}pyrazol-1-yl)methyl]pyridin-2-yl}(methyl)amino)acetic acid 3-amino-N-[2-(3-chlorophenoxy)ethyl]-1-[(2-{[(methylcarbamoyl)methyl]amino}pyridin-4-yl)methyl]pyrazole-4-carboxamide;

4-[(3-amino-4-{[2-(3-chlorophenoxy)ethyl]carbamoyl}pyrazol-1-yl)methyl]benzoic acid;

3-amino-N-[2-(3-chlorophenoxy)ethyl]-1-({3-[(pyrrolidin-1-yl)carbonyl]phenyl}methyl)pyrazole-4-carboxamide;

3-amino-N-[2-(3-chlorophenoxy)ethyl]-1-[(4-phenoxyphenyl)methyl]pyrazole-4-carboxamide;

3-amino-N-[2-(3-chlorophenoxy)ethyl]-1-[(6-phenylpyridin-2-yl)methyl]pyrazole-4-carboxamide;

3-amino-N-[2-(3-chlorophenoxy)ethyl]-1-[(2-methoxypyridin-4-yl)methyl]pyrazole-4-carboxamide;

3-amino-N-[2-(3-chlorophenoxy)ethyl]-1-[(2-{methyl[(methylcarbamoyl)methyl]amino}pyridin-4-yl)methyl]pyrazole-4-carboxamide;

3-amino-N-[2-(3-chlorophenoxy)ethyl]-1-({4-[(pyrimidin-2-yloxy)methyl]phenyl}methyl)pyrazole-4-carboxamide;

3-amino-N-[2-(3-chlorophenoxy)ethyl]-1-({4-[(3-oxomorpholin-4-yl)methyl]phenyl}methyl)pyrazole-4-carboxamide;

3-amino-N-[2-(3-chlorophenoxy)ethyl]-1-({4-[(2-oxopiperidin-1-yl)methyl]phenyl}methyl)pyrazole-4-carboxamide;

3-amino-N-[2-(3-chlorophenoxy)ethyl]-1-[(6-{[(methylcarbamoyl)methyl]amino}pyridin-3-yl)methyl]pyrazole-4-carboxamide;

3-amino-N-[2-(3-chlorophenoxy)ethyl]-1-{[4-(pyrimidin-2-yl)phenyl]methyl}pyrazole-4-carboxamide;

3-amino-N-[2-(3-chlorophenoxy)ethyl]-1-[(3-phenyl-1,2,4-oxadiazol-5-yl)methyl]pyrazole-4-carboxamide;

3-amino-N-[2-(3-chlorophenoxy)ethyl]-1-[(6-chloropyridin-2-yl)methyl]pyrazole-4-carboxamide;

3-amino-N-[2-(3-chlorophenoxy)ethyl]-1-({4-[(N-methylacetamido)methyl]phenyl}methyl)pyrazole-4-carboxamide;

3-amino-N-[2-(3-chlorophenoxy)ethyl]-1-[(4-{[(dimethylcarbamoyl)(methyl)amino]methyl}phenyl)methyl]pyrazole-4-carboxamide;

3-amino-N-[2-(3-chlorophenoxy)ethyl]-1-({4-[(N,2-dimethylpropanamido)methyl]phenyl}methyl)pyrazole-4-carboxamide;

3-amino-N-[2-(3-chlorophenoxy)ethyl]-1-({4-[(3-methyl-2-oxopyridin-1-yl)methyl]phenyl}methyl)pyrazole-4-carboxamide;

3-amino-N-[2-(3-chlorophenoxy)ethyl]-1-({4-[(2-oxopyrimidin-1-yl)methyl]phenyl}methyl)pyrazole-4-carboxamide;

3-amino-N-[2-(3-chlorophenoxy)ethyl]-1-[(4-{[methyl(pyridin-2-yl)amino]methyl}phenyl)methyl]pyrazole-4-carboxamide;

3-amino-N-[2-(3-chlorophenoxy)ethyl]-1-{[6-(pyrazol-1-yl)pyridin-3-yl]methyl}pyrazole-4-carboxamide;

3-amino-N-[2-(3-chlorophenoxy)ethyl]-1-{[6-(4-methylpyrazol-1-yl)pyridin-3-yl]methyl}pyrazole-4-carboxamide;

3-amino-1-[(3-benzyl-1,2,4-oxadiazol-5-yl)methyl]-N-[2-(3-chlorophenoxy)ethyl]pyrazole-4-carboxamide;

3-amino-N-[2-(3-chlorophenoxy)ethyl]-1-{[2-(pyridin-3-yl)pyridin-4-yl]methyl}pyrazole-4-carboxamide;

3-amino-N-[2-(3-chlorophenoxy)ethyl]-1-(1H-indazol-5-ylmethyl)pyrazole-4-carboxamide;

3-amino-N-[2-(3-chlorophenoxy)ethyl]-1-[(1-methylindazol-5-yl)methyl]pyrazole-4-carboxamide;

3-amino-N-[2-(3-chlorophenoxy)ethyl]-1-{[2-(2-oxopyrrolidin-1-yl)pyridin-4-yl]methyl}pyrazole-4-carboxamide;

3-amino-N-[2-(3-chlorophenoxy)ethyl]-1-[(1,2-dimethyl-1,3-benzodiazol-5-yl)methyl]pyrazole-4-carboxamide;

3-amino-N-[2-(3-chlorophenoxy)ethyl]-1-{[6-(2-oxopyrrolidin-1-yl)pyridin-3-yl]methyl}pyrazole-4-carboxamide;

3-amino-N-[2-(3-chlorophenoxy)ethyl]-1-{[6-(pyridin-3-yl)pyridin-3-yl]methyl}pyrazole-4-carboxamide;

3-amino-N-[2-(3-chlorophenoxy)ethyl]-1-({3-methoxy-4-[(2-oxopyridin-1-yl)methyl]phenyl}methyl)pyrazole-4-carboxamide;

3-amino-N-[2-(3-chlorophenoxy)ethyl]-1-({4-[(2-fluoro-6-oxopyridin-1-yl)methyl]phenyl}methyl)pyrazole-4-carboxamide;

3-amino-N-[2-(3-chlorophenoxy)ethyl]-1-({4-[(5-fluoro-2-oxopyridin-1-yl)methyl]phenyl}methyl)pyrazole-4-carboxamide;

3-amino-N-[2-(3-chlorophenoxy)ethyl]-1-({2-fluoro-4-[(2-oxopyridin-1-yl)methyl]phenyl}methyl)pyrazole-4-carboxamide;

3-amino-N-[2-(3-chlorophenoxy)ethyl]-1-({5-[(2-oxopyridin-1-yl)methyl]pyridin-2-yl}methyl)pyrazole-4-carboxamide;

N-[2-(3-chlorophenoxy)ethyl]-1-{[6-(pyrrolidin-1-yl)pyridin-3-yl]methyl}-3-(trifluoromethyl)pyrazole-4-carboxamide;

N-[2-(3-chlorophenoxy)ethyl]-3-(methoxymethyl)-1-({4-[(4-methyl-2-oxopyridin-1-yl)methyl]phenyl}methyl)pyrazole-4-carboxamide;

3-amino-N-[(2S)-2-(3-chlorophenoxy)propyl]-1-({4-[(5-fluoro-2-oxopyridin-1-yl)methyl]phenyl}methyl)pyrazole-4-carboxamide;

3-amino-N-[(3S)-1-(3-chlorophenyl)pyrrolidin-3-yl]-1-({4-[(2-oxopyridin-1-yl)methyl]phenyl}methyl)pyrazole-4-carboxamide;

3-amino-N-[(3R)-1-(3-chlorophenyl)pyrrolidin-3-yl]-1-({4-[(2-oxopyridin-1-yl)methyl]phenyl}methyl)pyrazole-4-carboxamide;

3-amino-N-[(3S)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3R)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3S)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3R)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3S)-1-(3-chlorophenyl)-5-oxopyrrolidin-3-yl]-1-({4-[(2-oxopyridin-1-yl)methyl]phenyl}methyl)pyrazole-4-carboxamide;

3-amino-N-[(3S)-1-(4-chloropyridin-2-yl)pyrrolidin-3-yl]-1-({4-[(2-oxopyridin-1-yl)methyl]phenyl}methyl)pyrazole-4-carboxamide;

3-amino-N-[(2R)-1-(3-chlorophenoxy)propan-2-yl]-1-({4-[(2-oxopyridin-1-yl)methyl]phenyl}methyl)pyrazole-4-carboxamide;

3-amino-N-[(2S)-1-(3-chlorophenoxy)propan-2-yl]-1-({4-[(2-oxopyridin-1-yl)methyl]phenyl}methyl)pyrazole-4-carboxamide;

3-amino-N-[(2S)-2-(3-chlorophenoxy)propyl]-1-({4-[(2-oxopyridin-1-yl)methyl]phenyl}methyl)pyrazole-4-carboxamide;

(2S)-2-{[3-amino-1-({4-[(2-oxopyridin-1-yl)methyl]phenyl}methyl)pyrazol-4-yl]formamido}-N-(3-chlorophenyl)-N-methylpropanamide;

(2R)-2-{[3-amino-1-({4-[(2-oxopyridin-1-yl)methyl]phenyl}methyl)pyrazol-4-yl]formamido}-N-(3-chlorophenyl)-N-methylpropanamide; or 3-amino-N-[(2R/S)-2-(3-chlorophenoxy)propyl]-1-({4-[(2-oxopyridin-1-yl)methyl]phenyl}methyl)pyrazole-4-carboxamide;

or a pharmaceutically acceptable salt or solvate thereof.

15. A compound according to claim 1, that is:

3-amino-1-[4-(2-oxo-2H-pyridin-1-ylmethyl)-benzyl]-1H-pyrazole-4-carboxylic acid [2-(3-chloro-phenoxy)-ethyl]-amide;

3-amino-1-[4-(2-oxo-2H-pyridin-1-ylmethyl)-benzyl]-1H-pyrazole-4-carboxylic acid [(3-chloro-phenylcarbamoyl)-methyl]-amide];

3-amino-N-[(2S)-2-(3-chlorophenoxy)propyl]-1-({4-[(2-oxopyridin-1-yl)methyl]phenyl}methyl)pyrazole-4-carboxamide;

N-[2-(3-chlorophenoxy)ethyl]-3-cyclopropyl-1-({4-[(2-oxopyridin-1-yl)methyl]phenyl}methyl)pyrazole-4-carboxamide;

N-[2-(3-chlorophenoxy)ethyl]-3-(methoxymethyl)-1-({4-[(2-oxopyridin-1-yl)methyl]phenyl}methyl)pyrazole-4-carboxamide;

N-[2-(5-chloro-2-fluorophenoxy)ethyl]-3-(methoxymethyl)-1-({4-[(2-oxopyridin-1-yl)methyl]phenyl}methyl)pyrazole-4-carboxamide;

N-[2-(3-chloro-5-fluorophenoxy)ethyl]-3-(methoxymethyl)-1-({4-[(2-oxopyridin-1-yl)methyl]phenyl}methyl)pyrazole-4-carboxamide;

N-[2-(3-chloro-4-fluorophenoxy)ethyl]-3-(methoxymethyl)-1-({4-[(2-oxopyridin-1-yl)methyl]phenyl}methyl)pyrazole-4-carboxamide;

3-amino-N-[2-(5-chloro-2-methylphenoxy)ethyl]-1-({4-[(2-oxopyridin-1-yl)methyl]phenyl}methyl)pyrazole-4-carboxamide;

3-amino-N-[2-(3-chloro-4-methylphenoxy)ethyl]-1-({4-[(2-oxopyridin-1-yl)methyl]phenyl}methyl)pyrazole-4-carboxamide;

3-amino-N-[2-(3,4-dichlorophenoxy)ethyl]-1-({4-[(2-oxopyridin-1-yl)methyl]phenyl}methyl)pyrazole-4-carboxamide;

3-amino-N-[2-(5-chloro-2-cyanophenoxy)ethyl]-1-({4-[(2-oxopyridin-1-yl)methyl]phenyl}methyl)pyrazole-4-carboxamide;
3-amino-N-[2-(3-chloro-5-methylphenoxy)ethyl]-1-({4-[(2-oxopyridin-1-yl)methyl]phenyl}methyl)pyrazole-4-carboxamide;
3-amino-N-[2-(2,5-dichlorophenoxy)ethyl]-1-({4-[(2-oxopyridin-1-yl)methyl]phenyl}methyl)pyrazole-4-carboxamide;
N-[2-(3-chlorophenoxy)ethyl]-3-methyl-1-({4-[(2-oxopyridin-1-yl)methyl]phenyl}methyl)pyrazole-4-carboxamide;
2-{[3-amino-1-({4-[(2-oxopyridin-1-yl)methyl]phenyl}methyl)pyrazol-4-yl]formamido}-N-(3-chlorophenyl)-N-methylacetamide;
3-amino-N-{2-[(3-chlorophenyl)(methyl)amino]ethyl}-1-({4-[(2-oxopyridin-1-yl)methyl]phenyl}methyl)pyrazole-4-carboxamide;
3-amino-N-[3-(3-chlorophenyl)propyl]-1-({4-[(2-oxopyridin-1-yl)methyl]phenyl}methyl)pyrazole-4-carboxamide;
N-[2-(3-chlorophenoxy)ethyl]-2-methyl-1-({4-[(2-oxopyridin-1-yl)methyl]phenyl}methyl)imidazole-4-carboxamide 3-amino-N-{2-[(4-chloropyridin-2-yl)amino]ethyl}-1-({4-[(2-oxopyridin-1-yl)methyl]phenyl}methyl)pyrazole-4-carboxamide;
N-[2-(3-chlorophenoxy)ethyl]-3-(methoxymethyl)-1-({4-[(4-methylpyrazol-1-yl)methyl]phenyl}methyl)pyrazole-4-carboxamide;
3-amino-N-[2-(3-chlorophenoxy)ethyl]-1-[(2-methylquinolin-6-yl)methyl]pyrazole-4-carboxamide;
3-amino-N-[2-(3-chlorophenoxy)ethyl]-1-({4-[(3-oxomorpholin-4-yl)methyl]phenyl}methyl)pyrazole-4-carboxamide;
3-amino-N-[2-(3-chlorophenoxy)ethyl]-1-({4-[(2-oxopiperidin-1-yl)methyl]phenyl}methyl)pyrazole-4-carboxamide;
3-amino-N-[2-(3-chlorophenoxy)ethyl]-1-[(4-{[(dimethylcarbamoyl)(methyl)amino]methyl}phenyl)methyl]pyrazole-4-carboxamide;
3-amino-N-[2-(3-chlorophenoxy)ethyl]-1-({4-[(3-methyl-2-oxopyridin-1-yl)methyl]phenyl}methyl)pyrazole-4-carboxamide;
3-amino-N-[2-(3-chlorophenoxy)ethyl]-1-({4-[(2-oxopyrimidin-1-yl)methyl]phenyl}methyl)pyrazole-4-carboxamide;
3-amino-N-[2-(3-chlorophenoxy)ethyl]-1-({3-methoxy-4-[(2-oxopyridin-1-yl)methyl]phenyl}methyl)pyrazole-4-carboxamide;
3-amino-N-[2-(3-chlorophenoxy)ethyl]-1-({4-[(5-fluoro-2-oxopyridin-1-yl)methyl]phenyl}methyl)pyrazole-4-carboxamide;
3-amino-N-[2-(3-chlorophenoxy)ethyl]-1-({2-fluoro-4-[(2-oxopyridin-1-yl)methyl]phenyl}methyl)pyrazole-4-carboxamide;
3-amino-N-[2-(3-chlorophenoxy)ethyl]-1-({5-[(2-oxopyridin-1-yl)methyl]pyridin-2-yl}methyl)pyrazole-4-carboxamide;
3-amino-N-[(3S)-1-(3-chlorophenyl)pyrrolidin-3-yl]-1-({4-[(2-oxopyridin-1-yl)methyl]phenyl}methyl)pyrazole-4-carboxamide;
3-amino-N-[(3S)-1-(3-chlorophenyl)-2-oxopyrrolidin-3-yl]-1-({4-[(2-oxopyridin-1-yl)methyl]phenyl}methyl)pyrazole-4-carboxamide;
3-amino-N-[(3R)-1-[(3-chlorophenyl)methyl]pyrrolidin-3-yl]-1-({4-[(2-oxopyridin-1-yl)methyl]phenyl}methyl)pyrazole-4-carboxamide;
3-amino-N-[(3R)-1-(3-chlorophenyl)-2-oxopyrrolidin-3-yl]-1-({4-[(2-oxopyridin-1-yl)methyl]phenyl}methyl)pyrazole-4-carboxamide;
3-amino-N-[(3S)-1-(3-chlorophenyl)-5-oxopyrrolidin-3-yl]-1-({4-[(2-oxopyridin-1-yl)methyl]phenyl}methyl)pyrazole-4-carboxamide;
3-amino-N-[(2S)-1-(3-chlorophenoxy)propan-2-yl]-1-({4-[(2-oxopyridin-1-yl)methyl]phenyl}methyl)pyrazole-4-carboxamide; or
3-amino-N-[(2R/S)-2-(3-chlorophenoxy)propyl]-1-({4-[(2-oxopyridin-1-yl)methyl]phenyl}methyl)pyrazole-4-carboxamide;

or a pharmaceutically acceptable salt or solvate thereof.

16. A pharmaceutical composition comprising a compound of claim 1 and a pharmaceutically acceptable carrier, diluent or excipient.

17. A method of palliatively or prophylactically treating a disease or condition in which plasma kallikrein activity is implicated, comprising administering to a subject in need thereof a therapeutically effective amount of a compound of claim 1.

18. The method of claim 17, wherein the disease or condition in which plasma kallikrein activity is implicated is impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery, or bleeding from post operative surgery.

19. The method of claim 17, wherein the disease or condition in which plasma kallikrein activity is implicated is retinal vascular permeability associated with diabetic retinopathy or diabetic macular edema.

20. The method of claim 17, wherein the disease or condition in which plasma kallikrein activity is implicated is diabetic macular edema.

21. The method of claim 17, wherein the disease or condition in which plasma kallikrein activity is implicated is hereditary angioedema.

22. A pharmaceutical composition comprising a compound of claim 14 and a pharmaceutically acceptable carrier, diluent or excipient.

23. A method of palliatively or prophylactically treating a disease or condition in which plasma kallikrein activity is implicated, comprising administering to a subject in need thereof a therapeutically effective amount of a compound of claim 14.

24. A compound according to claim 1, that is:
3-amino-1-[4-(2-oxo-2H-pyridin-1-ylmethyl)-benzyl]-1H-pyrazole-4-carboxylic acid [2-(3-chloro-phenoxy)-ethyl]-amide;
3-amino-1-[4-(2-oxo-2H-pyridin-1-ylmethyl)-benzyl]-1H-pyrazole-4-carboxylic acid [(3-chloro-phenylcarbamoyl)-methyl]-amide];
2-{[3-amino-1-({4-[(2-oxopyridin-1-yl)methyl]phenyl}methyl)pyrazol-4-yl]formamido}-N-(2-chlorophenyl)acetamide;
2-{[3-amino-1-({4-[(2-oxopyridin-1-yl)methyl]phenyl}methyl)pyrazol-4-yl]formamido}-N-(4-chlorophenyl)acetamide;
N-[2-(3-chlorophenoxy)ethyl]-3-cyclopropyl-1-({4-[(2-oxopyridin-1-yl)methyl]phenyl}methyl)pyrazole-4-carboxamide;

N-[2-(2-chlorophenoxy)ethyl]-3-(methoxymethyl)-1-({4-[(2-oxopyridin-1-yl)methyl]phenyl}methyl)pyrazole-4-carboxamide;

N-[2-(3-chlorophenoxy)ethyl]-1-({4-[(2-oxopyridin-1-yl)methyl]phenyl}methyl)-3-(trifluoromethyl)pyrazole-4-carboxamide;

N-[2-(3-chlorophenoxy)ethyl]-3-(methoxymethyl)-1-({4-[(2-oxopyridin-1-yl)methyl]phenyl}methyl)pyrazole-4-carboxamide;

N-[2-(5-chloro-2-fluorophenoxy)ethyl]-3-(methoxymethyl)-1-({4-[(2-oxopyridin-1-yl)methyl]phenyl}methyl)pyrazole-4-carboxamide;

N-[2-(3-chloro-5-fluorophenoxy)ethyl]-3-(methoxymethyl)-1-({4-[(2-oxopyridin-1-yl)methyl]phenyl}methyl)pyrazole-4-carboxamide;

N-[2-(3-chloro-5-methoxyphenoxy)ethyl]-3-(methoxymethyl)-1-({4-[(2-oxopyridin-1-yl)methyl]phenyl}methyl)pyrazole-4-carboxamide;

N-[2-(3-chloro-4-fluorophenoxy)ethyl]-3-(methoxymethyl)-1-({4-[(2-oxopyridin-1-yl)methyl]phenyl}methyl)pyrazole-4-carboxamide;

3-amino-N-[2-(5-chloro-2-methylphenoxy)ethyl]-1-({4-[(2-oxopyridin-1-yl)methyl]phenyl}methyl)pyrazole-4-carboxamide;

3-amino-N-[2-(3-chloro-4-methylphenoxy)ethyl]-1-({4-[(2-oxopyridin-1-yl)methyl]phenyl}methyl)pyrazole-4-carboxamide;

3-amino-N-[2-(2,3-dichlorophenoxy)ethyl]-1-({4-[(2-oxopyridin-1-yl)methyl]phenyl}methyl)pyrazole-4-carboxamide;

3-amino-N-[2-(3,4-dichlorophenoxy)ethyl]-1-({4-[(2-oxopyridin-1-yl)methyl]phenyl}methyl)pyrazole-4-carboxamide;

3-amino-N-[2-(3,5-dichlorophenoxy)ethyl]-1-({4-[(2-oxopyridin-1-yl)methyl]phenyl}methyl)pyrazole-4-carboxamide;

3-amino-N-[2-(5-chloro-2-cyanophenoxy)ethyl]-1-({4-[(2-oxopyridin-1-yl)methyl]phenyl}methyl)pyrazole-4-carboxamide; or 3-amino-N-[2-(3-chloro-5-methylphenoxy)ethyl]-1-({4-[(2-oxopyridin-1-yl)methyl]phenyl}methyl)pyrazole-4-carboxamide;

or a pharmaceutically acceptable salt or solvate thereof.

25. A compound according to claim 1, that is:

3-amino-N-[2-(2,5-dichlorophenoxy)ethyl]-1-({4-[(2-oxopyridin-1-yl)methyl]phenyl}methyl)pyrazole-4-carboxamide;

N-[2-(3-chlorophenoxy)ethyl]-3-cyano-1-({4-[(2-oxopyridin-1-yl)methyl]phenyl}methyl)pyrazole-4-carboxamide;

N-[2-(3-chlorophenoxy)ethyl]-3-methyl-1-({4-[(2-oxopyridin-1-yl)methyl]phenyl}methyl)pyrazole-4-carboxamide;

2-{3-amino-1-({4-[(2-oxopyridin-1-yl)methyl]phenyl}methyl)pyrazol-4-yl]formamido}-N-(3-chlorophenyl)-N-methylacetamide;

3-amino-N-{2-[(3-chlorophenyl)(methyl)amino]ethyl}-1-({4-[(2-oxopyridin-1-yl)methyl]phenyl}methyl)pyrazole-4-carboxamide;

3-amino-N-[3-(3-chlorophenyl)propyl]-1-({4-[(2-oxopyridin-1-yl)methyl]phenyl}methyl)pyrazole-4-carboxamide;

N-{2-[(5-chloropyridin-3-yl)oxy]ethyl}-2-methyl-1-({4-[(2-oxopyridin-1-yl)methyl]phenyl}methyl)imidazole-4-carboxamide;

N-[2-(3-chlorophenoxy)ethyl]-2-methyl-1-({4-[(2-oxopyridin-1-yl)methyl]phenyl}methyl)imidazole-4-carboxamide;

3-amino-N-{2-[(5-chloropyridin-3-yl)oxy]ethyl}-1-({4-[(2-oxopyridin-1-yl)methyl]phenyl}methyl)pyrazole-4-carboxamide;

N-[3-(5-chloro-2-oxopyrimidin-1-yl)propyl]-3-(methoxymethyl)-1-({4-[(2-oxopyridin-1-yl)methyl]phenyl}methyl)pyrazole-4-carboxamide;

N-[3-(5-chloro-1,3-thiazol-2-yl)propyl]-3-(methoxymethyl)-1-({4-[(2-oxopyridin-1-yl)methyl]phenyl}methyl)pyrazole-4-carboxamide;

3-amino-N-[3-(4-chloropyrazol-1-yl)propyl]-1-({4-[(2-oxopyridin-1-yl)methyl]phenyl}methyl)pyrazole-4-carboxamide;

3-amino-N-{2-[(4-chloro-1H-pyrazol-3-yl)oxy]ethyl}-1-({4-[(2-oxopyridin-1-yl)methyl]phenyl}methyl)pyrazole-4-carboxamide;

N-{2-[(5-chloro-1,3-thiazol-2-yl)oxy]ethyl}-3-(methoxymethyl)-1-({4-[(2-oxopyridin-1-yl)methyl]phenyl}methyl)pyrazole-4-carboxamide;

N-[3-(5-chloro-1,2-oxazol-3-yl)propyl]-3-(methoxymethyl)-1-({4-[(2-oxopyridin-1-yl)methyl]phenyl}methyl)pyrazole-4-carboxamide;

N-{2-[(4-chlorothiophen-2-yl)sulfanyl]ethyl}-3-(methoxymethyl)-1-({4-[(2-oxopyridin-1-yl)methyl]phenyl}methyl)pyrazole-4-carboxamide;

N-{2-[(4-chlorofuran-2-yl)sulfanyl]ethyl}-3-(methoxymethyl)-1-({4-[(2-oxopyridin-1-yl)methyl]phenyl}methyl)pyrazole-4-carboxamide; or N-{2-[(5-chloropyridazin-3-yl)oxy]ethyl}-3-(methoxymethyl)-1-({4-[(2-oxopyridin-1-yl)methyl]phenyl}methyl)pyrazole-4-carboxamide;

or a pharmaceutically acceptable salt or solvate thereof.

26. A compound according to claim 1, that is:

3-amino-N-{2-[(4-chloropyridin-2-yl)amino]ethyl}-1-({4-[(2-oxopyridin-1-yl)methyl]phenyl}methyl)pyrazole-4-carboxamide;

N-[2-(3-chlorophenoxy)ethyl]-3-(methoxymethyl)-1-({4-[(4-methylpyrazol-1-yl)methyl]phenyl}methyl)pyrazole-4-carboxamide;

3-amino-N-[2-(3-chlorophenoxy)ethyl]-1-{[6-(pyrrolidin-1-yl)pyridin-3-yl]methyl}pyrazole-4-carboxamide;

3-amino-N-[2-(3-chlorophenoxy)ethyl]-1-{[2-(pyrrolidin-1-yl)pyridin-4-yl]methyl}pyrazole-4-carboxamide;

3-amino-N-[2-(3-chlorophenoxy)ethyl]-1-({4-[(pyrrolidin-1-yl)carbonyl]phenyl}methyl)pyrazole-4-carboxamide;

3-amino-N-[2-(3-chlorophenoxy)ethyl]-1-{[4-(2-oxopyridin-1-yl)phenyl]methyl}pyrazole-4-carboxamide;

3-amino-N-[2-(3-chlorophenoxy)ethyl]-1-{[6-(pyrrolidin-1-yl)pyridin-2-yl]methyl}pyrazole-4-carboxamide;

3-amino-N-[2-(3-chlorophenoxy)ethyl]-1-[(2-methylquinolin-6-yl)methyl]pyrazole-4-carboxamide;

3-amino-1-[(4-bromophenyl)methyl]-N-[2-(3-chlorophenoxy)ethyl]pyrazole-4-carboxamide;

3-amino-1-[(3-bromophenyl)methyl]-N-[2-(3-chlorophenoxy)ethyl]pyrazole-4-carboxamide;

3-amino-N-[2-(3-chlorophenoxy)ethyl]-1-{[3-(1,3-thiazol-5-yl)phenyl]methyl}pyrazole-4-carboxamide;

methyl 4-[(3-amino-4-{[2-(3-chlorophenoxy)ethyl]carbamoyl}pyrazol-1-yl)methyl]benzoate;

3-amino-N-[2-(3-chlorophenoxy)ethyl]-1-{[4-(dimethylcarbamoyl)phenyl]methyl}pyrazole-4-carboxamide;
3-amino-N-[2-(3-chlorophenoxy)ethyl]-1-({4-[(piperidin-1-yl)carbonyl]phenyl}methyl)pyrazole-4-carboxamide;
3-amino-N-[2-(3-chlorophenoxy)ethyl]-1-{[4-(methylcarbamoyl)phenyl]methyl}pyrazole-4-carboxamide;
ethyl 3-[(3-amino-4-{[2-(3-chlorophenoxy)ethyl]carbamoyl}pyrazol-1-yl)methyl]benzoate;
3-[(3-amino-4-{[2-(3-chlorophenoxy)ethyl]carbamoyl}pyrazol-1-yl)methyl]benzoic acid; or
3-amino-N-[2-(3-chlorophenoxy)ethyl]-1-{[3-(methylcarbamoyl)phenyl]methyl}pyrazole-4-carboxamide;
or a pharmaceutically acceptable salt or solvate thereof.

27. A compound according to claim 1, that is:
3-amino-N-[2-(3-chlorophenoxy)ethyl]-1-{[3-(dimethylcarbamoyl)phenyl]methyl}pyrazole-4-carboxamide;
3-amino-N-[2-(3-chlorophenoxy)ethyl]-1-{[2-(pyrazol-1-yl)pyridin-4-yl]methyl}pyrazole-4-carboxamide;
({4-[(3-amino-4-{[2-(3-chlorophenoxy)ethyl]carbamoyl}pyrazol-1-yl)methyl]pyridin-2-yl}(methyl)amino)acetic acid
3-amino-N-[2-(3-chlorophenoxy)ethyl]-1-[(2-{[(methylcarbamoyl)methyl]amino}pyridin-4-yl)methyl]pyrazole-4-carboxamide;
4-[(3-amino-4-{[2-(3-chlorophenoxy)ethyl]carbamoyl}pyrazol-1-yl)methyl]benzoic acid;
3-amino-N-[2-(3-chlorophenoxy)ethyl]-1-({3-[(pyrrolidin-1-yl)carbonyl]phenyl}methyl)pyrazole-4-carboxamide;
3-amino-N-[2-(3-chlorophenoxy)ethyl]-1-[(4-phenoxyphenyl)methyl]pyrazole-4-carboxamide;
3-amino-N-[2-(3-chlorophenoxy)ethyl]-1-[(6-phenylpyridin-2-yl)methyl]pyrazole-4-carboxamide;
3-amino-N-[2-(3-chlorophenoxy)ethyl]-1-[(2-methoxypyridin-4-yl)methyl]pyrazole-4-carboxamide;
3-amino-N-[2-(3-chlorophenoxy)ethyl]-1-[(2-{methyl[(methylcarbamoyl)methyl]amino}pyridin-4-yl)methyl]pyrazole-4-carboxamide;
3-amino-N-[2-(3-chlorophenoxy)ethyl]-1-({4-[(pyrimidin-2-yloxy)methyl]phenyl}methyl)pyrazole-4-carboxamide;
3-amino-N-[2-(3-chlorophenoxy)ethyl]-1-({4-[(3-oxomorpholin-4-yl)methyl]phenyl}methyl)pyrazole-4-carboxamide;
3-amino-N-[2-(3-chlorophenoxy)ethyl]-1-({4-[(2-oxopiperidin-1-yl)methyl]phenyl}methyl)pyrazole-4-carboxamide;
3-amino-N-[2-(3-chlorophenoxy)ethyl]-1-[(6-{[(methylcarbamoyl)methyl]amino}pyridin-3-yl)methyl]pyrazole-4-carboxamide;
3-amino-N-[2-(3-chlorophenoxy)ethyl]-1-{[4-(pyrimidin-2-yl)phenyl]methyl}pyrazole-4-carboxamide;
3-amino-N-[2-(3-chlorophenoxy)ethyl]-1-[(3-phenyl-1,2,4-oxadiazol-5-yl)methyl]pyrazole-4-carboxamide;
3-amino-N-[2-(3-chlorophenoxy)ethyl]-1-[(6-chloropyridin-2-yl)methyl]pyrazole-4-carboxamide; or
3-amino-N-[2-(3-chlorophenoxy)ethyl]-1-({4-[(N-methylacetamido)methyl]phenyl}methyl)pyrazole-4-carboxamide;
or a pharmaceutically acceptable salt or solvate thereof.

28. A compound according to claim 1, that is:
3-amino-N-[2-(3-chlorophenoxy)ethyl]-1-[(4-{[(dimethylcarbamoyl)(methyl)amino]methyl}phenyl)methyl]pyrazole-4-carboxamide;
3-amino-N-[2-(3-chlorophenoxy)ethyl]-1-({4-[(N,2-dimethylpropanamido)methyl]phenyl}methyl)pyrazole-4-carboxamide;
3-amino-N-[2-(3-chlorophenoxy)ethyl]-1-({4-[(3-methyl-2-oxopyridin-1-yl)methyl]phenyl}methyl)pyrazole-4-carboxamide;
3-amino-N-[2-(3-chlorophenoxy)ethyl]-1-({4-[2-oxopyrimidin-1-yl)methyl]phenyl}methyl)pyrazole-4-carboxamide;
3-amino-N-[2-(3-chlorophenoxy)ethyl]-1-[(4-{[methyl(pyridin-2-yl)amino]methyl}phenyl)methyl]pyrazole-4-carboxamide;
3-amino-N-[2-(3-chlorophenoxy)ethyl]-1-{[6-(pyrazol-1-yl)pyridin-3-yl]methyl}pyrazole-4-carboxamide;
3-amino-N-[2-(3-chlorophenoxy)ethyl]-1-{[6-(4-methylpyrazol-1-yl)pyridin-3-yl]methyl}pyrazole-4-carboxamide;
3-amino-1-[(3-benzyl-1,2,4-oxadiazol-5-yl)methyl]-N-[2-(3-chlorophenoxy)ethyl]pyrazole-4-carboxamide;
3-amino-N-[2-(3-chlorophenoxy)ethyl]-1-{[2-(pyridin-3-yl)pyridin-4-yl]methyl}pyrazole-4-carboxamide;
3-amino-N-[2-(3-chlorophenoxy)ethyl]-1-(1H-indazol-5-ylmethyl)pyrazole-4-carboxamide;
3-amino-N-[2-(3-chlorophenoxy)ethyl]-1-[(1-methylindazol-5-yl)methyl]pyrazole-4-carboxamide;
3-amino-N-[2-(3-chlorophenoxy)ethyl]-1-{[2-(2-oxopyrrolidin-1-yl)pyridin-4-yl]methyl}pyrazole-4-carboxamide;
3-amino-N-[2-(3-chlorophenoxy)ethyl]-1-[(1,2-dimethyl-1,3-benzodiazol-5-yl)methyl]pyrazole-4-carboxamide;
3-amino-N-[2-(3-chlorophenoxy)ethyl]-1-{[6-(2-oxopyrrolidin-1-yl)pyridin-3-yl]methyl}pyrazole-4-carboxamide;
3-amino-N-[2-(3-chlorophenoxy)ethyl]-1-{[6-(pyridin-3-yl)pyridin-3-yl]methyl}pyrazole-4-carboxamide;
3-amino-N-[2-(3-chlorophenoxy)ethyl]-1-({3-methoxy-4-[(2-oxopyridin-1-yl)methyl]phenyl}methyl)pyrazole-4-carboxamide;
3-amino-N-[2-(3-chlorophenoxy)ethyl]-1-({4-[(2-fluoro-6-oxopyridin-1-yl)methyl]phenyl}methyl)pyrazole-4-carboxamide; or
3-amino-N-[2-(3-chlorophenoxy)ethyl]-1-({4-[(5-fluoro-2-oxopyridin-1-yl)methyl]phenyl}methyl)pyrazole-4-carboxamide;
or a pharmaceutically acceptable salt or solvate thereof.

29. The compound of claim 1, that is:
3-amino-N-[2-(3-chlorophenoxy)ethyl]-1-({2-fluoro-4-[(2-oxopyridin-1-yl)methyl]phenyl}methyl)pyrazole-4-carboxamide;
3-amino-N-[2-(3-chlorophenoxy)ethyl]-1-({5-[(2-oxopyridin-1-yl)methyl]pyridin-2-yl}methyl)pyrazole-4-carboxamide;
N-[2-(3-chlorophenoxy)ethyl]-1-{[6-(pyrrolidin-1-yl)pyridin-3-yl]methyl}-3-(trifluoromethyl)pyrazole-4-carboxamide;
N-[2-(3-chlorophenoxy)ethyl]-3-(methoxymethyl)-1-({4-[(4-methyl-2-oxopyridin-1-yl)methyl]phenyl}methyl)pyrazole-4-carboxamide;
3-amino-N-[(2S)-2-(3-chlorophenoxy)propyl]-1-({4-[(5-fluoro-2-oxopyridin-1-yl)methyl]phenyl}methyl)pyrazole-4-carboxamide;
3-amino-N-[(3S)-1-(3-chlorophenyl)pyrrolidin-3-yl]-1-({4-[(2-oxopyridin-1-yl)methyl]phenyl}methyl)pyrazole-4-carboxamide;

3-amino-N-[(3R)-1-(3-chlorophenyl)pyrrolidin-3-yl]-1-({4-[(2-oxopyridin-1-yl)methyl]phenyl}methyl)pyrazole-4-carboxamide;

3-amino-N-[(3S)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3R)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3S)-1-[(3-chlorophenyl)methyl]pyrrolidin-3-yl]-1-({4-[(2-oxopyridin-1-yl)methyl]phenyl}methyl)pyrazole-4-carboxamide;

3-amino-N-[(3R)-1-(3-chlorophenyl)-2-oxopyrrolidin-3-yl]-1-({4-[(2-oxopyridin-1-yl)methyl]phenyl}methyl)pyrazole-4-carboxamide;

3-amino-N-[(3S)-1-(3-chlorophenyl)-5-oxopyrrolidin-3-yl]-1-({4-[(2-oxopyridin-1-yl)methyl]phenyl}methyl)pyrazole-4-carboxamide;

3-amino-N-[(3S)-1-(4-chloropyridin-2-yl)pyrrolidin-3-yl]-1-({4-[(2-oxopyridin-1-yl)methyl]phenyl}methyl)pyrazole-4-carboxamide;

3-amino-N-[(2R)-1-(3-chlorophenoxy)propan-2-yl]-1-({4-[(2-oxopyridin-1-yl)methyl]phenyl}methyl)pyrazole-4-carboxamide;

3-amino-N-[(2S)-1-(3-chlorophenoxy)propan-2-yl]-1-({4-[(2-oxopyridin-1-yl)methyl]phenyl}methyl)pyrazole-4-carboxamide;

3-amino-N-[(2S)-2-(3-chlorophenoxy)propyl]-1-({4-[(2-oxopyridin-1-yl)methyl]phenyl}methyl)pyrazole-4-carboxamide;

(2S)-2-{[3-amino-1-({4-[(2-oxopyridin-1-yl)methyl]phenyl}methyl)pyrazol-4-yl]formamido}-N-(3-chlorophenyl)-N-methylpropanamide;

(2R)-2-{[3-amino-1-({4-[(2-oxopyridin-1-yl)methyl]phenyl}methyl)pyrazol-4-yl]formamido}-N-(3-chlorophenyl)-N-methylpropanamide; or 3-amino-N-[(2R/S)-2-(3-chlorophenoxy)propyl]-1-({4-[(2-oxopyridin-1-yl)methyl]phenyl}methyl)pyrazole-4-carboxamide;

or a pharmaceutically acceptable salt or solvate thereof.

30. The compound according to claim 1, wherein W, X, Y, and Z are, independently, C or N.

31. The compound according to claim 1, wherein the ring containing W, X, Y, and Z is thiene or furan substituted by at least one alkyl, —NH2, CN, CF3, or R16.

32. The compound according to claim 1, wherein the ring containing W, X, Y, and Z is a pyrrole, pyrazole, or imidazole.

33. The compound according to claim 1, wherein the ring containing W, X, Y, and Z is pyrazole or imidazole.

34. The compound according to claim 1, wherein W is C, X is N, and Y and Z are C or N.

35. The compound according to claim 1, wherein (i) W is C, X is N, Y is N, and Z is C; or (ii) W is C, X is N, Y is C, and Z is N.

36. A compound that is N-[2-(3-chlorophenoxy)ethyl]-1-({4-[(2-oxopyridin-1-yl)methyl]phenyl}methyl)pyrazole-4-carboxamide, or a pharmaceutically acceptable salt or solvate thereof.

* * * * *